United States Patent
LaDuca et al.

(10) Patent No.: US 10,729,569 B2
(45) Date of Patent: Aug. 4, 2020

(54) DELIVERY DEVICES FOR IMPLANTING DEVICES AT INTERSECTING LUMENS

(75) Inventors: Robert LaDuca, Santa Cruz, CA (US); Paul LaDuca, Little Elm, TX (US)

(73) Assignee: Taheri LaDuca LLC, Santa Cruz, CA (US)

(*) Notice: Subject to any disclaimer, the term of this patent is extended or adjusted under 35 U.S.C. 154(b) by 377 days.

(21) Appl. No.: 12/059,914

(22) Filed: Mar. 31, 2008

(65) Prior Publication Data

US 2008/0183274 A1 Jul. 31, 2008

Related U.S. Application Data

(60) Division of application No. 11/241,242, filed on Sep. 30, 2005, now Pat. No. 8,287,583, which is a continuation-in-part of application No. 11/033,479, filed on Jan. 10, 2005, now abandoned.

(51) Int. Cl.

| A61F 2/954 | (2013.01) |
| A61F 2/856 | (2013.01) |
| A61F 2/90 | (2013.01) |
| A61F 2/95 | (2013.01) |
| A61F 2/06 | (2013.01) |
| A61F 2/844 | (2013.01) |

(Continued)

(52) U.S. Cl.
CPC ............ *A61F 2/954* (2013.01); *A61F 2/06* (2013.01); *A61F 2/844* (2013.01); *A61F 2/856* (2013.01); *A61F 2/90* (2013.01); *A61F 2/95* (2013.01); *A61F 2/2418* (2013.01); *A61F 2002/075* (2013.01); *A61F 2002/9511* (2013.01); *A61F 2002/9517* (2013.01); *A61F 2220/0008* (2013.01); *A61F 2220/0016* (2013.01); *A61F 2220/0041* (2013.01); *A61F 2220/0066* (2013.01); *A61F 2220/0075* (2013.01); *A61F 2250/0039* (2013.01)

(58) Field of Classification Search
CPC .......................... A61B 2/9511; A61F 2/9511
USPC ................... 623/1.11; 606/108, 191, 194
See application file for complete search history.

(56) References Cited

U.S. PATENT DOCUMENTS

| 3,976,071 A | 8/1976 | Sadek |
| 4,335,094 A | 6/1982 | Mosbach |
| 4,345,588 A | 8/1982 | Widder et al. |

(Continued)

FOREIGN PATENT DOCUMENTS

| EP | 1043041 | 10/2000 |
| WO | WO 2003/007823 | 1/2003 |
| WO | WO 2006/076325 | 7/2006 |

OTHER PUBLICATIONS

Kasyanov, V. et al., "Tannic acid mimicking dendrimers as small intestine submucosa stabilizing nanomordants," Biomaterials, 27:745-751, 2005, Elsevier Ltd.

*Primary Examiner* — Katherine M Shi
*Assistant Examiner* — Lindsey Bachman
(74) *Attorney, Agent, or Firm* — Levine Bagade Han LLP

(57) ABSTRACT

The present invention provides devices and methods for fabricating and deploying an implantable device within the body. The invention is particularly suitable for delivering and deploying a stent, graft or stent graft device within a vessel or tubular structure within the body, particularly here the implant site involves two or more interconnecting vessels. The delivery and deployment system utilizes a plurality of strings which are releasably attached to the luminal ends of the implantable device.

20 Claims, 37 Drawing Sheets

(51) Int. Cl.
*A61F 2/24* (2006.01)
*A61F 2/07* (2013.01)

(56) References Cited

U.S. PATENT DOCUMENTS

| | | | |
|---|---|---|---|
| 4,357,259 A | 11/1982 | Senyei et al. |
| 4,501,263 A | 2/1985 | Harbuck |
| 4,501,726 A | 2/1985 | Schroder et al. |
| 4,830,003 A | 5/1989 | Wolff et al. |
| 4,832,686 A | 5/1989 | Anderson |
| 4,871,716 A | 10/1989 | Longo et al. |
| 4,872,874 A | 10/1989 | Taheri |
| 4,883,666 A | 11/1989 | Sabel et al. |
| 4,894,231 A | 1/1990 | Moreau et al. |
| 4,897,268 A | 1/1990 | Tice et al. |
| 4,902,508 A | 2/1990 | Badylak et al. |
| 4,904,479 A | 2/1990 | Illum |
| 4,913,141 A | 4/1990 | Hillstead |
| 4,936,281 A | 6/1990 | Stasz |
| 4,956,178 A | 9/1990 | Badylak et al. |
| 5,000,185 A | 3/1991 | Yock |
| 5,026,377 A | 6/1991 | Burton et al. |
| 5,042,707 A | 8/1991 | Taheri |
| 5,042,976 A | 8/1991 | Ishitsu et al. |
| 5,067,491 A | 11/1991 | Taylor, II et al. |
| 5,069,216 A | 12/1991 | Groman et al. |
| 5,112,457 A | 5/1992 | Marchant |
| 5,163,952 A | 11/1992 | Froix |
| 5,176,907 A | 1/1993 | Leong |
| 5,206,159 A | 4/1993 | Cohen et al. |
| 5,225,282 A | 7/1993 | Chagnon et al. |
| 5,275,826 A | 1/1994 | Badylak et al. |
| 5,286,254 A | 2/1994 | Shapland et al. |
| 5,342,348 A | 8/1994 | Kaplan |
| 5,356,433 A | 10/1994 | Rowland et al. |
| 5,368,557 A | 11/1994 | Nita et al. |
| 5,409,000 A | 4/1995 | Imran |
| 5,411,550 A | 5/1995 | Herweck et al. |
| 5,415,664 A | 5/1995 | Pinchuk |
| 5,419,760 A | 5/1995 | Narciso, Jr. |
| 5,427,767 A | 6/1995 | Kresse et al. |
| 5,447,724 A | 9/1995 | Helmus et al. |
| 5,463,010 A | 10/1995 | Hu et al. |
| 5,464,449 A | 11/1995 | Ryan et al. |
| 5,464,450 A | 11/1995 | Buscemi et al. |
| 5,464,650 A | 11/1995 | Berg et al. |
| 5,484,584 A | 1/1996 | Wallace et al. |
| 5,500,013 A | 3/1996 | Buscemi et al. |
| 5,543,158 A | 8/1996 | Gref et al. |
| 5,545,208 A | 8/1996 | Wolff et al. |
| 5,551,954 A | 9/1996 | Buscemi et al. |
| 5,554,389 A | 9/1996 | Badylak et al. |
| 5,569,463 A | 10/1996 | Helmus et al. |
| 5,591,227 A | 1/1997 | Dinh et al. |
| 5,591,228 A | 1/1997 | Edoga |
| 5,609,627 A | 3/1997 | Goicoechea et al. |
| 5,609,629 A | 3/1997 | Fearnot et al. |
| 5,617,878 A | 4/1997 | Taheri |
| 5,624,411 A | 4/1997 | Tuch |
| 5,637,113 A | 6/1997 | Tartaglia et al. |
| 5,649,977 A | 7/1997 | Campbell |
| 5,653,743 A | 8/1997 | Martin |
| 5,669,924 A | 9/1997 | Shaknovich |
| 5,676,696 A | 10/1997 | Marcade |
| 5,676,697 A | 10/1997 | McDonald |
| 5,693,083 A | 12/1997 | Baker et al. |
| 5,700,269 A | 12/1997 | Pinchuk et al. |
| 5,723,004 A | 3/1998 | Dereume et al. |
| 5,725,494 A | 3/1998 | Brisken |
| 5,728,062 A | 3/1998 | Brisken |
| 5,735,811 A | 4/1998 | Brisken |
| 5,741,325 A | 4/1998 | Chaikof et al. |
| 5,755,735 A | 5/1998 | Richter et al. |
| 5,769,883 A | 6/1998 | Buscemi et al. |
| 5,800,507 A | 9/1998 | Schwartz |
| 5,824,049 A | 10/1998 | Ragheb et al. |
| 5,824,064 A | 10/1998 | Taheri |
| 5,837,008 A | 11/1998 | Berg et al. |
| 5,843,167 A | 12/1998 | Dwyer et al. |
| 5,843,169 A | 12/1998 | Taheri |
| 5,843,172 A | 12/1998 | Yan |
| 5,851,231 A | 12/1998 | Wolff et al. |
| 5,876,452 A | 3/1999 | Athanasiou et al. |
| 5,879,808 A | 3/1999 | Wary et al. |
| 5,891,108 A | 4/1999 | Leone et al. |
| 5,893,840 A | 4/1999 | Hull et al. |
| 5,928,145 A | 7/1999 | Ocali et al. |
| 5,948,017 A | 9/1999 | Taheri |
| 5,951,586 A | 9/1999 | Berg et al. |
| 5,968,092 A | 10/1999 | Buscemi et al. |
| 5,972,027 A | 10/1999 | Johnson |
| 5,980,551 A | 11/1999 | Summers et al. |
| 5,980,566 A | 11/1999 | Alt et al. |
| 5,984,955 A | 11/1999 | Wisselink |
| 5,993,481 A | 11/1999 | Marcade et al. |
| 5,997,468 A | 12/1999 | Wolff et al. |
| 6,017,363 A | 1/2000 | Hojeibane |
| 6,022,319 A | 2/2000 | Willard et al. |
| 6,030,414 A | 2/2000 | Taheri |
| 6,031,375 A | 2/2000 | Atalar et al. |
| 6,033,434 A | 3/2000 | Borghi |
| 6,051,276 A | 4/2000 | Wary et al. |
| 6,059,824 A | 5/2000 | Taheri |
| 6,063,101 A | 5/2000 | Jacobsen et al. |
| 6,071,305 A | 6/2000 | Brown et al. |
| 6,074,362 A | 6/2000 | Jang et al. |
| 6,074,398 A | 6/2000 | Leschinsky |
| 6,077,297 A | 6/2000 | Robinson et al. |
| 6,096,070 A | 8/2000 | Ragheb et al. |
| 6,099,548 A | 8/2000 | Taheri |
| 6,099,561 A | 8/2000 | Alt |
| 6,099,567 A | 8/2000 | Badylak et al. |
| 6,106,549 A | 8/2000 | Taheri |
| 6,129,738 A | 10/2000 | Lashinski et al. |
| 6,183,504 B1 | 2/2001 | Inoue |
| 6,183,509 B1 | 2/2001 | Dibie |
| 6,187,033 B1 | 2/2001 | Schmitt et al. |
| 6,210,429 B1 | 4/2001 | Vardi et al. |
| 6,224,609 B1 | 5/2001 | Ressemann et al. |
| 6,228,052 B1 | 5/2001 | Pohndorf |
| 6,238,432 B1 | 5/2001 | Parodi |
| 6,258,115 B1 | 7/2001 | Dubrul |
| 6,280,465 B1 | 8/2001 | Cryer |
| 6,306,145 B1 | 10/2001 | Leschinsky |
| 6,325,826 B1 | 12/2001 | Vardi et al. |
| 6,364,901 B1 * | 4/2002 | Inoue ............ 623/1.13 |
| 6,379,710 B1 | 4/2002 | Badylak |
| 6,383,213 B2 | 5/2002 | Wilson et al. |
| 6,409,750 B1 | 6/2002 | Hyodoh et al. |
| 6,440,161 B1 | 8/2002 | Madrid et al. |
| 6,471,722 B1 | 10/2002 | Inoue |
| 6,478,817 B2 | 11/2002 | Schmitt et al. |
| 6,508,835 B1 | 1/2003 | Shaolian et al. |
| 6,520,988 B1 | 2/2003 | Colombo et al. |
| 6,533,811 B1 * | 3/2003 | Ryan ............ A61F 2/07 606/194 |
| 6,551,350 B1 | 4/2003 | Thornton et al. |
| 6,558,396 B1 | 5/2003 | Inoue |
| 6,599,302 B2 | 7/2003 | Houser et al. |
| 6,613,072 B2 | 9/2003 | Lau et al. |
| 6,641,606 B2 | 11/2003 | Ouriel et al. |
| 6,673,107 B1 | 1/2004 | Brandt et al. |
| 6,682,536 B2 * | 1/2004 | Vardi ............ A61F 2/954 606/108 |
| 6,695,877 B2 | 2/2004 | Brucker et al. |
| 6,723,116 B2 * | 4/2004 | Taheri ............ A61B 17/00234 623/1.11 |
| 6,732,116 B2 | 5/2004 | Banerjee et al. |
| 6,733,522 B2 | 5/2004 | Schmitt et al. |
| 6,740,112 B2 | 5/2004 | Yodfat et al. |
| 6,749,628 B1 | 6/2004 | Callol et al. |
| 6,761,733 B2 | 7/2004 | Chobotov et al. |
| 6,761,734 B2 | 7/2004 | Suhr |
| 6,770,090 B2 | 8/2004 | Gantt et al. |

(56) References Cited

U.S. PATENT DOCUMENTS

| | | |
|---|---|---|
| 6,814,752 B1 | 11/2004 | Chuter |
| 6,824,558 B2 | 11/2004 | Parodi |
| 6,849,087 B1 * | 2/2005 | Chuter .................. 623/1.23 |
| 6,918,925 B2 | 7/2005 | Tehrani |
| 6,942,640 B2 | 9/2005 | Kokish |
| 6,945,990 B2 | 9/2005 | Greenan |
| 6,984,244 B2 | 1/2006 | Perez et al. |
| 7,014,653 B2 | 3/2006 | Ouriel et al. |
| 7,056,323 B2 | 6/2006 | Mareiro et al. |
| 7,070,613 B2 | 7/2006 | Weber et al. |
| 7,074,235 B1 | 7/2006 | Roy |
| 7,105,014 B2 | 9/2006 | Murray, III |
| 7,105,020 B2 | 9/2006 | Greenberg et al. |
| 7,122,052 B2 | 10/2006 | Greenhalgh |
| 7,144,421 B2 | 12/2006 | Carpenter et al. |
| 7,189,257 B2 | 3/2007 | Schmitt et al. |
| 7,294,147 B2 | 11/2007 | Hartley |
| 7,306,623 B2 | 12/2007 | Watson |
| 8,128,680 B2 | 3/2012 | Arnault De La Menardiere et al. |
| 9,956,102 B2 | 5/2018 | Arnault De La Menardiere et al. |
| 10,166,130 B2 | 1/2019 | LaDuca et al. |
| 10,179,058 B2 | 1/2019 | LaDuca et al. |
| 2001/0003161 A1 | 6/2001 | Vardi et al. |
| 2001/0016768 A1 | 8/2001 | Wilson et al. |
| 2001/0027338 A1 | 10/2001 | Greenberg |
| 2002/0156518 A1 | 10/2002 | Tehrani |
| 2003/0097170 A1 | 5/2003 | Friedrich et al. |
| 2003/0135257 A1 | 7/2003 | Taheri |
| 2003/0149466 A1 | 8/2003 | Gerberding |
| 2003/0220680 A1 | 11/2003 | Kashyap |
| 2003/0229389 A1 | 12/2003 | Escano |
| 2004/0098114 A1 | 5/2004 | Wilson et al. |
| 2004/0102838 A1 | 5/2004 | Killion et al. |
| 2004/0117003 A1 | 6/2004 | Ouriel et al. |
| 2004/0172121 A1 | 9/2004 | Eidenschink et al. |
| 2004/0215338 A1 | 10/2004 | Elkins et al. |
| 2004/0220660 A1 | 11/2004 | Shanley et al. |
| 2004/0225345 A1 | 11/2004 | Fischell et al. |
| 2004/0230287 A1 | 11/2004 | Hartley et al. |
| 2004/0243221 A1 | 12/2004 | Fawzi et al. |
| 2005/0010277 A1 | 1/2005 | Chuter |
| 2005/0033406 A1 | 2/2005 | Barnhart et al. |
| 2005/0043585 A1 | 2/2005 | Datta et al. |
| 2005/0049667 A1 | 3/2005 | Arbefeuille et al. |
| 2005/0049674 A1 | 3/2005 | Berra et al. |
| 2005/0085889 A1 | 4/2005 | Sundar |
| 2005/0085896 A1 | 4/2005 | Bonsignore et al. |
| 2005/0102018 A1 | 5/2005 | Carpenter et al. |
| 2005/0182476 A1 | 8/2005 | Hartley et al. |
| 2005/0228474 A1 | 10/2005 | Laguna |
| 2005/0246008 A1 | 11/2005 | Hogendijk et al. |
| 2005/0283220 A1 | 12/2005 | Gobran et al. |
| 2006/0129224 A1 | 6/2006 | Arbefeuille et al. |
| 2006/0142849 A1 | 6/2006 | Killion et al. |
| 2006/0155363 A1 | 7/2006 | LaDuca et al. |
| 2006/0229709 A1 | 10/2006 | Morris et al. |
| 2007/0055350 A1 | 3/2007 | Erickson et al. |
| 2007/0150051 A1 | 6/2007 | Arnault De La Menardiere et al. |
| 2007/0167955 A1 | 7/2007 | Arnault De La Menardiere et al. |
| 2007/0168020 A1 | 7/2007 | Brucker et al. |
| 2007/0179592 A1 | 8/2007 | Schaeffer |
| 2007/0219619 A1 | 9/2007 | Dieck et al. |
| 2008/0097404 A1 | 4/2008 | Yribarren et al. |
| 2009/0043373 A1 | 2/2009 | Arnault De La Menardiere et al. |
| 2009/0182405 A1 | 7/2009 | Arnault De La Menardiere et al. |
| 2012/0185036 A1 | 7/2012 | Arnault De La Menardiere et al. |
| 2019/0060096 A1 | 2/2019 | Arnault De La Menardiere et al. |
| 2019/0133797 A1 | 5/2019 | LaDuca et al. |

* cited by examiner

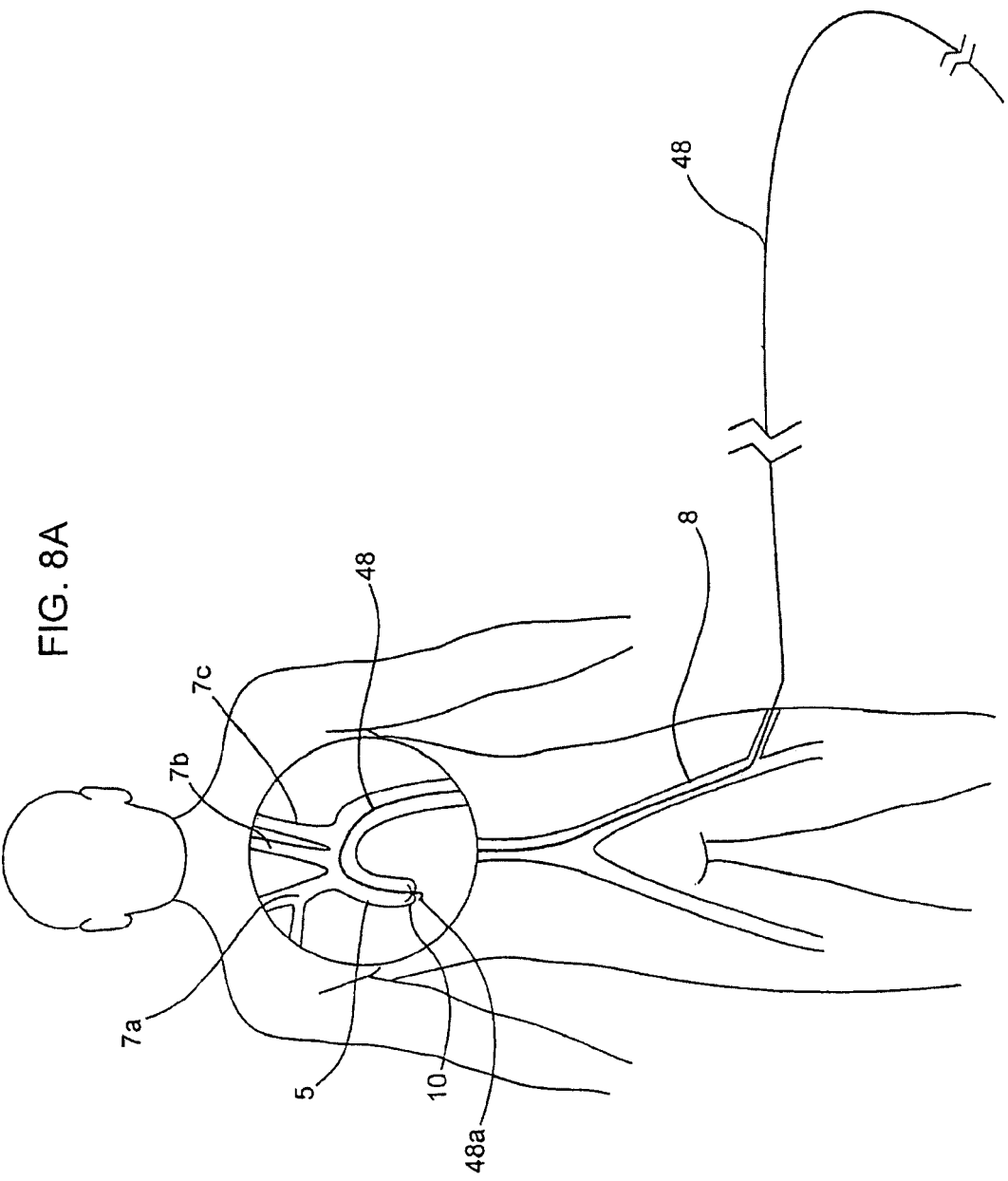

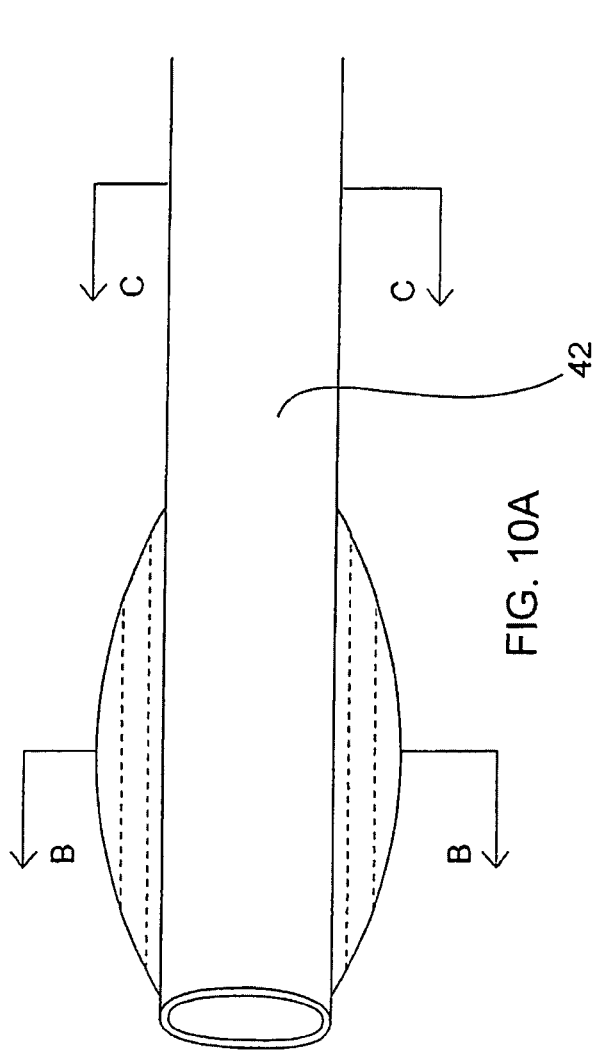
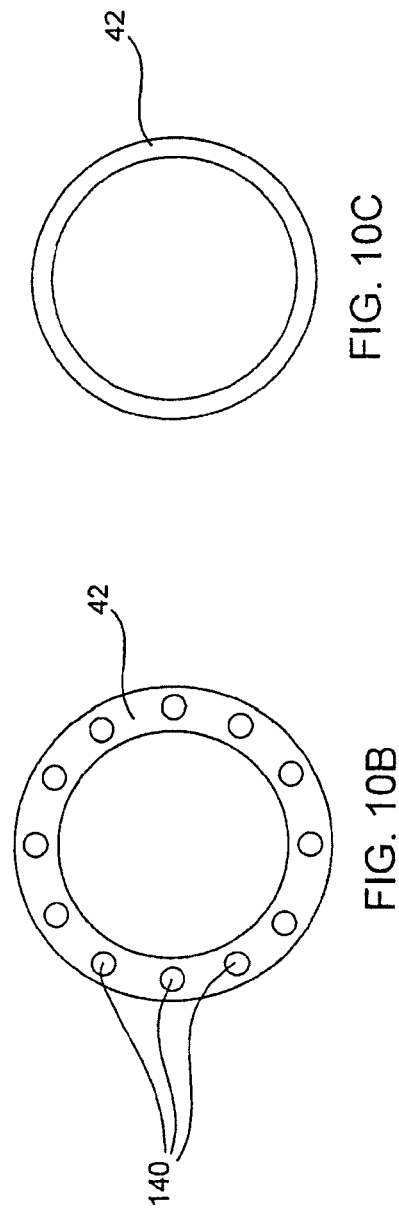

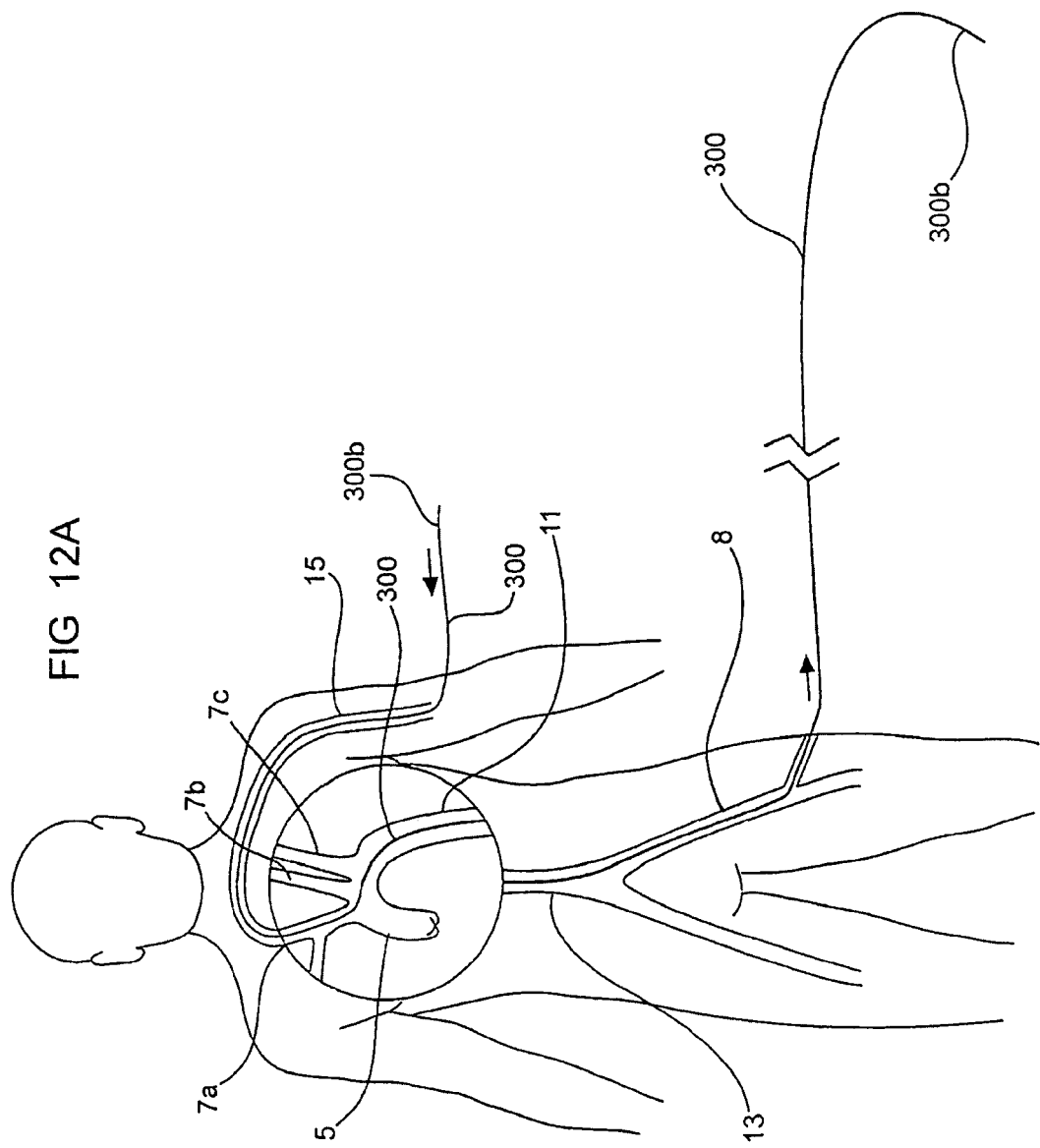

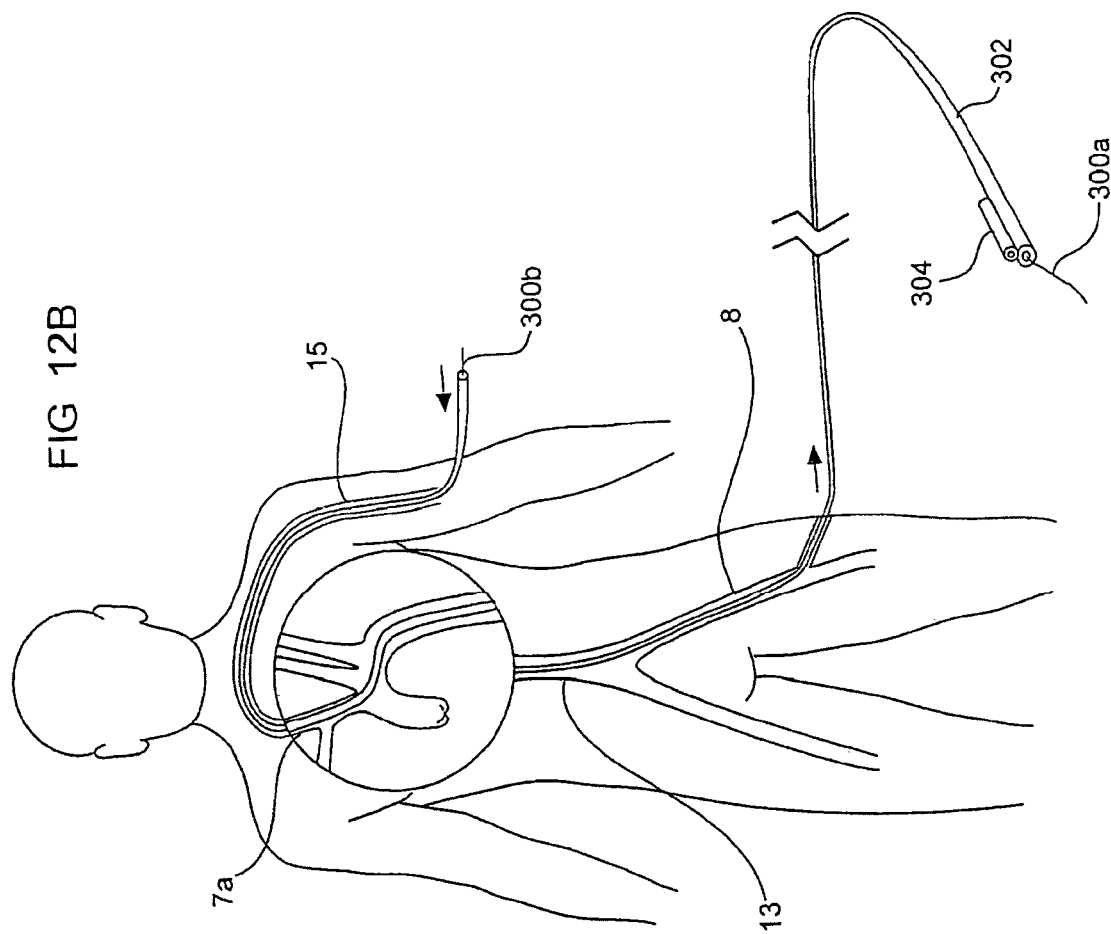

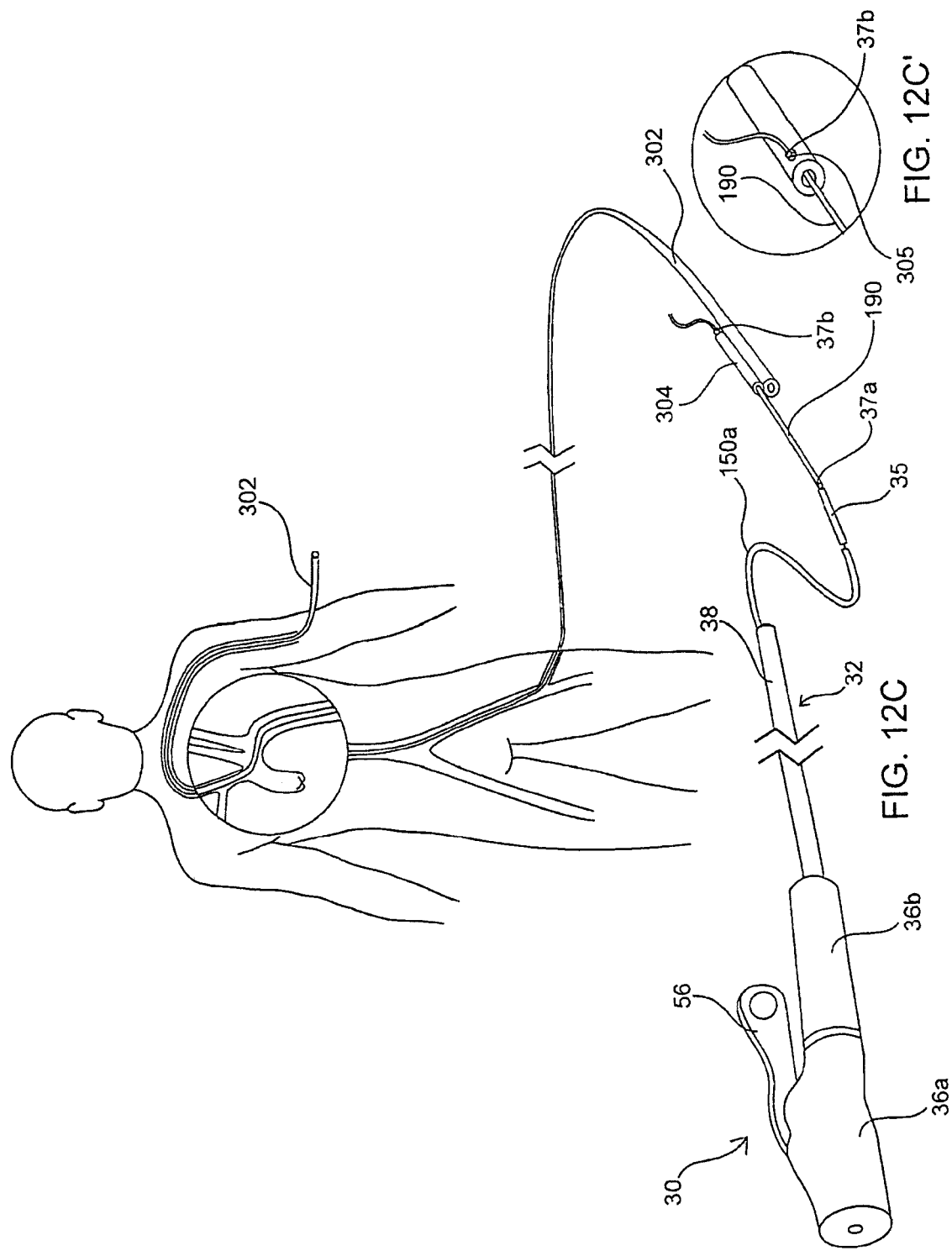

DELIVERY DEVICES FOR IMPLANTING DEVICES AT INTERSECTING LUMENS

CROSS-REFERENCE TO RELATED APPLICATIONS

This application is a divisional of U.S. patent application Ser. No. 11/241,242 filed Sep. 30, 2005, U.S. Pat. No. 8,287,583, which is a continuation-in-part of U.S. patent application Ser. No. 11/033,479 filed on Jan. 10, 2005, now abandoned; both applications are incorporated herein in their entirety.

FIELD OF THE INVENTION

The present invention relates to the treatment of vascular disease, including for example aneurysms, ruptures, psuedoaneurysms, dissections, exclusion of vulnerable plaque and treatment of occlusive conditions, and more particularly, the invention is related to an apparatus and method for delivering and deploying an implantable device within the body to treat such conditions. The present invention is particularly suitable for implanting stents, grafts and stent grafts within arteries or other vessels at sites involving two or more intersecting vessels.

BACKGROUND OF THE INVENTION

It is well known in the prior art to treat vascular disease with implantable stents and grafts. For example, it is well known in the art to interpose within a stenotic or occluded portion or an artery a stent capable of self-expanding or being balloon-expandable. Similarly, it is also well known in the prior art to use a graft or a stent graft to repair highly damaged or vulnerable portions of a vessel, particularly the aorta, thereby ensuring blood flow and reducing the risk of an aneurysm or rupture.

A more challenging situation occurs when it is desirable to use a stent, a graft or a stent graft at or around the intersection between a major artery (e.g., the abdominal aorta) and one or more intersecting arteries (e.g., the renal arteries). Use of single axial stents or grafts may effectively seal or block-off the blood flow to collateral organs such as the kidneys. U.S. Pat. No. 6,030,414 addresses such a situation, disclosing use of a stent graft having lateral openings for alignment with collateral blood flow passages extending from the primary: vessel into which the stent graft is positioned. The lateral openings are pre-positioned within the stent based on identification of the relative positioning of the lateral vessels with which they are to be aligned. U.S. Pat. No. 6,099,548 discloses a multi-branch graft and a system for deploying it. Implantation of the graft is quite involved, requiring a discrete, balloon-deployable stent for securing each side branch of the graft within a designated branch artery. Additionally, a plurality of stylets is necessary to deliver the graft, occupying space within the vasculature and thereby making the system less adaptable for implantation into smaller vessels. Further, delivery of the graft and the stents requires access and exposure to each of the branch vessels into which the graft is to be placed by way of a secondary arteriotomy. These techniques, while effective, may be cumbersome and somewhat difficult to employ and execute, particularly where the implant site involves two or more vessels intersecting the primary vessel, all of which require engrafting.

The use of bifurcated stents for treating abdominal aortic aneurysms (AAA) is well known in the art. These stents have been developed specifically to address the problems that arise in the treatment of stenoses at or near the site of a bifurcation. The bifurcated stent is typically configured in a "pant" design which comprises a tubular body or trunk and two tubular legs. Examples of bifurcated stents are provided in U.S. Pat. Nos. 5,723,004 and 5,755,735. Bifurcated stents may have either unitary or modular configurations in which the components of the stent are interconnected in situ. In particular, one or both of the leg extensions are attachable to a main tubular body. Although the delivery of modular systems is less difficult due to the smaller sizes of the components, it is difficult to align and interconnect the legs with the body lumen with enough precision to avoid an) leakage. On the other hand, while unitary, stents reduce the probability of leakage, their larger structure is often difficult to deliver to a treatment site having a constrained geometry.

While the conventional bifurcated stents have been used somewhat successfully in treating AAAs, they are not adaptable where the implant site is within the aortic arch. The arch region of the aorta is subject to very high blood flow and pressures which make it difficult to position a stent graft without stopping the heart and placing the patient on cardiopulmonary bypass. Moreover, even if the stent graft is able to be properly placed, it must be able to be secured in a manlier to endure the constant high blood flow, pressures, and shear forces it is subjected to over time in order to prevent it from migrating or leaking. Additionally, the aorta undergoes relatively significant changes (of about 7%) in its diameter due to vasodilation and vasorestriction. As such, if an aortic arch graft is not able to expand and contract to accommodate such changes, there may be an insufficient seal between the graft and the aortic wall, subjecting it to a risk of migration and/or leakage. Further, the complexity (e.g., highly curved) and variability of the anatomy of the aortic arch from person to person makes it a difficult location in which to place a stent graft. While the number of branch vessels originating from the arch is most commonly three, namely, the left subclavian artery, the left common carotid artery and the innominate artery, in some patients the number of branch vessels may be one, more commonly two and in some cases four, five or even six. Moreover, the spacing and angular orientation between the tributary, vessels are variable from person to person.

In order to achieve alignment of a side branch stent or a lateral opening of the main stent with a branch vessel, a custom stent designed and manufactured according to each patient's unique geometrical constraints would be required. The measurements required to create a custom manufactured stent to fit the patient's unique vascular anatomy could be obtained using spiral tomography, computed tomography (CT), fluoroscopy, or other vascular imaging system. However, while such measurements and the associated manufacture of such a custom stent could be accomplished, it would be time consuming and expensive. Furthermore, for those patients who require immediate intervention involving the use of a stent, such a customized stent is impractical. In these situations it would be highly desirable to have a stent which is capable of adjustability in situ while being placed. It would likewise be highly desirable to have the degree of adjustability sufficient to allow for a discrete number of stents to be manufactured in advance and available to accommodate the required range of sizes and configurations encountered.

Another disadvantage of conventional stents and stent grafts is the limitations in adjusting the position of or subsequently retrieving the stent or stent-graft once it has been deployed. Often, while the stent is being deployed, the final location of the delivered stent is determined not to be optimal for achieving the desired therapeutic effect. During deployment of self-expanding stents, the mode of deployment is either to push the stent out of a delivery catheter, or more commonly to retract an outer sheath while holding the stent in a fixed location relative to the vasculature. In either case the distal end of the stent is not attached to the catheter and, as such, is able to freely expand to its maximum diameter and seal with the surrounding artery wall. While this self-expanding capability is advantageous in deploying the stent, it presents the user with a disadvantage when desiring to remove or reposition the stent. Some designs utilize a trigger wire(s) to retain the distal end of the stent selectively until such time as full deployment is desired and accomplished by releasing the "trigger" wire or tether wire(s). The limitation of this design is the lack of ability to reduce the diameter of the entire length of stent by stretching the stent which is pursed down on the distal end by the trigger wire. The significance of reducing the diameter of the stent while positioning and determining if it should be released from the tether wire is that the blood flow is occluded by, the fully expanded main body of the stent even while the distal end is held from opening by the tether wire.

Another disadvantage of conventional stent-grafts is the temporary, disruption in blood flow through the vessel. In the case of balloon deployable stents and stent-grafts, expansion of the balloon itself while deploying the stent or stent-graft causes disruption of blood flow through the vessel. Moreover, in certain applications, a separate balloon is used at a location distal to the distal end of the stent delivery catheter to actively block blood flow while the stent is being placed. In the case of self-expanding stent-grafts, the misplacement of a stent graft may be due to disruption of the arterial flow during deployment, requiring the placement of an additional stent-graft in an overlapping fashion to complete the repair of the vessel. Even without disruptions in flow, the strong momentum of the arterial blood flow can cause a partially opened stent-graft to be pushed downstream by the high-pressure pulsatile impact force of the blood entering the partially deployed stent graft.

Attempts have been made to address some of the above-described disadvantages of conventional stents and stent grafts. For example, U.S. Pat. No. 6,099,548 discloses the use of strings passed through and attached to the distal end of the stent which is inserted through a first opening in the vasculature. The string ends are then passed through a second opening in the vasculature such that they can be pulled, thereby moving the stent within the vasculature. While the use of attached strings provides some additional control of the stent's placement, one skilled in the art can appreciate that passing strings from within the vasculature through a second opening presents procedural difficulties. Moreover, it is advantageous to the welfare of the patient to minimize the number of surgical openings when performing any procedure.

With the limitations of current stent grafts and stent graft placement technologies, there is clearly a need for an improved means and method for implanting a stent or graft and for treating vascular disease and conditions affecting interconnecting vessels (i.e., vascular trees) which address the drawbacks of the prior art.

SUMMARY OF THE INVENTION

The present invention provides implantable devices and systems and methods for deploying the implantable devices within the body, as well as methods of manufacturing the implantable devices.

The implantable devices of the present invention include at least a main lumen having a proximal end and a distal end, but often includes at least one side branch lumen to address implant sites having interconnecting vessels. The devices, particularly in the form of stents, grafts and stent grafts, are made of interconnected cells which may be selectively manipulated to adjust the length and diameter of the main and side branch lumens of the devices. As such, a feature of the present invention is the provision of a variable or adjustable stent, grafts or stent graft that is able to address inconsistent or patient-to-patient variabilities in tortuous vascular anatomies, e.g., to accommodate variability in the spacing between or the angular orientation of the tributary vessels of the aortic arch.

The systems of the present invention are particularly suitable for delivering and deploying the subject stent, graft or stent graft devices within a vessel or tubular structure within the body particularly where the implant site involves two or more interconnecting vessels. In general, the deliver and deployment system of the present invention utilizes at least one elongated member or string and in many embodiments a plurality of elongated members or strings which are releasably attached to the luminal ends of the implantable device. A single string or a set of attachment strings is provided for each of the proximal and distal ends of the main lumen of the device and an additional string or set of strings is provided for each side branch lumen. The system includes means for selectively tensioning each of the single or plurality of attachment strings whereby the device is selectively; deployable by releasing the tension on the attachment strings. The delivery system controls the adjustment of spacing between the various lumens and their respective angular radial orientation with respect to the main lumen to be varied in situ during placement of the implant at the target location. There may be other means equally suitable for selective deployment of the stent beyond the use of detachable strings. For example, similar to the use of detachable coils used in aneurysm repair, a current may be used to erode by electrolysis the connection point to the stent ends. In other words, the implantable device may be partially deployable, where the entirety of the device is exposed or partially exposed from the deliver system, which is most commonly in the form of a collection of nested catheters and lumens. Each luminal end of the implantable device may be individually deployed as desired, where some or all of the luminal ends may be simultaneously deployed or they may be serially deployed in an order that best facilitates the implantation procedure.

The implant delivery and deployment system in one embodiment includes a series of guidewires, a distal catheter portion and a proximal handle portion where the implantable device is loaded within the catheter portion prior to deliver to the target site. At least the catheter portion of the system is tracked over the one or more guidewires which direct and position the stent or stent-graft and each of its branches within their respective targeted vessels selected for implantation. Various controls are provided for the selective tensioning and release of the implant's luminal ends, where the controls may be located on the handle portion, the catheter portion or both. In a preferred embodiment, the catheter portion and/or the deliver, guidewires are articulatable at their distal ends to facilitate navigation through the vasculature.

One embodiment of the system includes an articulating delivery guidewire or guiding catheter. The articulating guidewire may have one or more articulation points to allow an operator to change the shape of the distal portion of the guidewire by manipulation of the proximal portion of the guidewire. The guidewire can be preconfigured to change from a straight configuration into a range of various preselected shapes brought about by controlling individual articulation points during manipulation of the proximal portion of the guidewire. In this way, a guidewire may be produced to unique specifications for access to distinct areas of the vasculature. For example, this may be of particular importance in locating the implant within a region that requires an "S" shaped path from entry point to implant target site. Introduction of a guidewire through a femoral artery access point leading to an implant target in the innominate artery exemplifies one instance of a potentially difficult "S" shaped navigation pathway where such an articulating guidewire may be advantageous.

The methods of the present invention involve deploying the implantable device where certain of the methods involve the use of the subject systems. Methods for manufacturing the implantable devices are also provided.

Another objective of the invention is to provide a method of stent deployment which does not cause temporary occlusion of the vessel into which stent is to be placed.

Another objective of the invention is to provide a method of stent deployment using guidewires and an associated delivery system which enter the vasculature from a single access location.

An advantage of the stent delivery, system of the present invention is that it does not require the use of space-occupying stylets and balloon catheters.

Another advantage of the subject system is that it allows for adjustment of the position or placement, as well as removal, of a stent during and after deployment thereof.

The present invention is additionally advantageous in that it provides a user with the ability to deploy a stent, to evaluate the suitability of the resulting deployment using standard imaging, such as by use of radiographic dye and fluoroscopy or any other imaging system, to check for endoleak between the covered stent wall and the surrounding arterial wall and to detach the stent from the delivery system upon adequate stent deployment or, in the case of an inadequate deployment, to either relocate the stent to a new location and obtain a satisfactory result by controlling the delivery and detachment of the stent in a repeatable manner, or to remove the stent entirely.

The present invention is additionally advantageous in that it secures the stent from migration within the vasculature by integrating the cells of the side branch lumen into the cells of the main body lumen such that, when the side branch lumens are deployed within their branch vessels, the main body lumen is constrained from migration by a "lock and key" mechanism. More specifically, the interconnection of the side branch lumen to the main body lumen is accomplished by forming the side branch lumen and the main body lumen from the same single wire where a specific wire wrap pattern is used to form a linking mesh to integrate the side branch lumen with the main lumen. Thus, when the side branch is deployed within and held in place by the side branch artery, the main body of the stent cannot migrate. Moreover, such a "passive" anchoring mechanism is atraumatic, as opposed to an active anchoring means, such as barbs or hooks, which may damage the cellular structures of the implant site leading to smooth muscle proliferation, restenosis, and other vascular complications.

These aid other objects, advantages, and features of the invention will become apparent to those persons skilled in the art upon reading the details of the invention as more fully described below.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Also for purposes of clarity, certain features of the invention may not be depicted in some of the drawings. Included in the drawings are the following figures:

FIGS. 8A-8H illustrate various steps of a method of the present invention for delivering a stent of the present invention using an implantation system of the present invention.

FIG. 10A illustrates a side view of an embodiment of an inner member of the catheter portion of the delivery and deployment system of the present invention. FIG. 10B illustrates a cross-sectional view of the inner member of FIG. 10A taken along the line B-B of FIG. 10A. FIG. 10C illustrates a cross-sectional view of the inner member of FIG. 10 taken along the line C-C of FIG. 10A.

FIGS. 12A-12F illustrate various steps of another method of the present invention for delivering a stent of the present invention using an implantation system of the present invention.

DETAILED DESCRIPTION OF THE INVENTION

Figure 1A:
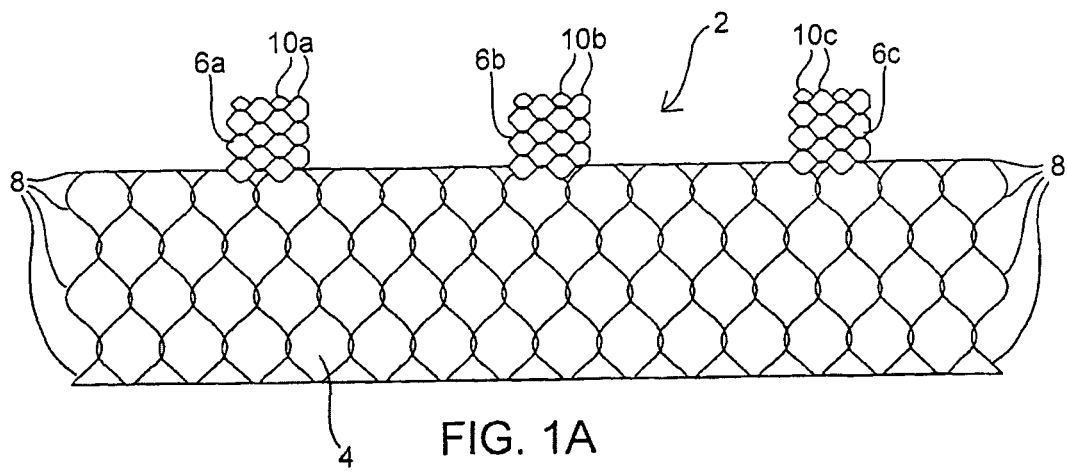
FIG. 1A illustrates an embodiment of an implant of the present invention in a natural, deployed state.

Before the devices, systems and methods of the present invention are described, it is to be understood that this invention is not limited to particular therapeutic applications and implant sites described, as such may vary. It is also to be understood that the terminology used herein is for the purpose of describing particular embodiments only, and is not intended to be limiting, since the scope of the present invention will be limited only by the appended claims.

Unless defined otherwise, all technical aid scientific terms used herein have the same meaning as commonly understood by one of ordinary skill in the art to which this invention belongs. The terms "proximal" and "distal" when used to refer to the delivery and deployment systems of the present invention are to be understood to indicate positions or locations relative to the user where proximal refers to a position or location closer to the user and distal refers to a position or location farther away from the user. When used with reference to the implantable devices of the present invention, these terms are to be understood to indicate positions or locations relative to a delivery and deployment system when the implantable devices is operatively positioned within the system. As such, proximal refers to a position or location closer to the proximal end of the delivery and deployment system and distal refers to a position or location closer to the distal end of the delivery and deployment system. The term "implant" or "implantable device" as used herein includes but is not limited to a device comprising a stent, a graft, a stent-graft or the like.

It must be noted that as used herein and in the appended claims, the singular forms "a", "an", and "the" include plural referents unless the context clearly dictates otherwise. Thus, for example, reference to "a string" may include a plurality of such strings and reference to "the tubular member" includes reference to one or more tubular members and equivalents thereof known to those skilled in the art, and so forth.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The present invention will now be described in greater detail by way of the following description of exemplary embodiments and variations of the devices, systems and methods of the present invention. The invention generally includes an implantable device which includes a tubular member in the form of a stent, a graft or a stent graft, where the device may further include one or more branching or transverse tubular members laterally extending from the main or primary tubular member. The invention further includes a system for the percutaneous, endovascular deliver, and deployment of the implantable device at a target implant site within the body. The implant site may be any tubular or hollow tissue lumen or organ; however, the most typical implant sites are vascular structures, particularly the aorta. A feature of the invention is that it addresses applications involving two or more intersecting tubular structures and, as such, is particularly suitable in the context of treating vascular trees such as the aortic arch and the infrarenal aorta.

Implantable Devices of the Present Invention

Figure 1B:
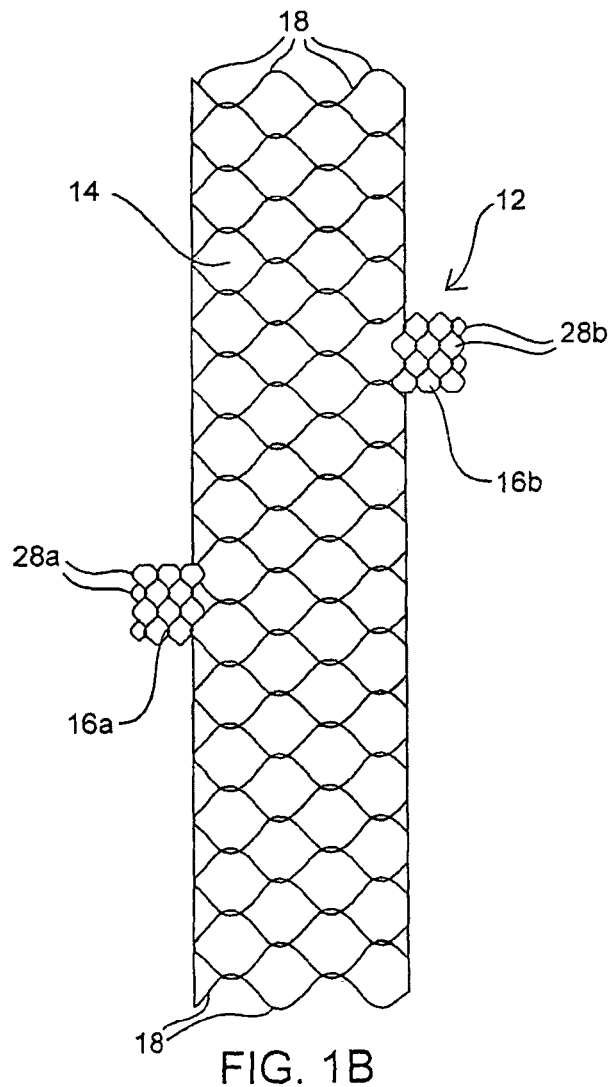
FIG. 1B illustrates another embodiment of an implant of the present invention in a natural, deployed state.

Referring now to the figures and to FIGS. 1A and 1B in particular, there are illustrated exemplary embodiments of implantable devices of the present invention. Each of the devices has a primary or main tubular member and at least one laterally extending tubular branch, however, the implantable devices of the present invention need not have side branches.

FIG. 1A illustrates one variation of an implantable device 2 having a primary tubular portion, body or member 4 and laterally extending side branches 6a, 6b and 6c, interconnected and in fluid communication with main body 4 by way, of lateral openings within the body. The proximal and distal ends of the main tubular member 4 terminate in crowns or apexes 8, the number of which may vary. The distal ends of the side branches 6a, 6b and 6c terminate in crowns or apexes 10a, 10b and 10c, respectively, the number of which may also vary. Device 2 is particularly configured for implantation in the aortic arch where primary tubular member 4 is positionable within the arch walls and tubular branches 6a, 6b and 6c are positionable within the innominate artery, the left common carotid artery; and the left subclavian artery, respectively.

As will be described in greater detail below, the deployment or attachment members of the subject delivery and deployment systems, are looped through the apexes 10a, 10b and 10c, or through eyelets (not shown) extending from the distal ends of the apexes of the device 2. The attachment members of the present invention may be any elongated member including but not limited any strings, filaments, fibers, wires, stranded cables, tubings or other elongated member which are releasably attachable to the distal ends of the various lumens of the stent. Means of releasable attachment include but are not limited to electrolitic erosion, thermal energy, magnetic means, chemical means, mechanical means or any other controllable detachment means.

FIG. 1B illustrates another variation of a device 12 having a primary tubular portion or member 14 and laterally extending branches 16a and 16b, interconnected and in fluid communication with main body 14 by way of lateral openings within the body. The proximal and distal ends of the main tubular member 14 terminate in crowns or apexes 18 which are employed as described above with respect to FIG. 1A while the distal ends of the side branches 16a and 16b terminate in crowns or apexes 28a and 18b, respectively. Device 12 is particularly configured for implantation in the infra-renal aorta where primary tubular member 14 is positionable within the walls of the aorta and tubular branches 16a and 16b are positioned within the right and left renal arteries, respectively.

Those skilled in the art will recognize that the subject implants may have any number and configuration of lumens (e.g., a single main lumen without side branch lumens, a main lumen and one or more side branch lumens) where the one or more side branch lumens may be positioned at any appropriate location along the length of the main lumen and at any angle with respect to the longitudinal axis of the main lumen, and where the there are two or more side branch lumens, the lumens mats be spaced axially and circumferentially angled relative to each other to accommodate the target vasculature into which the implant is to be placed. Additionally, the length, diameter and shape (e.g., radius of curvature) of each of the implant's lumens may vary as needed to accommodate the vessel into which it is positioned. The various structural and functional aspects of the inventive implants are discussed in greater detail below.

Figure 1C:
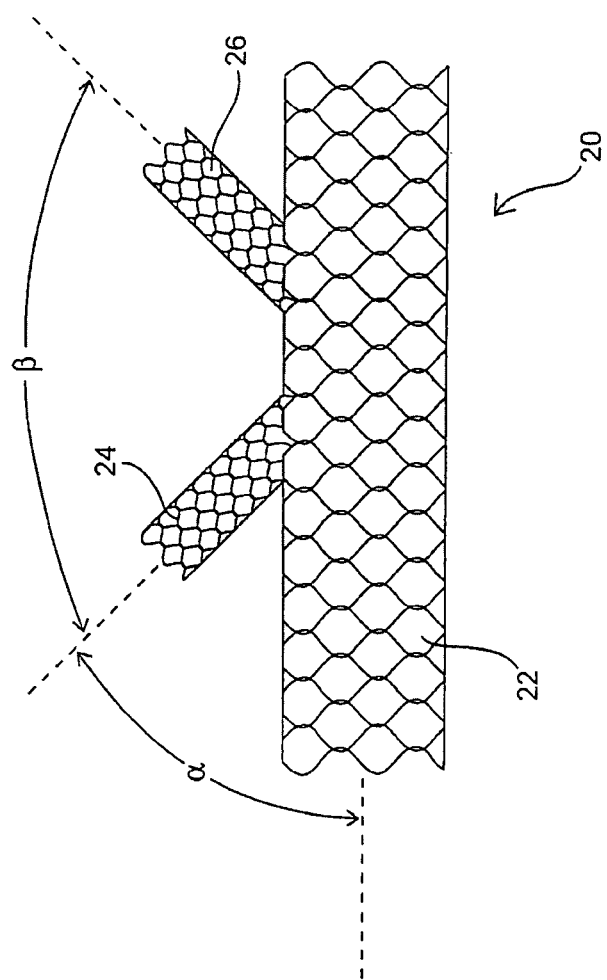
FIG. 1C illustrates another embodiment of an implant in which the side branch lumens are angled.
Figure 1D:
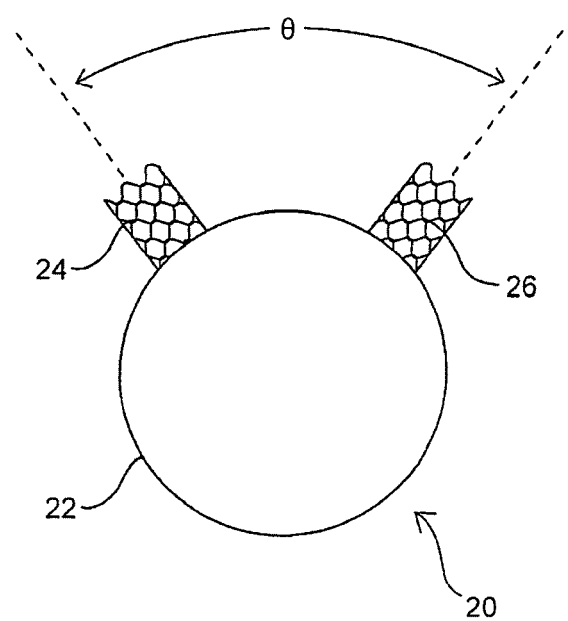
FIG. 1D illustrates an end view of the implant of FIG. 1C.
Figure 1E:
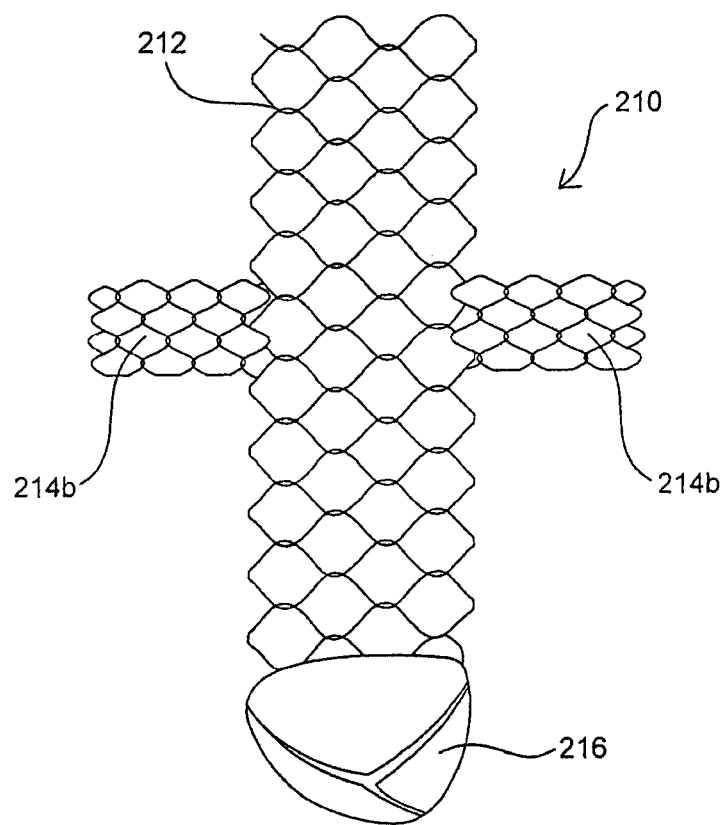
FIG. 1E illustrates another embodiment of an implant of the present invention having a cardiac valve operatively coupled to it.

It is also contemplated that therapeutic or diagnostic components or devices may be integrated with the subject implants. Such devices mats include but are not limited to prosthetic valves, such as cardiac valves (e.g., an aortic or pulmonary valve) and venous valves, sensors to measure flow, pressure, oxygen concentration, glucose concentration, etc., electrical pacing leads, etc. For example, as illustrated in FIG. 1E, an implant 210 for treating the aortic root is provide which includes a mechanical or biological prosthetic valve 216 employed at a distal end of the main lumen 212. Device 210 further includes two smaller, generally opposing side branch lumens 214a and 214b adjustably aligned for placement within the right and left coronary ostia, respectively. The length of the stent graft may be selected to extend to a selected distance where it terminates at any location prior to, within or subsequent to the aortic arch, e.g., it may extend into the descending aorta. Any number of additional side branches may be provided for accommodating the aortic arch branch vessels.

Those skilled in the art will appreciate that any suitable stent or graft configuration may be provided to treat other applications at other vascular locations at or near the intersection of two or more vessels (e.g., bifurcated, trifurcated, quadrificated, etc.) including, but not limited to, the aorto-illiac junction the femoral-popiteal junction, the brachycephalic arteries, the posterior spinal arteries, coronary bifurcations, the carotid arteries, the superior and inferior mesenteric arteries, general bowel and stomach arteries, cranial arteries and neurovascular bifurcations.

As mentioned above, the implantable devices of the present invention may include a stent or a graft or a combination of the two, referred to as a stent graft, a stented graft or a grafted stent. The stents and grafts of the present invention may be made of any suitable materials known in the art. Preferably, the stent is constructed of wire, although any suitable material may be substituted. The retire stent should be malleable, for example, the stent may be made of tungsten, platinum or nitinol but any other suitable materials may be used instead of or in addition to these commonly used materials.

The stents may have any suitable wire form pattern or may be cut from a tube or flat sheet. In one embodiment, the entire stent structure is fabricated from a single wire woven into a pattern of interconnected cells forming, for example, a closed chain link configuration. The structure may have a straight cylindrical configuration, a curved tubular configuration, a tapered hollow configuration, have asymmetrical cell sizes, e.g., cell size may along the length or about the circumference of the stent. The ends of the main stent lumen and/or the end of one or more side branch stent lumens may, be flared. The struts of the stent (i.e. the elemental portions that form a cell) may vary in diameter (in wire embodiments) or thickness or width (in sheet and cut tube embodiments).

In one particular embodiment, the stent is configured from a single-wire. The single-wire stent configuration is advantageous in that through selective interlacing of the connection points along the length of the stent, it provides for adjustability in the angular orientation of the side branch stents relative to each other and relative to the main stent lumen within a selected range that can accommodate any possible variation in the anatomy being treated. Such angular orientation of the side branch lumens may be axial, circumferential or both. FIG. 1C illustrates an implant device 20 in which side branch lumens 24 and 26 each has an angular orientation, defined by angle $\alpha$, with respect to main lumen 22, and have an angular orientation, defined by angle $\beta$, with respect to each other. FIG. 1D is an end view of implant device 20 which illustrates the circumferential orientation, defined by angle $\theta$, between side branch lumens 22 and 24. Typical ranges of the various angles are as follows: from about 10° to about 170° for angle $\alpha$, from 0° to about 170° for angle $\beta$, and from 0° to 360° for angle $\theta$. These orientations mat, be provided by the fabrication process resulting in a stent which has naturally biased orientations in an unconstrained, pre-deployed condition, i.e., the neutral state. One or more of these orientations ma) be selectively adjusted within the angle ranges provided above upon delivery and placement of the branch lumens within the respective vessel lumens. This design also allows for adjustability in the linear spacing between the side branch stents by stretching and/or foreshortening of the main lumen of the stent. Further, the side branch portions can be elongated to allow for placement of an oversized stent in a smaller branch vessel thereby providing adequate apposition between the stent and the vessel wall. It should be noted that the adjustability of the stent does not compromise the radial force needed to fixate or anchor and prevent migration and endoleak of the stent and/or stent-graft.

The graft portion of a stent graft may be made from a textile, polymer, latex, silicone latex, polytetraflouroethylene, polyethylene, Dacron polyesters, polyurethane or other or suitable material such as biological tissue. Biological tissues that may be used include, but are not limited to, extracellular matrices (ECMs), imibilical cord tissue and collagen. Extracellular matrices suitable for use with the present invention include mammalian intestinal, stomach, bladder submucosa, dennis or liver basement membranes derived from sheep, bovine, porcine or any suitable mammal. The graft material must be flexible and durable in order to withstand the effects of installation and usage. One of skill in the art would realize that grafts of the subject invention may be formulated by many different well known methods such as for example, by weaving or formed by dipping a substrate in the desired material.

The stent may be coated with or anchored mechanically to the graft, for example, by physical or mechanical means (e.g., screws, cements, fasteners, such as sutures or staples) or by friction. Further, mechanical attachment means may be employed to effect attachment to the implant site by including in the design of the stent a means for fastening it into the surrounding tissue. For example, the device may include metallic spikes, anchors, hooks, barbs, pins, clamps, or a flange or lip to hold the stent in place.

The stent may be processed in such a way as to adhere a covering, such as made of an ECM material, to only the wire, and not extend between wire segments or within the stent cells. For instance, one could apply current or heat to the wire stent structure while the ECM has been put in contact with the underlying structure. Just as when cooking meat on a hot pan leaves tissue, the ECM could be applied to the stent in such a manner.

The subject stents, grafts and/or stent grafts may be coated in order to provide for local delivery, of a therapeutic or pharmaceutical to the disease site. Local delivery requires smaller dosages of therapeutic or pharmaceutical delivered to a concentrated area: in contrast to systemic dosages which require multiple administrations and loss of material before reaching the targeted disease site.

The subject stents, grafts and/or stent grafts are coated by applying a primer layer onto its surface. The primer layer formulates a reservoir for containing the therapeutic/pharmaceutical. The overlapping region between the primer layer and active ingredient may be modified to increase the permeability of the primer layer to the active ingredient. For example, by applying a common solvent, the active ingredient and the surface layer mix together and the active ingredient gets absorbed into the primer layer. In addition, the primer layer may also be treated to produce an uneven or roughened surface. This rough area entraps the active ingredient and enhances the diffusion rate of the ingredient when the stent is inserted into the patient's body. As such, the implant has die ability to diffuse drugs or other agents at a controllable rate. Furthermore, one of skill in the art would understand that the subject invention may provide a combination of multiple coatings, such as the primer lay may be divided into multiple regions, each containing a different active ingredient.

The subject stents, grafts and/or stent grafts may be coated with any therapeutic material, composition or drug, including but not limited to dexamethasone, tocopherol, dexamethasone phosphate, aspirin, heparin, coumadin, urokinase, streptokinase and TPA, or any other suitable thrombolytic substance to prevent thrombosis at the implant site. Further therapeutic and pharmacological agents include but are not limited to proliferative/antimitotic agents paclitaxel, epidipodophyllotoxins, antibiotics, anthracyclines, mitoxantrone, bleomycins, plicamycin, and mitomycin, enzymes, anti-platelet agents, non-steroidal agents, heteroaryl acetic acids, gold compounds, immunosuppressives, angiogenic agents, nitric oxide donors, antisense oligonucleotides, cell cycle inhibitors, and protease inhibitors.

The subject implants may also be seeded with cells of any type including stem cells, to promote angiogenesis between the implant and the arterial walls. Methods have included applying a porous coating to the device which allows tissue growth into the interstices of the implant surface. Other efforts at improving host tissue in growth capability and adhesion of the implant to the host tissue have involved including an electrically charged or ionic material in the tissue-contacting surface of the device. As mentioned earlier, the subject stents and grafts may also be provided with a covering or otherwise be implanted or embedded with or be completely fabricated from an extracellular matrix (ECM) material. Suitable ECM materials are derived from mammalian hosts sources and include but are not limited to small intestine submucosa, liver basement membrane, urinary bladder submucosa, stomach submucosa, the dermis, etc. Other examples of ECM material includes but is not limited to fibronectin, fibrin, fibrinogen, collagen, including fibrillar and non-fibrillar collagen, adhesive glycoproteins, proteoglycans, hyaluronan, secreted protein acidic and rich in cysteine (SPARC), thrombospondins, tenacin, and cell adhesion molecules, and matrix metalloproteinase inhibitors.

The ECM portion of the implant is eventually resorbed by the surrounding tissue, taking on the cellular characteristics of the tissue, e.g., endothelium, smooth muscle, adventicia, into which it has been resorbed. Still yet, an ECM scaffolding having a selected configuration may be operatively attached to a stent or stent graft of the present invention at a selected location whereby the ECM material undergoes subsequent remodeling to native tissue structures at the selected location. For example, the ECM scaffolding may be positioned at the annulus of a previously removed natural aortic valve configured in such a way 7 as to create the structural characteristics of aortic valve leaflets and whereby the implant provides valve function.

The stent, graft, or stent graft of the present invention may also include a sensor or sensors to monitor pressure, flow, velocity, turbidity, and other physiological parameters as well as the concentration of a chemical species such as for example, glucose levels, pH, sugar, blood oxygen, glucose, moisture, radiation, chemical, ionic, enzymatic, and oxygen. The sensor should be designed to minimize the risk of thrombosis and embolization. Therefore, slowing or stoppage of blood flow at any point within the lumen must be minimized. The sensor may be directly attached to the outer surface or may be included within a packet or secured within the material of the stent, graft, or stent graft of the present invention. The biosensor may further employ a wireless means to deliver information from the implantation site to an instrument external to the body.

The stent, graft or stent graft may be made of visualization materials or be configured to include marking elements, which provide an indication of the orientation of the device to facilitate proper alignment of the stent at the implant site. Any suitable material capable of imparting radio-opacity may be used, including, but not limited to, barium sulfate, bismuth trioxide, iodine, iodide, titanium oxide, zirconium oxide, metals such as gold, platinum, silver, tantalum, niobium, stainless steel, and combinations thereof. The entire stent or any portion thereof may be made of or marked with a radiopaque material, i.e., the crowns of the stent.

Device Fabrication Methods

Figure 13A:
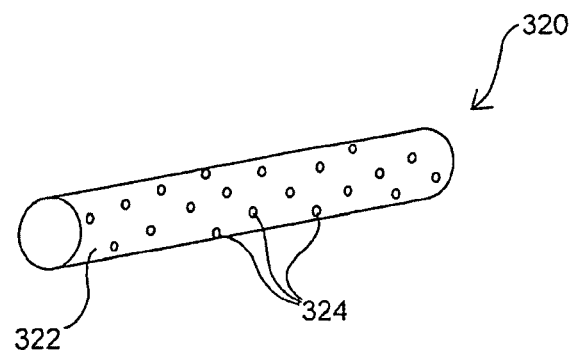
FIGS. 13A-13C illustrate various exemplary mandrel designs for fabricating the stents and stent grafts of the present invention.
Figure 13B:
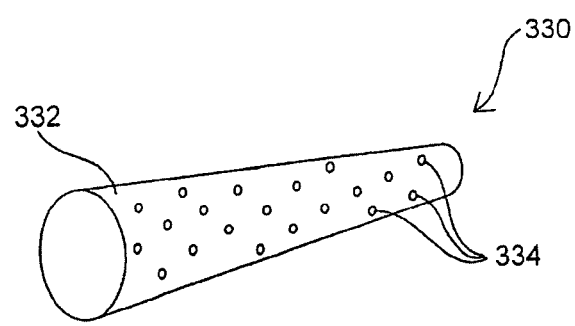
Figure 13C:
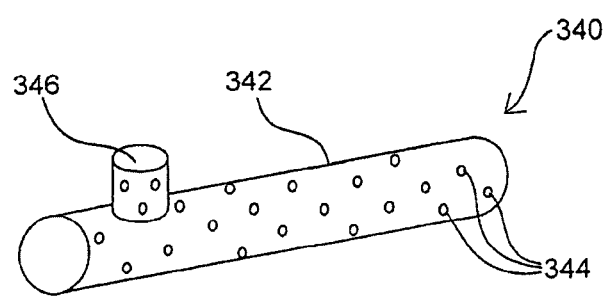

The stent of the present invention mats be fabricated in many watts. One method of making the stent is by use of a mandrel device such as the mandrel devices 320, 330 and 340 illustrated in FIGS. 13A-13C, respectively. Each of the devices has at least a main mandrel component 322, 332 and 342, respectively, with a plurality of selectively positioned pinholes 324, 334 and 344, respectively, within which a plurality of pins (not shown) are selectively positioned, or from which a plurality of pins is caused to extend. As is described in more detail below, the stent structure is formed by selectively wrapping a wire around the pins. Where the stent is to have one or more side branch lumens, the mandrel device, such as device 340, may be provided with at least one side mandrel 346 extending substantially transverse to the main mandrel 342, where the number of side mandrels preferably corresponds to the number of stent side branches to be formed. The mandrel devices may be modular where side branch mandrels of varying diameters and lengths can be detachably assembled to the main mandrel. The configuration of the main mandrel as well as the side branch mandrel(s) may have any suitable shape, size, length, diameter, etc. to form the desired stent configuration. Commonly, the mandrel components have a straight cylindrical configuration (see FIGS. 13A and 13C) having a uniform cross-section, but may be conical with varying diameters along a length dimension (see FIG. 13B), frustum conical, have an oval cross-section, a curved shape, etc.

The pins may be permanently affixed to the mandrel components or are themselves removable from and selectively positionable within holes formed in the mandrel components. Still let, the mandrel device may be configured to selectively extend and retract the pins. The number of pins and the distance and spacing between them mats be varied to provide a customized pin configuration. This customization enables the fabrication of stents having varying sizes, lengths, cell sizes, etc. using a limited number of mandrel components. For example, in one variation, the pins are arranged about the mandrel components in an alternating pattern such as for example, where four out of eight pin holes per row will be filled with pins. Alternatively, a selection of mandrels may be provided, each having a unique pinhole pattern which in turn defines a unique stent cell pattern.

To form the stent, a shape memory wire, such as a NITINOL wire, having a selected length and diameter are provided. Typically, the length of the wire ranges from about 9 to about 12 feet long, but may be longer if needed or shorter if more practical. The wire's diameter is typically in the range from about 0.004 to about 0.020 inch. After providing a mandrel device having winding pins at the desired points or locations on the mandrel components, the wire is wound about the pins in a selected direction and in a selected over-and-under lapping pattern, e.g., a zigzag pattern, to form a series of interconnected undulated rings resulting in a desired cell pattern.

Figure 14:
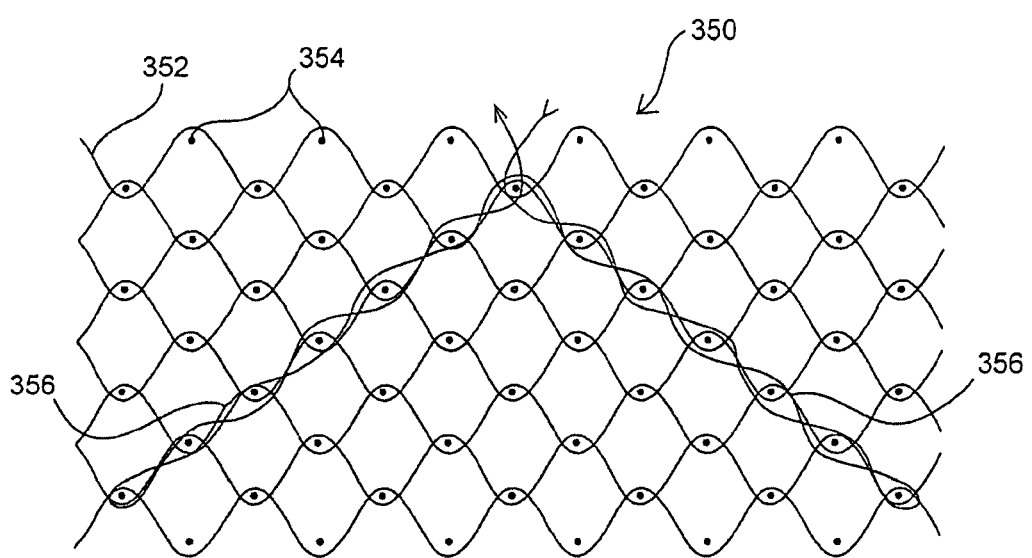
FIG. 14 illustrates an exemplary wire winding pattern to form a stent of the present invention.
Figure 15:
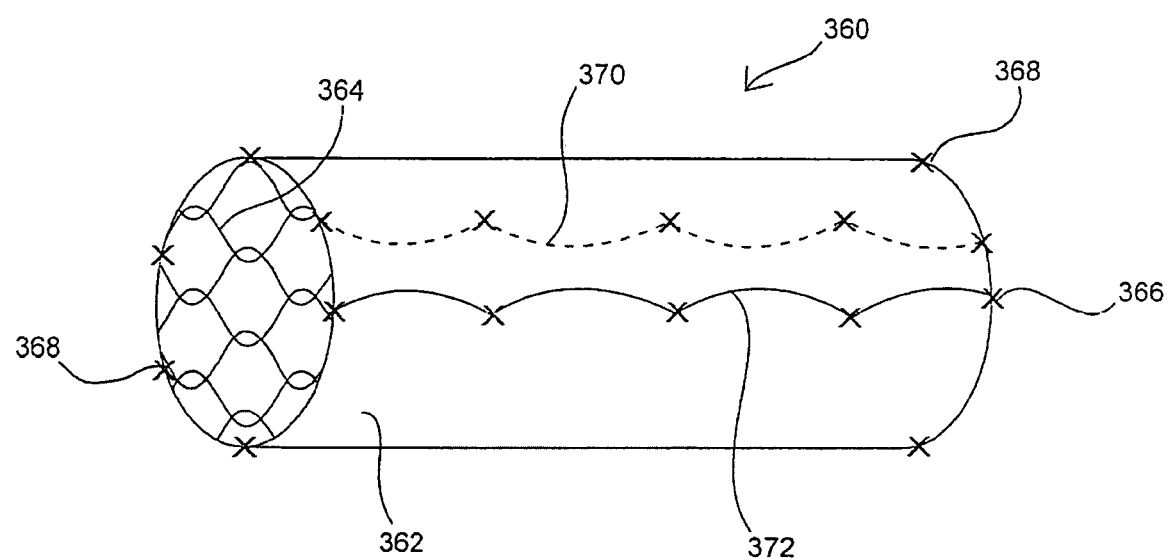
FIG. 15 illustrates one manner in grafting a stent of the present invention.

An exemplary wire winding pattern 350 is illustrated in FIG. 14. Starting from one end of the main mandrel, the wire 352 is wound around the pins 354 in a zigzag pattern back and forth from one end of the main mandrel to the other until the cells of the main lumen of the stent have been formed. Next, the same wire, still attached to the mandrel device, is used to form the side branch lumen(s) where the wire is wrapped in a zigzag fashion from the base of the side branch mandrel to the distally extending end and back again until all of the cells of the side branch have been created. Then the wire is wound about the main mandrel along a path that is at an angle to longitudinal axis of the main mandrel where the wire is doubled over itself along certain cell segments 356. It should be noted that any lumen of the stent may be fabricated first, followed by the others, or the winding pattern may be such that portions of the various lumens are formed intermittently.

The mandrel device with the formed wire stent pattern are then heated to a temperature in the range from about 480° C. to about 520° C. and typically to about 490° C. for approximately 20 minutes, however, this time may be reduced by using a salt bath. The duration of the heat-setting step is dependent upon the time necessary, to shift the wire material from a Martensitic to an Austenitic phase. The assembly is then air cooled or placed into a water bath to quench for 30 seconds or more and then allowed to air dr. Once the stent is sufficiently dried, the pins are either pulled from the mandrel device or retracted into the hollow center of the mandrel by an actuation of an inner piece which projects the pins out their respective holes in the outer surface of the mandrel. The stent with its interconnected lumens can then be removed from the mandrel device. Alternatively, with the mandrel components detached from one another, one of the lumens, e.g., the main stent lumen, may be formed first followed by formation of a side branch lumen after attachment of a side mandrel to the main mandrel.

Optionally, the portions of the wire forming the side branch lumen cells may be selectively reduced in diameter by etching or e-polishing so as to exert less radial force than that wire portion of main lumen of the stent.

Another method of making the stent is to cut a thin-walled tubular member, such as stainless steel tubing, to remove portions of the tubing in the desired pattern for the stent, leaving relatively untouched the portions of the metallic tubing which are to form the stent. The stent also can be made from other metal alloys such as tantalum, nickel-titanium, cobalt-chromium, titanium, shape memory and superelastic alloys, and the nobel metals such as gold or platinum.

In accordance with the invention, one of skill in the art would know that several different methods may be employed to make the subject stents such as using different types of lasers; chemical etching; electric discharge machining; laser cutting a flat sheet and rolling it into a cylinder: all of which are well known in the art at this time.

Where a stent graft 360 is to be formed by the addition of a graft material 362, such as an ECM, to the subject stent 364, any manner of attaching the graft material to the wire form may be used. In one variation, the graft material is attached by way of a suture 366. As such, one edge 370 of the graft material is stitched lengthwise to the stent frame along the stents length, where at least one knot 368 is tied at each apex of the stent to secure an end of the graft to the stent. Then the graft material is stretch around the surface of the stent and the opposite edge 372 of the graft is overlapped with the already attached edge 370 and independently stitched to the stent frame to provide a leak free surface against which blood cannot escape. The graft material is stretched to an extent to match the compliance of the stent so that it does not drape when the stent is in the expanded state. Upon complete attachment of the graft material to the stent, the graft is dehydrated so that it snuggly shrinks onto the stent frame similar to heat shrink tubing would when heated.

Delivery and Deployment Systems of the Present Invention

Figure 2A:
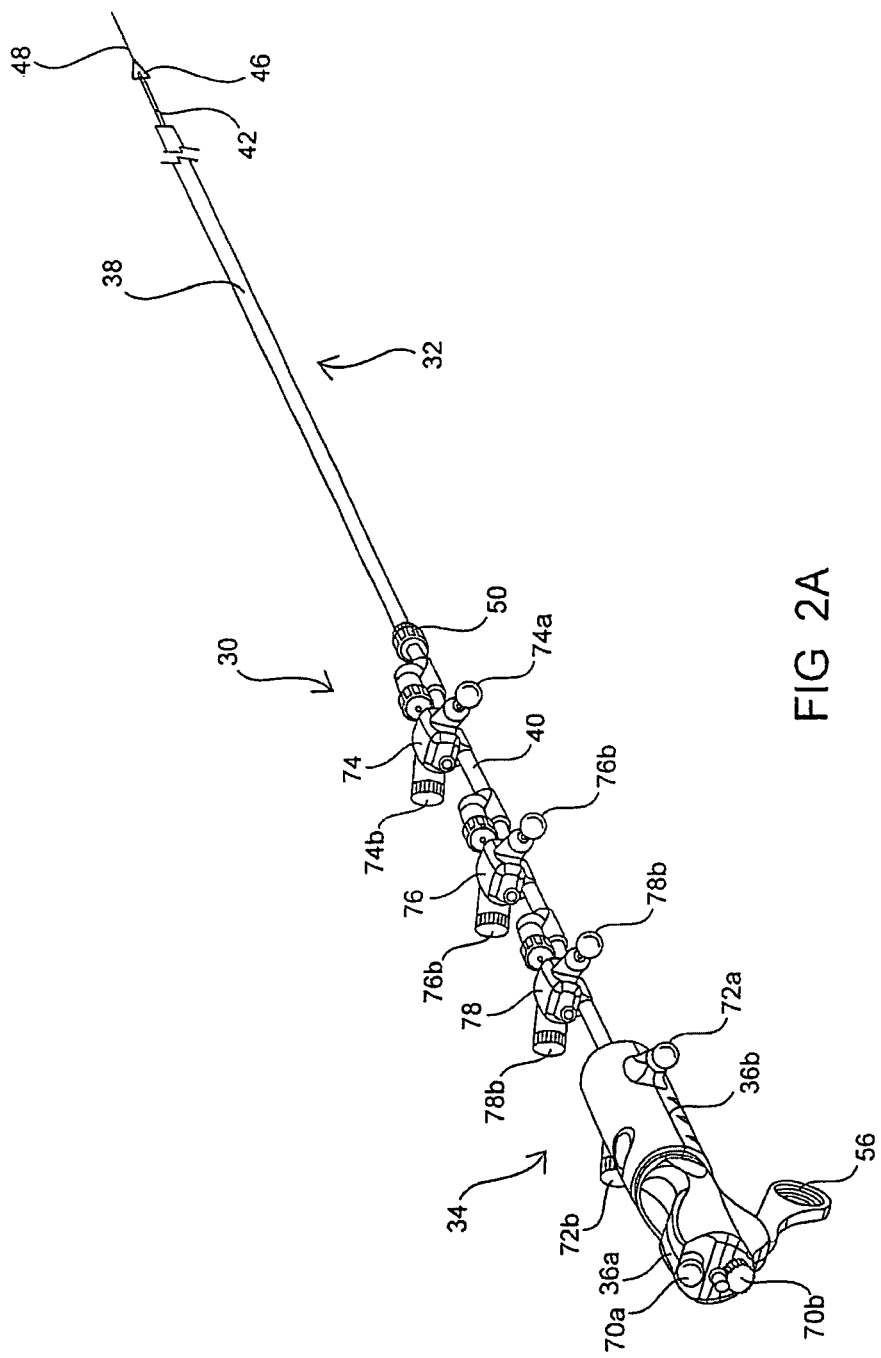
FIG. 2A is a perspective view of a system of the present invention for delivering and deploying the implants of the present invention within a tubular tissue structure within the body.
Figure 2B:
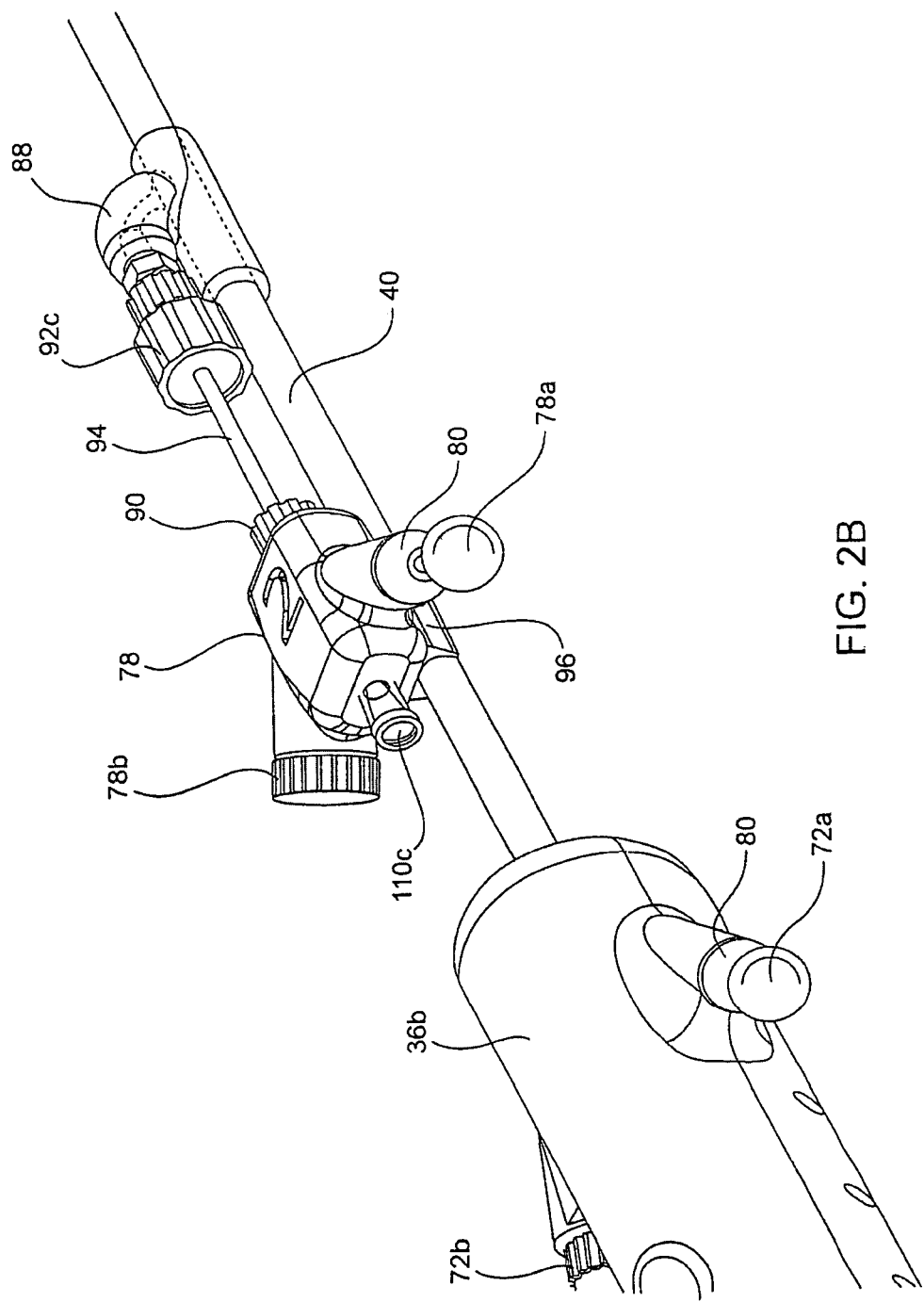
FIG. 2B is an enlarged perspective view of the portion of the system of FIG. 2A including a side branch control and catheter hubs.

Referring now to FIGS. 2A and 2B, there is shown a system 30 of the present invention for implanting the devices of the present invention. System 30 includes a distal catheter portion 32 and a proximal or handle portion 34. Catheter portion 32 is configured for positioning within the vasculature or other pathway leading to the implant site, and includes various elongated members having a plurality of lumens, many of them multi-functional, for guide wire, pull-wire, and fluid passage from one end of the device to the other. Catheter portion 32 includes a translatable outer sheath 38 having a lumen within which an intermediate member 40 is received. The proximal end of outer sheath 38 is configured with a fitting 50 for coupling to a distal hub 52 of intermediate portion 40. Fitting 50 is configured with an internal valve mechanism which fluidly seals the luminal space between the walls of outer member 38 and intermediate member 40, thereby preventing leakage of blood therefrom. Fitting 50 may further include a flush port (not shown) for evacuation of any residual air as is common in catheter preparation. An inner member 42 is received and translatable within a lumen 138 (see FIG. 6A) of intermediate member 40 and defines a main body guide wire lumen 44 for translation of a guide wire 48 therethrough. Inner member 42 terminates at a conical distal tip 46 which facilitates forward translation of the device through tortuous vasculature. The outer member, intermediate member and inner member tubings (as ell as any catheter components discussed below) may be made from materials used to construct conventional intravascular sheaths and catheters, including but not limited to biocompatible plastics reinforced with braided materials or any other biocompatible materials which are substantially flexible.

The proximal portion 34 of deliver; and deployment system 30 includes proximal and distal handle portions 36a, 36b which translate axially with respect to each other. Inner member 42 is fixed to proximal portion 36a of the handle and intermediate member 40 is fixed to distal portion 36b of the handle such that axial separation and extension of the two handle portions relative to each other controls the amount of extension and foreshortening undergone by a stent operatively loaded within the delivery system, as will be explained in greater detail below.

As mentioned above, the delivery and deployment of an implant of the present invention is accomplished by the use of a plurality of designated attachment strings, wires or filaments. A single string or a set or plurality of strings is provided for controlling and releasably attaching each free end of the implant to the delivery system. Two separate strings or sets of strings are employed to control the main tubular portion of an implantable device—one string or set of strings for controlling the distal end and the other for controlling the proximal end of the device. For each lateral branch of the implant, an additional string or set of strings is provided. The number of strings in each set correlates to the number of croons or connecting points provided at the respective ends (i.e., at the proximal and distal ends of the main stent portion and at the distal ends of the branch portions) of the device. Each string is interlooped with a designated crown with both of its ends positioned and controlled at the handle of the device, where one end of each attachment string is permanently affixed to the delivery and deployment system 30 and the other end is releasably attachable to the delivery and deployment system 30. When operatively loaded within system 30, the luminal ends of the implant are releasably attached to various portions of system 30. For example, the distal end of the main lumen of the stent is releasably attached to inner member 42, the proximal end of the main hunen of the stent is releasably attached to intermediate member 40, and the distal end of each side branch stent is releasably attached to a designated side branch catheter 150 (see FIG. 6A).

Each attachment string or set of attachment strings is controlled, i.e., able to be fixed, released, tensioned, pulled, tightened, etc., by a designated control mechanism. Accordingly, the number of control mechanisms provided on the illustrated embodiment of the subject system corresponds to the number of attachment string sets; however, control of the string sets may be consolidated into a fewer number of control mechanisms. The various control mechanisms may have any suitable configuration and be mounted at any, suitable location on system 30 where one exemplary configuration and location of the control mechanisms is illustrated in FIG. 2A. In particular, each control mechanism includes a pair of controls in the form of knobs, dials, switches or buttons, for example, where one control is for linearly translating, i.e., pulling, the strings by their fixed ends through the deployment system 30 when deploying the implant, and the other control is for selectively releasing and fixing the free ends of the strings prior to deployment of the implant.

Controls 70a, 70b and 72a, 72b, for controlling the distal and proximal luminal ends, respectively, of the implant, are provided on handle portions 36a and 36b, respectively. An additional pair of controls for each set of attachment strings associated with each of the implant's side or lateral branch lumens is provided on a hub releasably mounted to intermediate member 40 where the collective hubs are serially arranged between the proximal end 50 of outer sheath 38 and the distal end of distal handle portion 36b. For example, for use with implant 2 of FIG. 1A having) three branch lumens 6a, 6b and 6c, three hubs 74, 76 and 78 and associated pairs of controls, respectively, are provided where the most distal pair of controls 74a, 74b controls the attachment strings for the most distal of the stent branch lumens 6a, the second or middle pair of controls 76a, 76b controls the attachment strings for the middle stent branch lumen 6b, and the most proximal pair of controls 78a, 78b controls the attachment strings for the most proximal of the stent branch lumens 6c.

Each pair of controls includes a fixed-end member 70a, 72a, 74a, 76a and 78a, here in the form of a knob, to which one set, the fixed set, of ends of the attachment strings is permanently anchored but which itself is removable from the respective handle portion or hub in order to manually pull the strings therethrough. This control maintains a constant tension on the attachment strings and keeping the implant restrained within the delivery system while the delivery system is being articulated through the vasculature. As best illustrated in FIG. 2B, each knob is positioned within a hemostatic valve 80 for preventing the back flow of fluid, e.g., blood, out of the handle or hub before and after the knob is removed therefrom. Each pair of controls also includes a releasable end member or clamp 70b, 72b, 74b, 76b and 78b, here in the form of a dial or drive screw, by which the free ends of the string set are releasably anchored to the respective handle portion or hub. When ready to deploy a respective luminal end of the implant, the drive screw is selectively loosened to allow for release of the tension on the respective string set. Those skilled in the art will appreciate that the relative positioning and arrangement of the various control mechanisms may vary, with the intent of providing an organized, ergonomically designed profile.

Figure 3A:
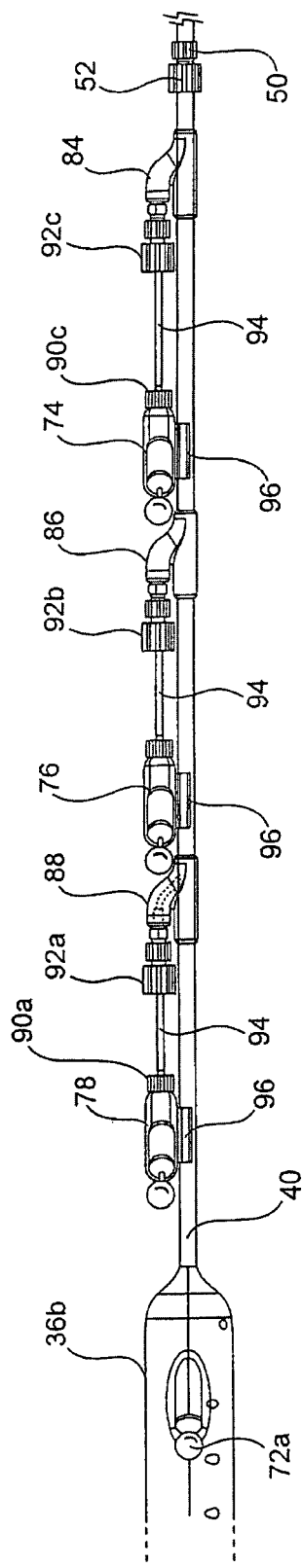
FIGS. 3A and 3B are side views of the side branch control and catheter hubs of the system of FIGS. 2A and 2B in open and closed configurations, respectively.
Figure 3B:
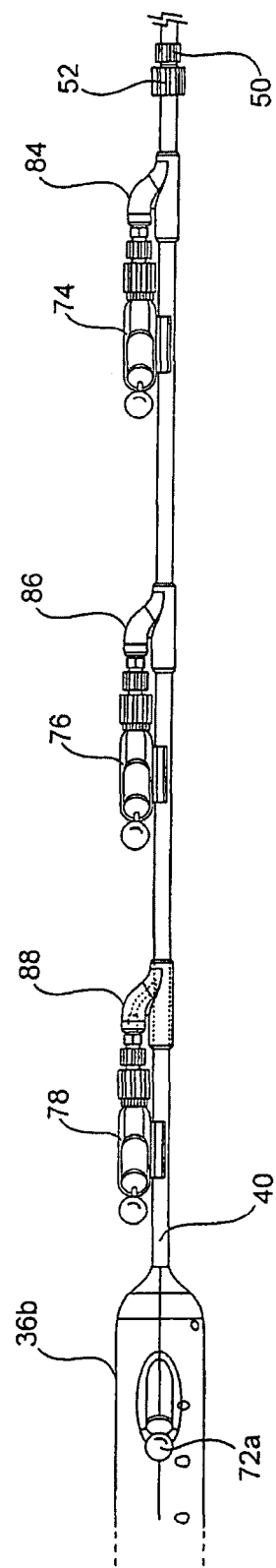

Referring now to FIGS. 2B, 3A and 3B, each side branch control hub 74, 76 and 78 is associated with a distally positioned side branch catheter hub 84, 86 and 88, respectively (only the most proximally positioned hubs 78 and 88 are illustrated in FIG. 2B). Extending between each pair of hubs is a proximal portion 94a, 94b, 94c of side branch catheters 150a, 150b, 150c, respectively (see FIG. 6A), which extends from a sealable port 110a, 110b, 110c (see FIG. 2B) at the back end of each control hub 74, 76 and 78 to a distal end and through respective side branch catheter lumens 148 within intermediate member 40 (see FIG. 6A). Within each side branch catheter 150a, 150b, 150c is a side branch guide wire lumen 152a, 152b, 152c (see FIG. 6A). Port 110a, 110b, 110c allows for the entry, and passage of a side branch guide wire 154a, 154b, 154c (see FIG. 6A) through a respective side branch guide wire lumen 152. One or both of the side branch catheter and side branch guidewire may be deflectable. Each of the control hubs 74, 76 and 78 are slidably engaged with intermediate member 40. The undersides of the control hubs have cuff 96, a partial ring configuration or the like, such that hubs are fully releasable from intermediate member 40 as well as slidable thereon. As mentioned above, each of the side branch stent lumens is releasably coupled to the distal end of side branch catheter 150a, 150b, 150c by way of a designated attachment string or set of attachment strings. Regardless of the relative position between the side branch control hubs 74, 76, 78 and the associated side branch catheter hubs 84, 86, 88, the attachment string sets are held in complete tension in both configurations illustrated in FIGS. 3A and 3B until they are released by their respective control knobs 74b, 76b, and 78b. When the control hubs are in a distal or close position relative to the catheter hubs, as illustrated in FIGS. 2A and 3B, where the proximal portion 94a, 94b, 94c of side branch catheter 150a, 150b, 150c is fully received within the associated catheter hub, the side branch stents are held in a partially deployed state. In the partially deployed state, the side branch stents are held stretched, with tension being applied by the distal end of the respective extended side branch catheter 94a, 94b, 94c removably attached to the distal end of the stretched side branch stent apices or connection points by the side branch catheters' respective string or string set. The tension being applied to the distal end of each side branch stent is transferred through the side branch stent thereby elongating its length while simultaneously reducing the diameter. This allows for the positioning of a larger stent diameter within a smaller diameter side branch vessel. This partially deployed state, i.e., where the side branch stent diameter is smaller than the side branch vessel into which it is being placed, also allows for the flow of blood around the implant as well as through it thereby allowing perfusion of downstream vessels and organs during placement. It is preferential to have blood continue to flow through intersecting side branch vessels during the procedure in order to avoid ischemia to the effected downstream organs. The side branch stent is stretched by the extension of the side branch catheter which is releasably attached to the crowns of the distal end of the side branch stent. The stretching of the side branch stent enables its subsequent placement within an undersized, targeted side branch vessel. Typically, the diameter of a side branch stent in its natural, unconstrained or stretched state is about 5% to about 50% greater than the diameter of the side branch vessel into which it is to be placed. Conversely, when the control hubs are in a proximal or retracted position, as illustrated in FIGS. 2B and 3A, each side branch stent is held in a deployed or unstretched condition.

The side branch catheters 150a, 150b, 150c slidably extend at their proximal ends 94a, 94b, 94c through respective side branch catheter hubs 84, 86, 88 and a hemostatic valve 92a, 92b, 92c positioned at the back end of the catheter hub. Each side branch control hub 74, 76, 78 has a luer fitting 110a, 110b, 110c (where only 110c is shown) which allows a hemostatic valve (not shown) to be applied. The hemostatic valve may be a Y arm adapter or a Toughy-Borst adapter which allows the sealed introduction of a guidewire. The Y arm luer fitting allows for clearing the guidewire lumen of air by flushing the catheter with saline prior to inserting the catheter into the body. At subsequent stages of the procedure, this lumen may be used to introduce radiographic dye in order to visualize blood flow through the side branch arteries.

Figure 4:
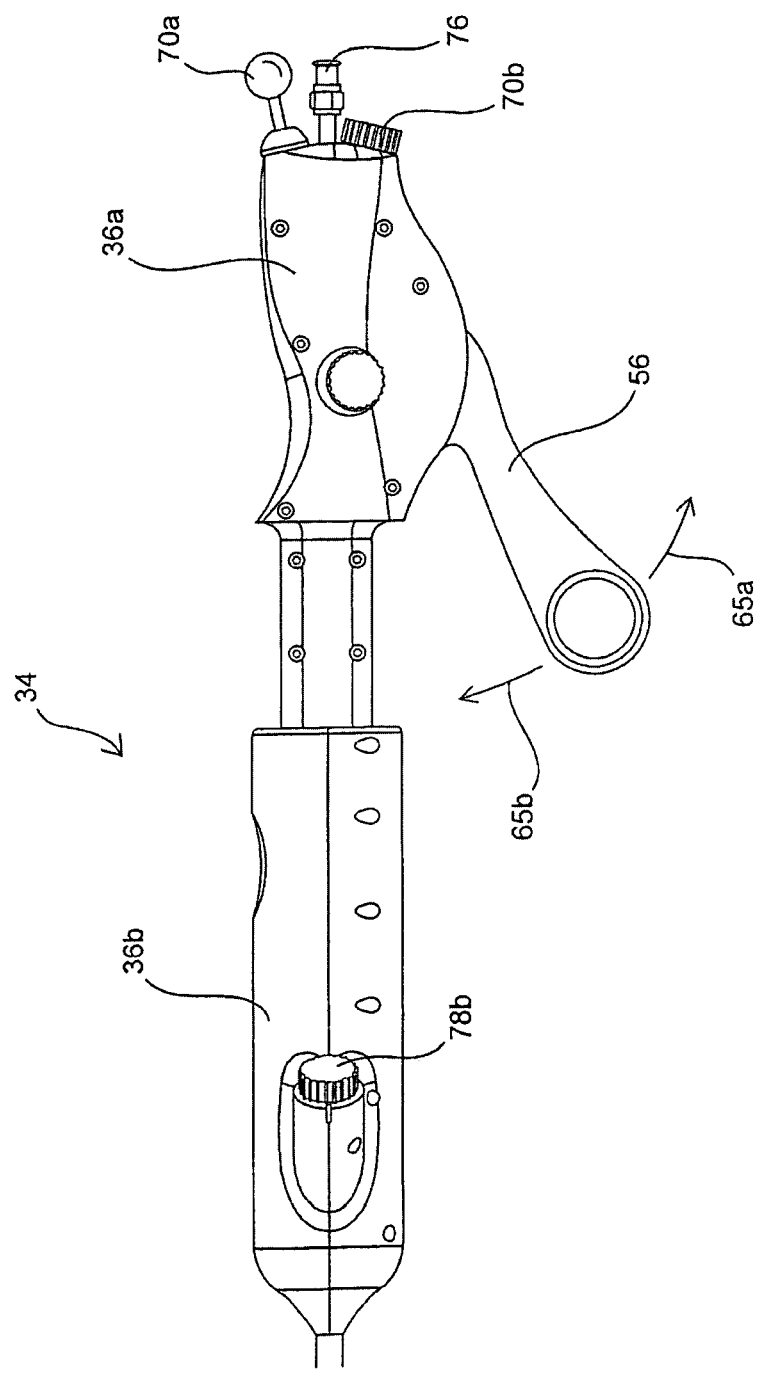
FIG. 4 is a side view of the handle portions of the system of FIG. 2A.

A main body port 76, as illustrated in FIG. 4, located on the back end of proximal handle portion 36a is in fluid communication with a guide wire lumen 44 which extends through a central lumen 138 (see FIGS. 6A and 6B) within intermediate member 40. Guide wire lumen 44 provides for the passage and translation of a primary guide wire 48 which is used to direct and guide distal portion 32 of the system to a target implant site within the vasculature as well as to facilitate the positioning and implantation of the distal end of the primary, lumen of the implantable device. The main body port 76 has a luer fitting similar to leur fitting 110 described above with respect to the side branch catheter control hubs.

Figure 9:
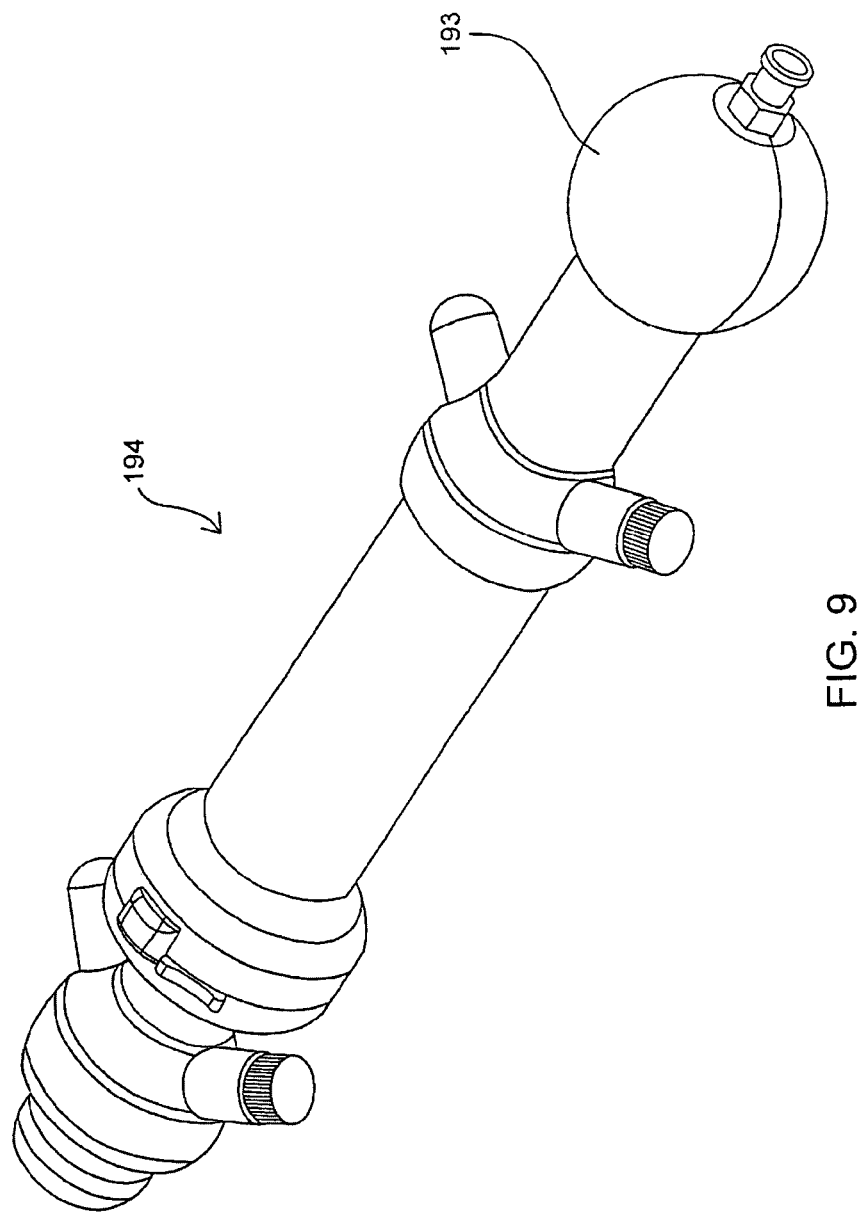
FIG. 9 illustrates another embodiment of handle portion of the deliver, and deployment system of the present invention.

As is further illustrated in FIG. 4, a lever mechanism 56 extending distally and downwardly from proximal handle portion 36a is provided for steering distal catheter portion 32 of device 30 through the vasculature into which it is positioned. This lever may be replaced by a rotating control knob 193 in another handle embodiment 194 shown in FIG. 9A. A steering pull-wire, string or filament (not shown) is Fixed to the proximal end of lever 56 and extends through catheter portion 32 where its distal end terminates and is attached within nose cone 46 of inner member 42. Lever 56 is pivotally coupled within handle portion 36a such that when rotated in a downward direction (indicated by arrow 65a of FIG. 4), the steering pull-wire is caused to be in a relaxed or slacken state. Conversely, when lever 56 is rotated upward (indicated by arrow 65b), the steering pull-wire is pulled or tensioned thereby causing the distal tip of inner member 42, and thus the distal end of device 30, to bend. Any number of steering pull-wires may be employed and selectively tensioned to selectively articulate the distal end of device 30 in multiple directions orthogonal to the longitudinal axis of the implantation system. Typically, the subject delivery and deployment system will have at least one, and often two to four distal points of articulation. These articulation points may be at one or more distances from the distal end of the catheter 32 in order to create compound curves of the distal end of the catheter.

Figure 5A:
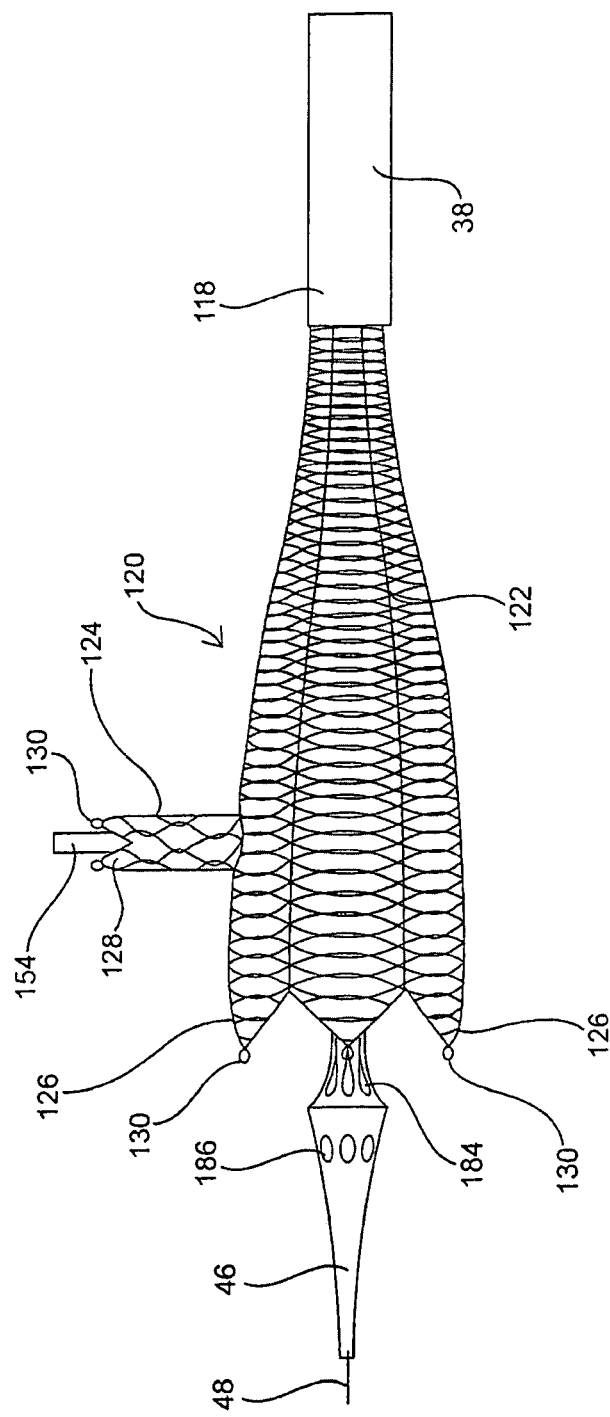
FIG. 5A is a side view of the distal end of the delivers and deployment system of the present invention with an implantable device of the present invention shown partially deployed from the implantation system.
Figure 5B:
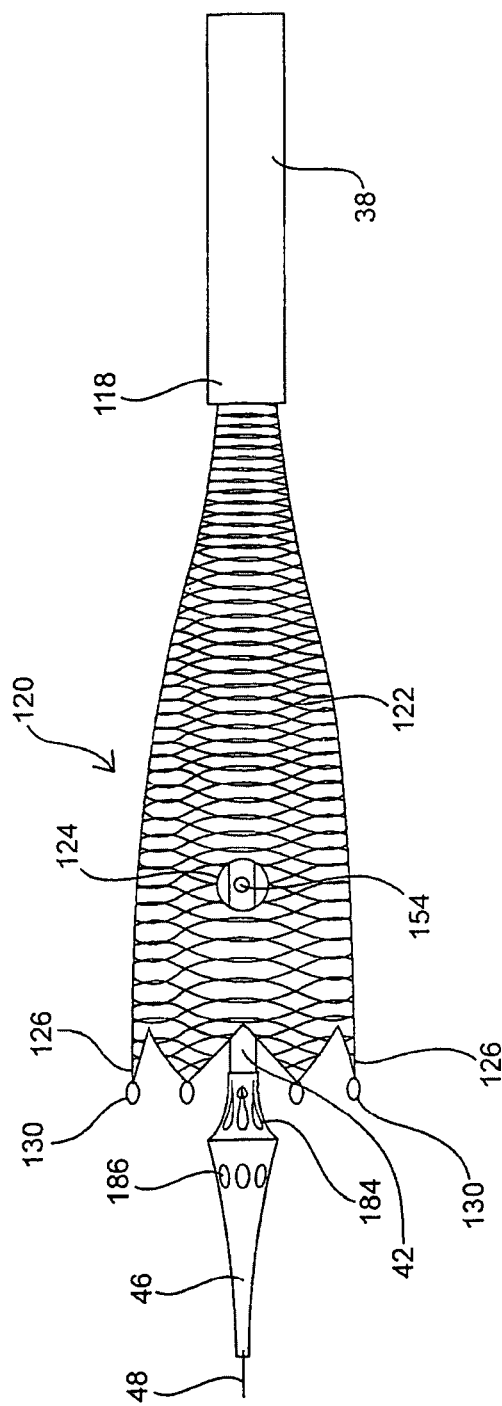
FIG. 5B shows a top view of the system and implantable device of FIG. 5A.
Figure 5C:
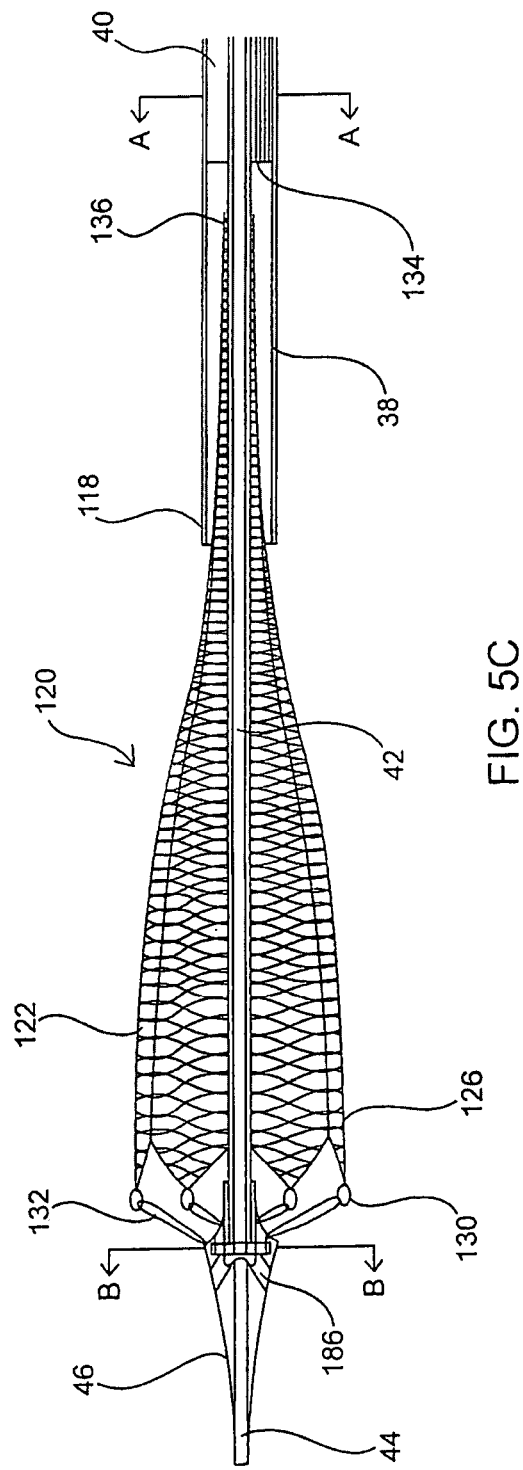
FIG. 5C shows a longitudinal cross-sectional view of FIG. 5B.

The relative positioning and interfacing of the implantable device with the various catheters, lumens, guidewires, ports and pull-wires of the subject implantation system will now be described with respect to FIGS. 5A-6C, 6A and 6B. FIGS. 5A-5C illustrate an implantable device 120 partially deployed from the distal end 118 of outer sheath 38. Implantable device 120 includes a main tubular body 122 and may include one or more lateral tubular branches 124. At the distal tips of crowns or apexes 126 of main body 122 and crowns or apexes 128 of side branch 124 may be eyelet loops 130 for receiving attachment strings 132 (shown only in FIG. 5C). Any means of looping the attachment wires to the end of side branch 124 may be used including passing attachment strings or strings through the windows provided by the cell structure terminating at an apex. As is illustrated in FIG. 5C, when operatively loaded within system 30 of FIG. 2A, the main lumen 122 of device 120 is longitudinally disposed between outer sheath 38 and inner member 42 and is positioned distally of the distal end 134 of intermediate member 40.

To load the implant device into outer sheath 38, the handle controls are set to stretch the stent by extension of the distal tip 46 of the inner member 42 relative to the distal end of the intermediate member. When proximal and distal handle portions 36a and 36b are extended from each other, shown in FIG. 8D, the main lumen of the stent is in a stretched or tensioned condition. Conversely, when proximal and distal handle portions 36a and 36b are unextended, as shown in FIG. 8E, the main lumen or the stent is in an unstretched or untensioned condition. The distal lumenal ends of inner member 42 and intermediate member 40 are connection points for the string or strings which are releasably attached to the distal and proximal stent main lumen openings 122. As discussed above, the side branch stent distal lumenal end is releasably attached to the distal end of the side branch catheter.

Figure 6A:
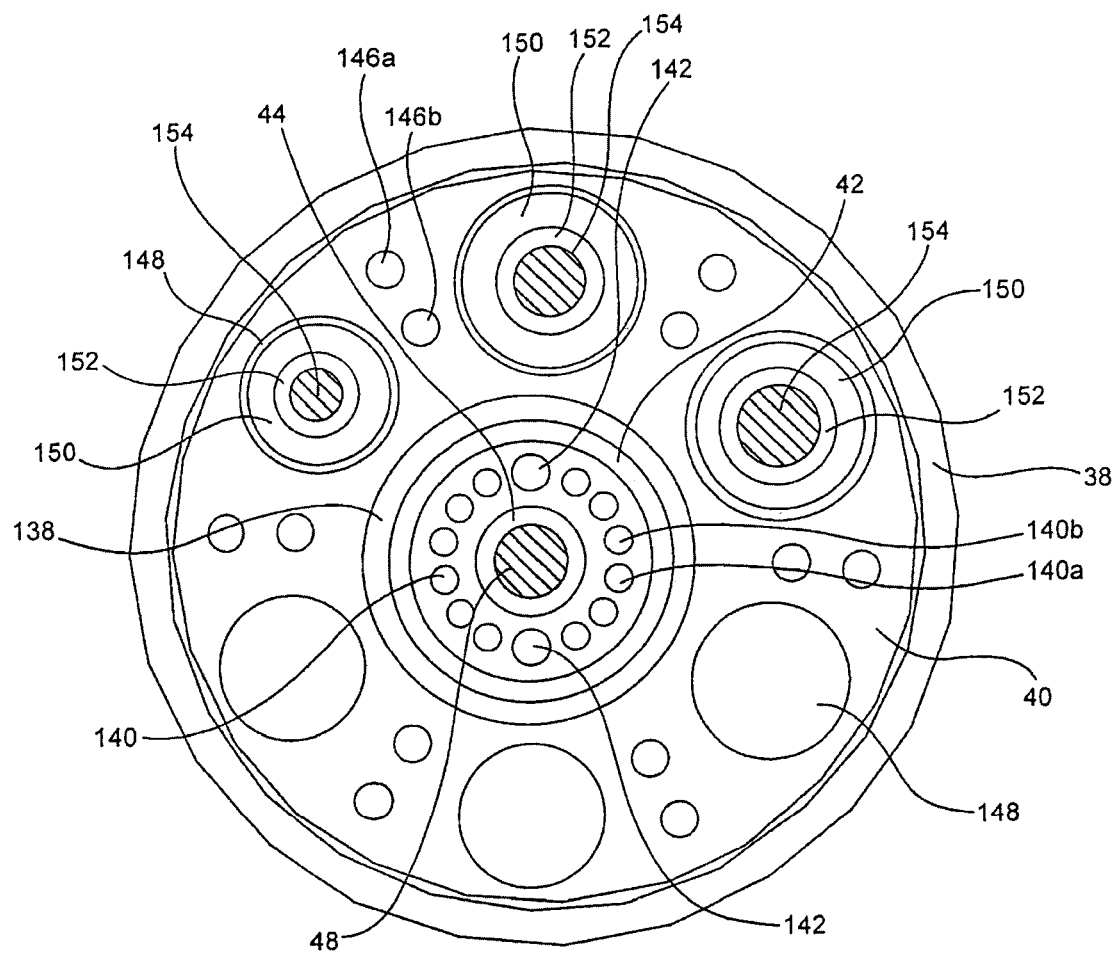
FIG. 6A is a cross-sectional view taken along line A-A of FIG. 5C.

FIG. 6A shows a cross-section of a distal portion of implantation system along the lines A-A of FIG. 5C, specifically, the cross-sectional view is taken at the distal end of intermediate member 40. This view shows the nested relationship between outer member 38, intermediate member 40, inner member 42 which is positioned within central lumen 138 of intermediate member 40, and main guide wire 48 positioned within a central guide wire lumen 44 of inner member 40 which extends distally through tip 46.

Inner member 42 is a very small diameter catheter, for example, in the range of 3 to 8 French for cardiovascular applications, and has, in addition to central guide wire lumen 44, a plurality of attachment string lumens 140 circumferentially disposed about central guide wire lumen 44 which serve to direct the alignment of the attachment strings to the connection points on the distal end of the main stent lumen. Multiple lumens 140 are located at the distal portion of member 42 and extend along the entire length of the inner member 42. Lumens 140 may be in communication with one or more flush ports at the handle portion of the delivery system whereby saline may be flushed through lumens 140 at a pressure greater than that of the surrounding blood flow to prevent blood flow through the device lumens. Lumens 140 may also be used to deliver radiopaque contrast dye used during fluoroscopically visualized placement of the device. Lumens 140 and the exit ports 186, described below, allow for visualization of the dye flowing through the implant at various stages of deployment in order to verify that placement of the stent yields a satisfactory flow pattern and therapeutic result.

In other embodiments, such as that illustrated in FIGS. 10A, 10B and 10C, attachment string lumens 140 mats extend along only a portion of the length of inner member 40, e.g., only a few millimeters distally to proximally. This embodiment is particularly suitable in the case where only one attachment string is employed with multiple stent connection points. Here, the single string element exits one of the distal lumens, is passed through the stent connection point, is passed distally to proximally through another of the lumens, exits proximally from that lumen and is passed through another of the lumens distally to proximally and passed through another stent connection point. The interlacing pattern continues until all stent connection points are laced with the singular string which passes through the multiple circumferential lumens. This configuration of attachment string lumens which extend only a portion of the length of the inner member, may also be employed with the intermediate member 40 and with the side branch catheters 94a, 94b, 94c. With respect to an intermediate member employing such a string lumen configuration, the proximal portion of intermediate member 40 would be a single lumen containing the inner member 42 and the shorter circumferential lumens would contain the side branch catheters as well as the attachment wires for the proximal end of the main stent lumen. As will be seen from this embodiment and those discussed below, any combination of lacing patterns may be used to attach an individual stent end to the respective catheter to which it is attached.

Referring again to the embodiment FIG. 6A, the number or distal attachment strings lumens 140 is double the number or attachment strings 132 where one pair of adjacent attachment strings lumens 140a, 140b is provided for each distal attachment string 132. As such, where device 120 is fully loaded within the deployment system, the first portion of a distal attachment string 132 resides within lumen 140a and a second or return portion of the distal attachment string resides within lumen 140b.

In addition to attachment string lumens 140 are one or more steering pull-wire lumens 142, the function of which is as described above with respect to FIG. 4. Typically, one or two pairs of diametrically opposed (180.degree. apart) steering pull-wires are employed to provide opposing orthogonal deflections of the distal end of the delivery system. The greater the number of steering pull-wire pairs employed, the greater the directions of steering in articulating the delivery system.

In addition to central lumen 138 through which inner member 42 is translated, intermediate member 40 includes a plurality of proximal attachment string lumen pairs 146a, 146b where lumen 146a is shows situated radially outward from lumen 146b. The attachment strings attached to or threaded through the proximal crowns (not shown) of main lumen 122 of device 120 utilize lumens 146. The number of proximal attachment string lumens 146 is double the number of proximal attachment strings where one pair of attachment string lumens 146a, 146b is provided for each proximal attachment string, i.e., where device 120 is fully loaded within the delivery, and deployment system, the fixed-end portion of a proximal attachment string resides within lumen 146a and the distal or return portion of the proximal attachment string resides within lumen 146b.

In addition to attachment string lumens 146, intermediate member 40 also provides a plurality of lumens 148, also circumferentially disposed about central lumen 138 and preferably interposed between pairs of proximal attachment lumens 146, where one or more of the lumens 148 may be employed to translate and deliver a side branch catheter 150 (shown in FIG. 6A without detail). Side branch catheter 150 provides a central side brunch guide wire lumen 152 for delivering and translating a side branch guide wire 154. Additional lumens 148 extending from a handle flush port (not shown) may be provided for evacuating air from the delivers system 30. The additional lumens 148 may, also allow for the rehydration of tissue graft coverings or other coverings which need to be prepared with solutions and potential therapeutic agents such as pharmacologics, stem cells, or other agents. This allows the stent graft or other device to be constrained in the delivery catheter in a dried dehydrated state subsequently packaged, sterilized, and rehydrated by the flushing and preparing the catheter at the time of use. Any unused lumens 148 provide enhanced flexibility of the intermediate member, particularly where the distal end of the device is deflectable at multiple articulation points.

Figure 7B:
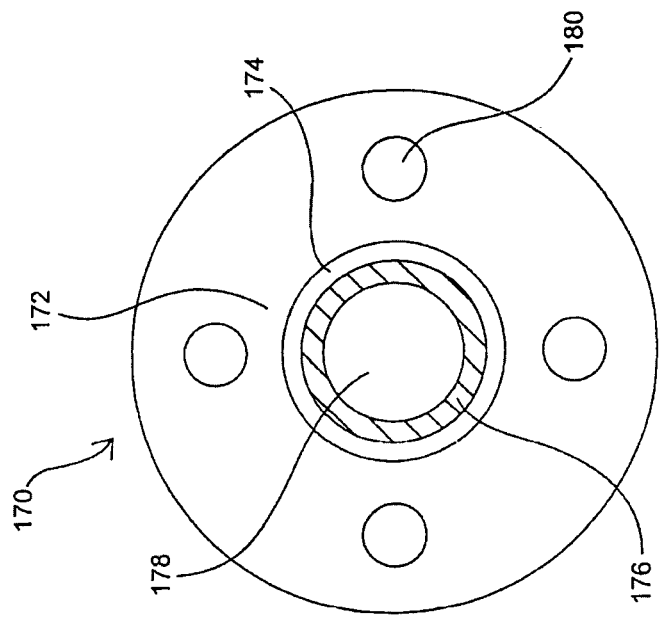
FIGS. 7A, 7B and 7C are cross-sectional views of possible embodiments of side branch catheters of the present invention.
Figure 7A:
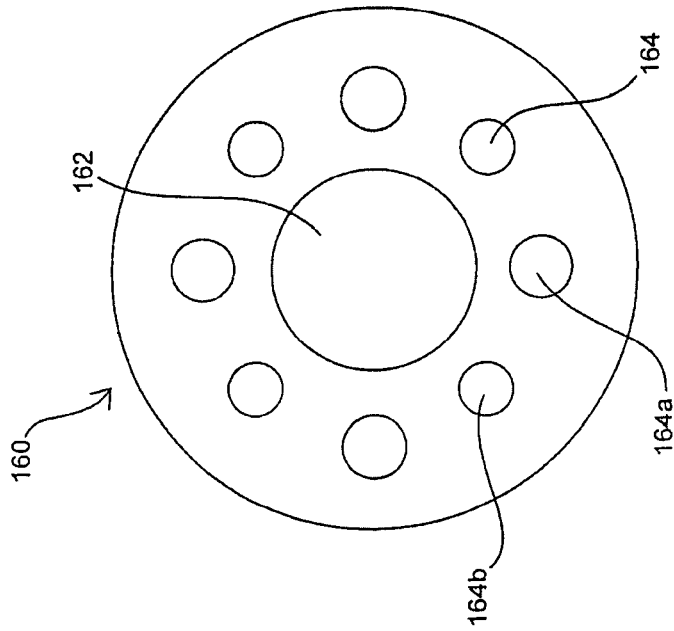
Figure 7C:
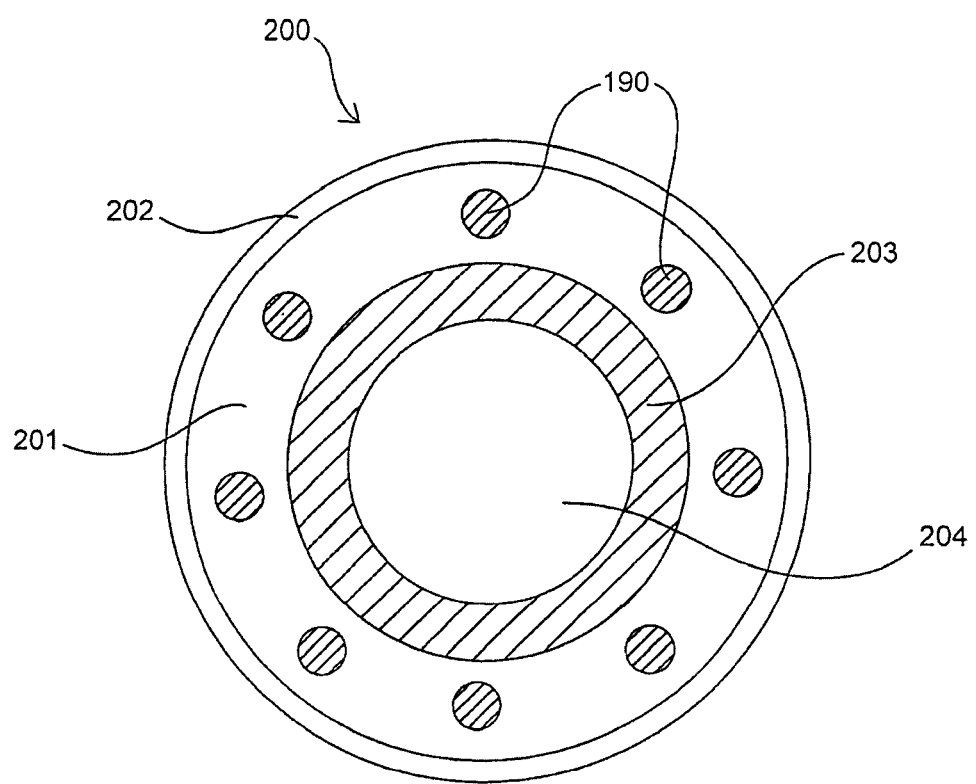

FIGS. 7A, 7B and 7C illustrate various possible embodiments of side branch catheters suitable for use with the deliver, system of the present invention. Side branch catheter 160 of FIG. 7A provides a central guide wire lumen 162 and plurality of attachment string lumens 164 arranged circumferentially about central lumen 162. Lumens 164 are utilized or occupied by the attachment strings (not shown) which are looped or threaded through the distal croons 128 of side branch lumen 124 of device 120 (see FIG. 5A). The number of side branch attachment string lumens 164 is double the number of side branch attachment strings where one pair of attachment string lumens 146a, 146b is provided for each side branch attachment string, i.e., where device 120 is fully loaded within the implantation system, the proximal portion of a side branch attachment string resides within lumen 164a and the distal or return portion of the side branch attachment string resides within lumen 164b.

Side branch catheter 170 of FIG. 7B provides an outer member 172 having a central lumen 174 and an inner member 176 positioned concentrically therein. Inner member 176 also has a central lumen 178 for translating and delivering a side branch guide wire (not shown). Outer member 172 further provides a plurality of side branch attachment string lumens 180 where there is a one-to-one correspondence between the number of side branch attachment string lumens 180 and the number of side branch attachment strings (not shown). In this embodiment, the proximal portion of side branch attachment strings reside within the space between the internal diameter of outer member 172 and the external diameter of inner member 176 and after being looped through the distal attachment eyelets, crowns or cells, the distal or return portion of the strings pass through lumens 180 of outer member 172.

In another embodiment of side branch catheter 200, shown in FIG. 7C the side branch catheter can be composed of two concentric single lumens. One single lumen tubing 202 defining an internal diameter and another single lumen tubing 203 defining an outer diameter provides for the side branch attachment strings to be contained within the space 201 between the internal diameter of the outer tubing 202 and the outer diameter of the inner tubing 203. The internal diameter of the inner tubing is used to translate a guidewire (not shown) through side branch guidewire lumen 204 which is isolated from the attachment strings as shown in FIG. 7C. This lumen configuration may also be employed with the intermediate and inner members.

Figure 6B:
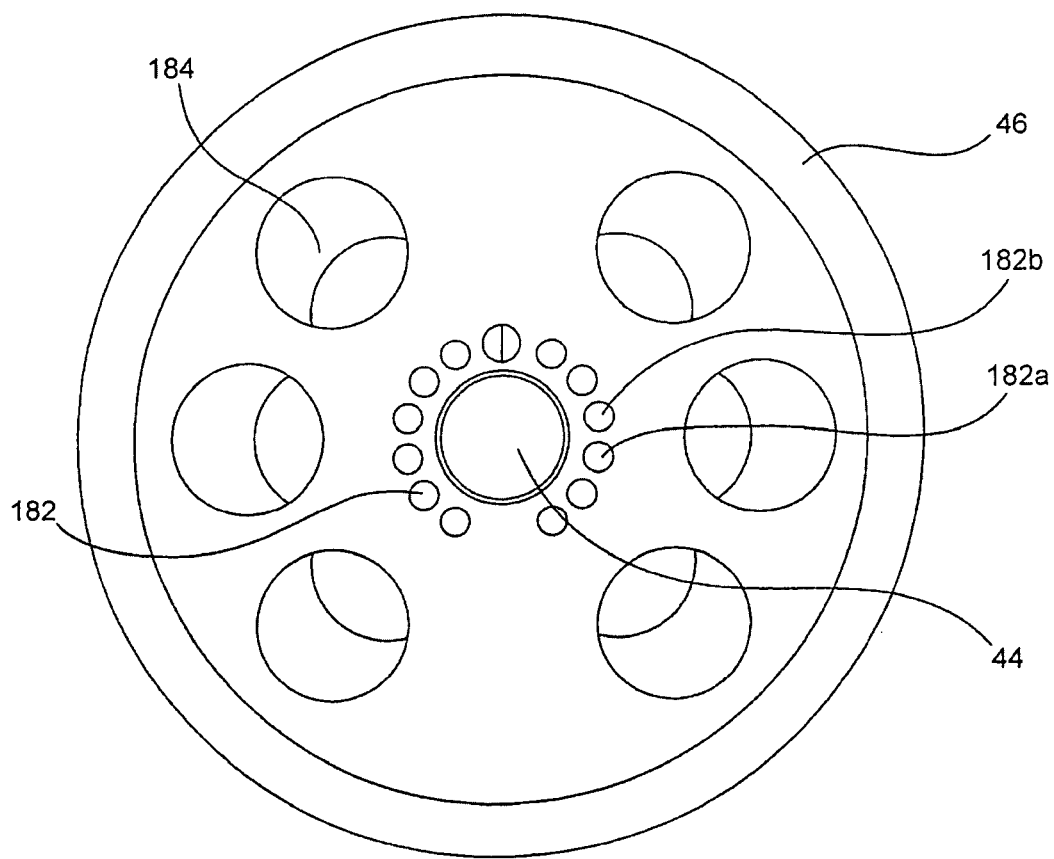
FIG. 6B is a cross-sectional view taken along line B-B of FIG. 5C.
Figure 6C:
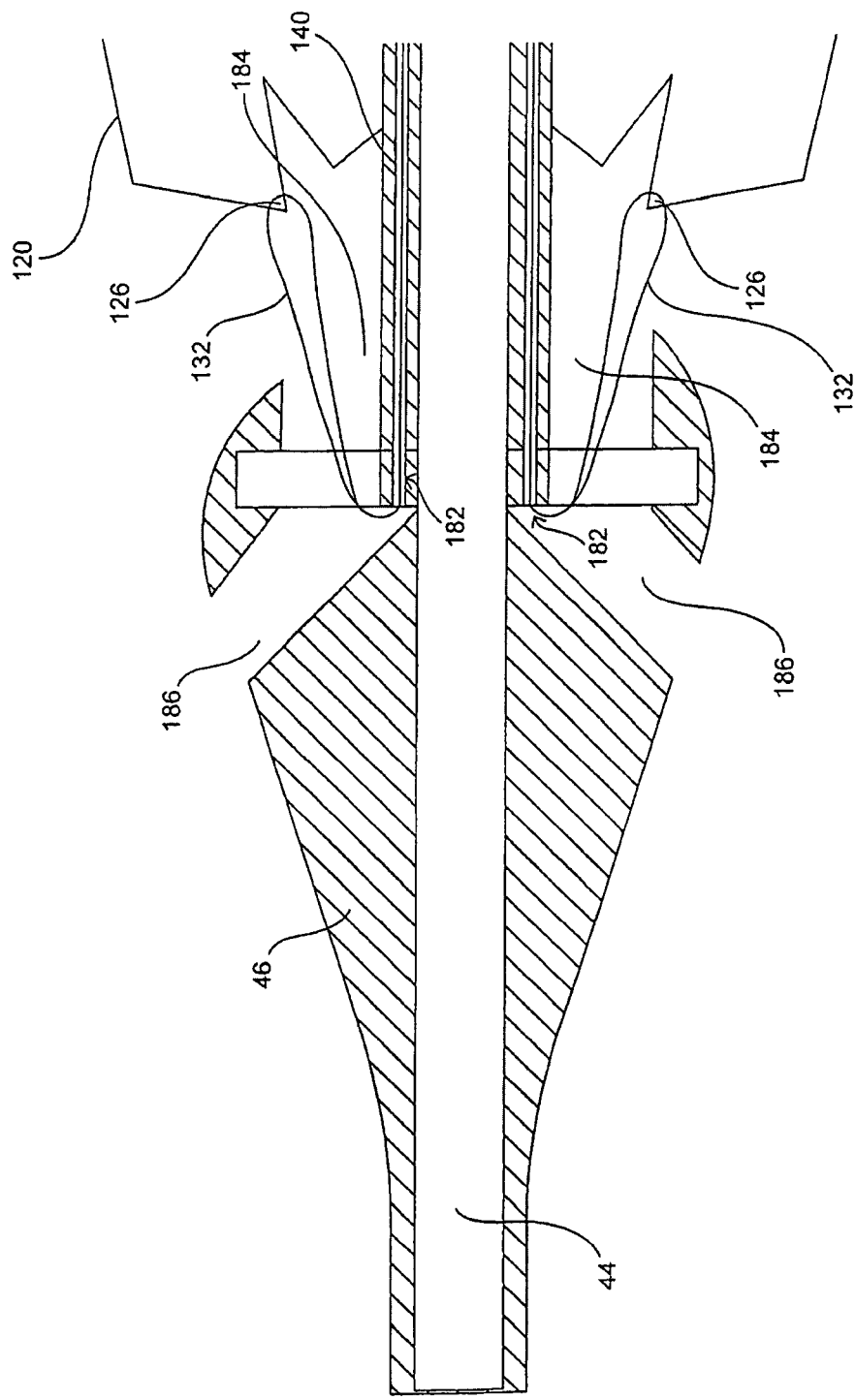
FIG. 6C is longitudinal cross-sectional view of the catheter tip portion of the delivery and deployment system of FIG. 5C.

Referring to FIG. 6B, there is shown a cross-sectional view taken along lines B-B of FIG. 5C, specifically through a proximal end of distal tip 46 where inner member 42 terminates. Distal tip 46 provides the distal portion of guide wire lumen 44 as well as the distal lumen portions 182 of distal attachment string lumens 140 of inner member 42 where the plurality of distal lumen portions 182 are axially aligned and have a one-to-one correspondence with inner member attachment string lumens 140. As such, the same pairing of adjacent attachment string lumens 182*a*, 182*b* is provided for each distal attachment string 132, i.e., where the fixed-end portion of a distal attachment string 132 resides within lumen portion 182*a* and the releasable or return portion of the distal attachment string resides within lumen portion 182*b*. As is best illustrated in FIG. 6C, after passing within lumen portions 182*a*, the attachment strings 132 are passed radially out of distal tip 46 through designated proximal side ports 184. The attachment strings are then looped or threaded around eyelets 130 or crowns or apices 126 or through the very distal cells of main lumen 122, and threaded back through the designated side port 184 of distal tip 46 whereby the re-enter respective lumen portions 182 and respective attachment string lumens 140. As such, for every, pair of attachment string lumens, there are half as many side ports 184, i.e., there is a one-to-one correspondence between the number of attachment strings 132 and the number of distal tip side ports 184. Distal tip 46 also provides for distal side ports 186 to facilitate the loading of strings during assembly or the implant to the deliver system.

Methods of Device Implantation

Figure 8B:
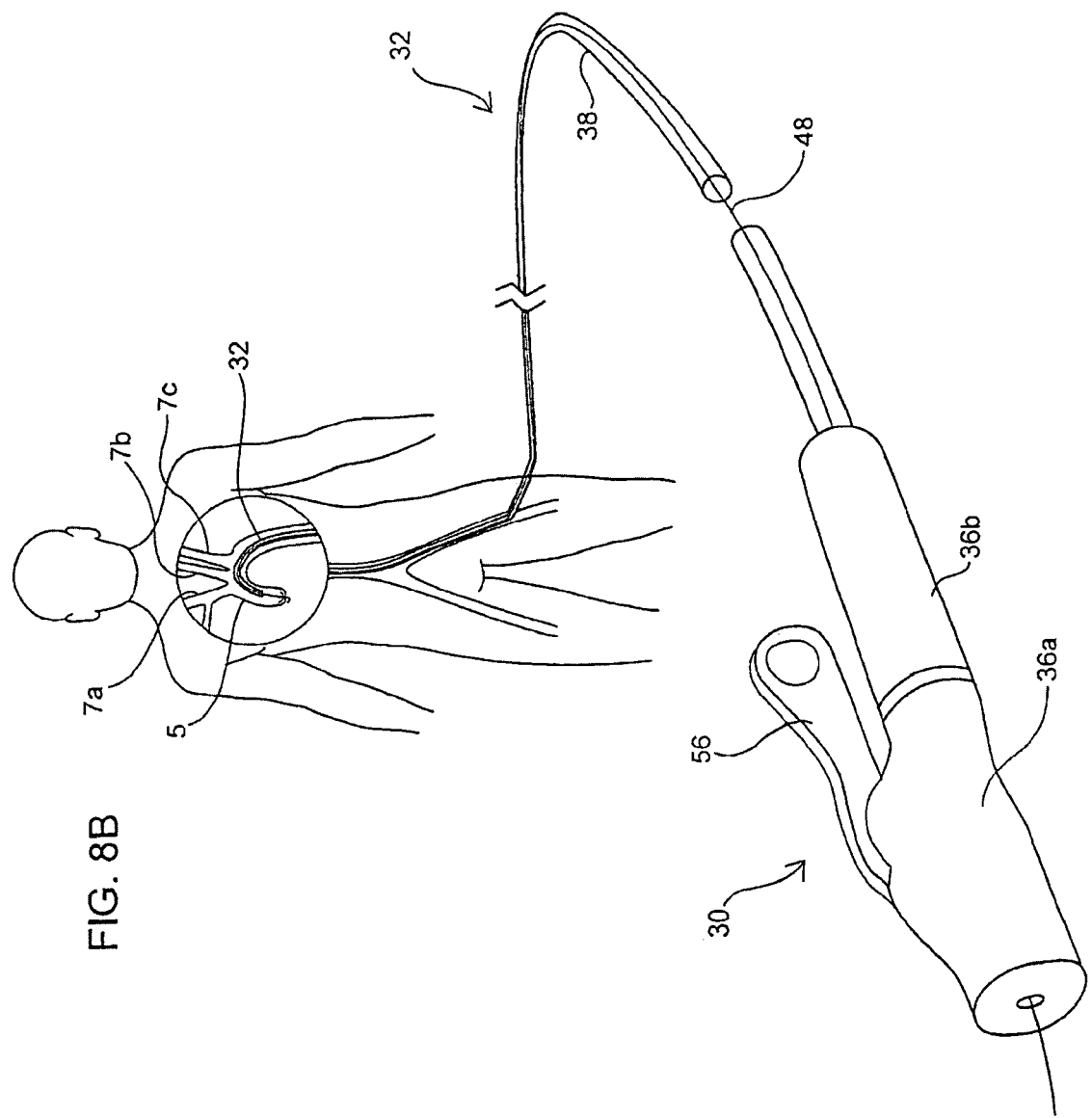
Figure 8C:
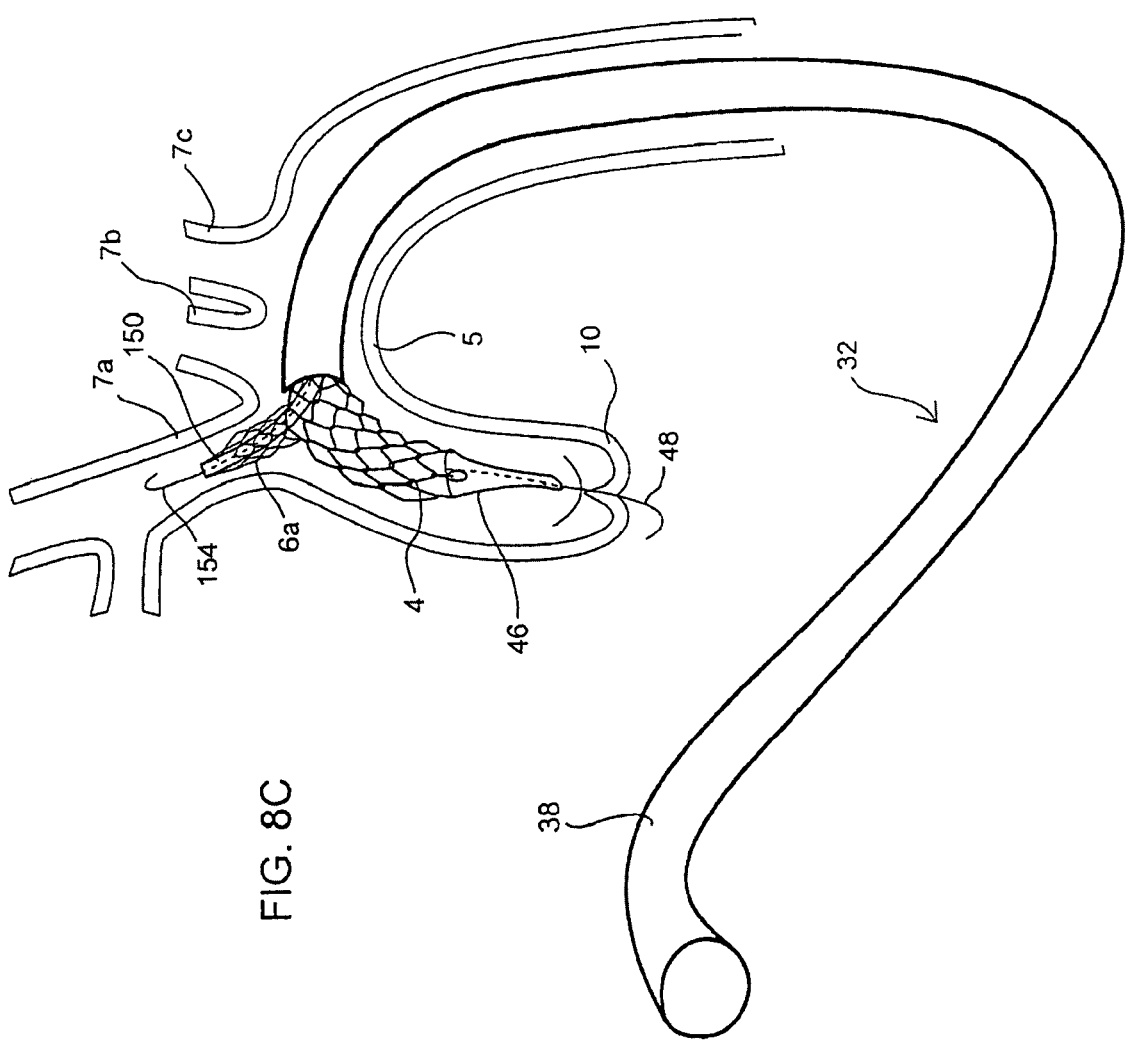
Figure 8D:
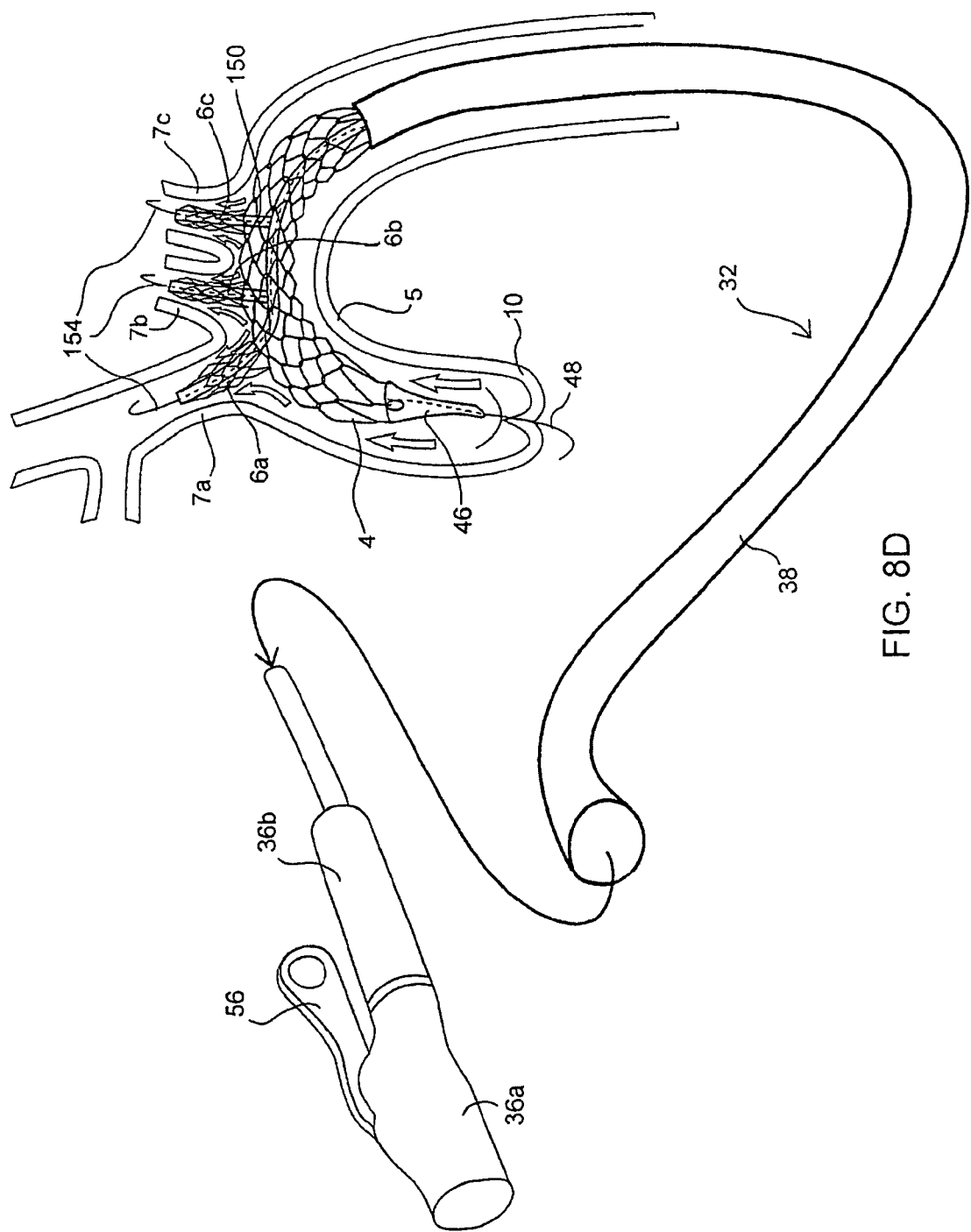
Figure 8E:
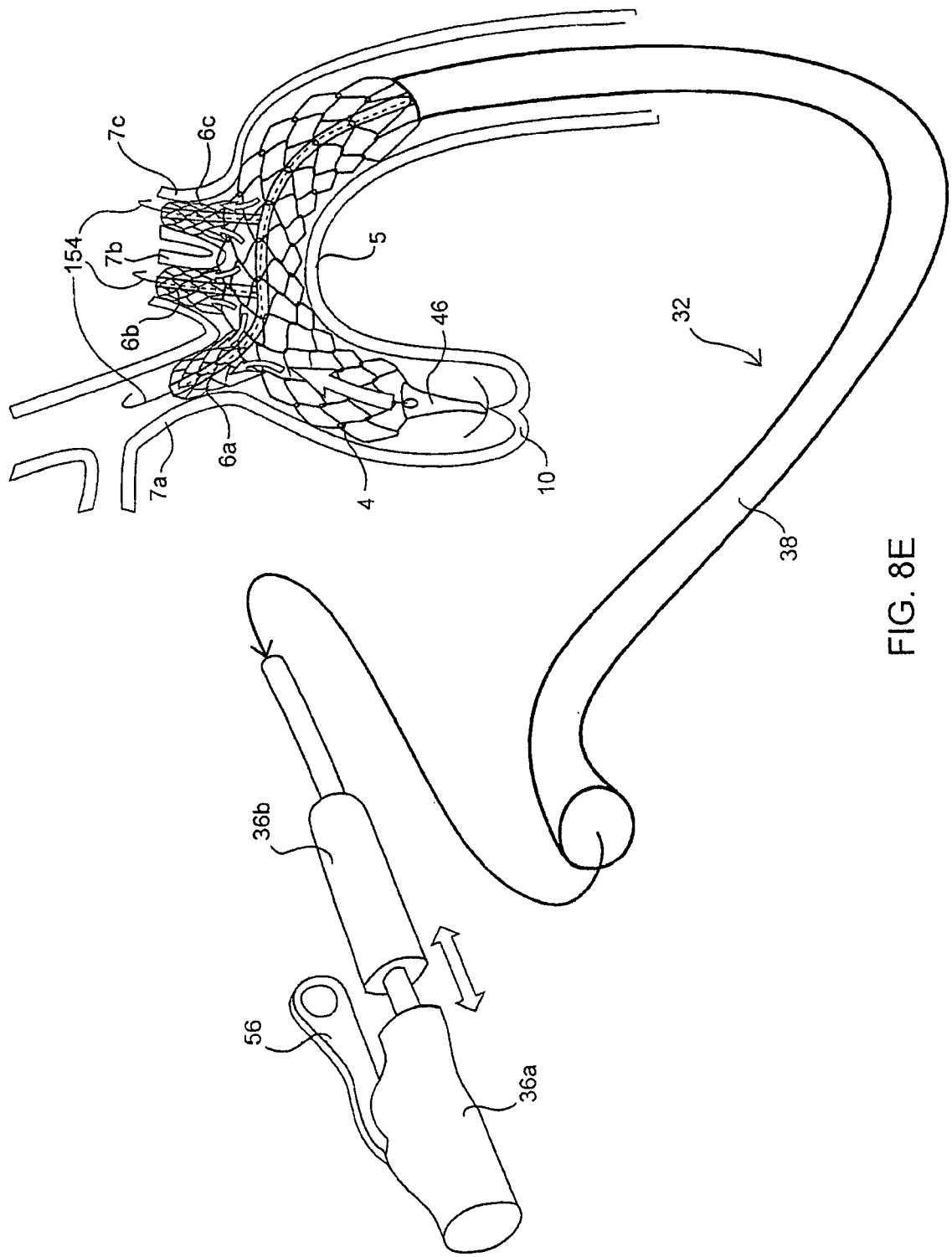
Figure 8F:
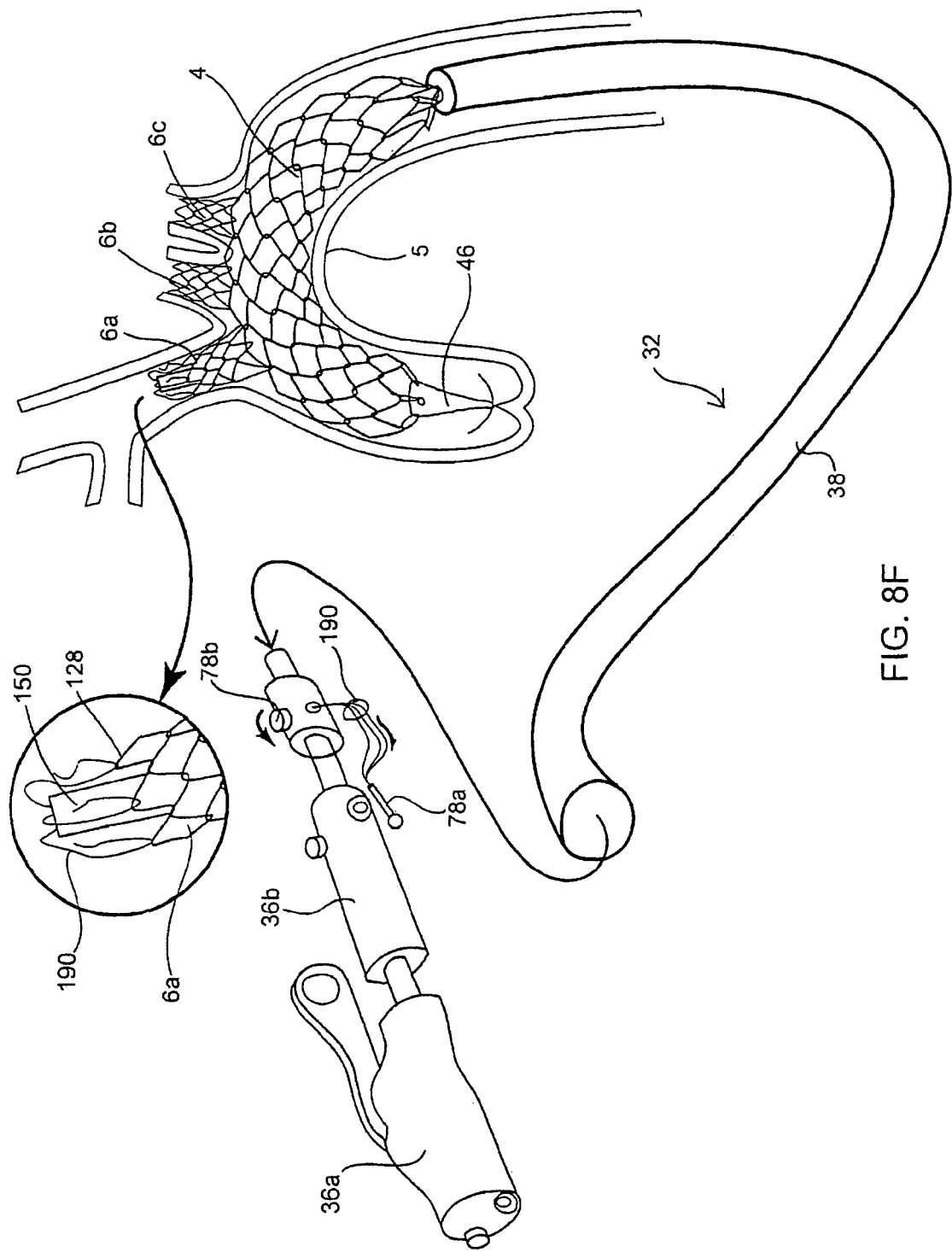
Figure 8G:
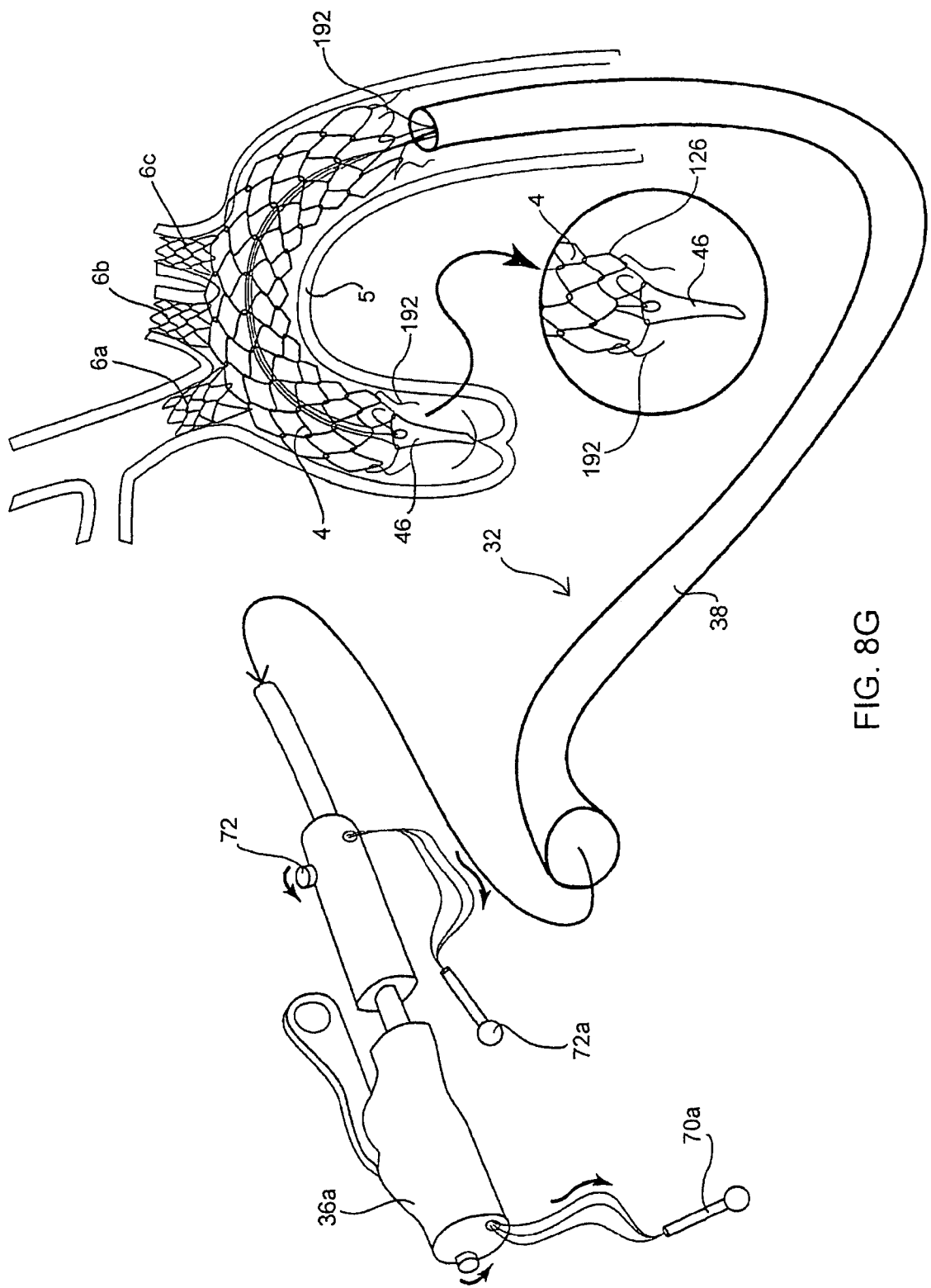
Figure 8H:
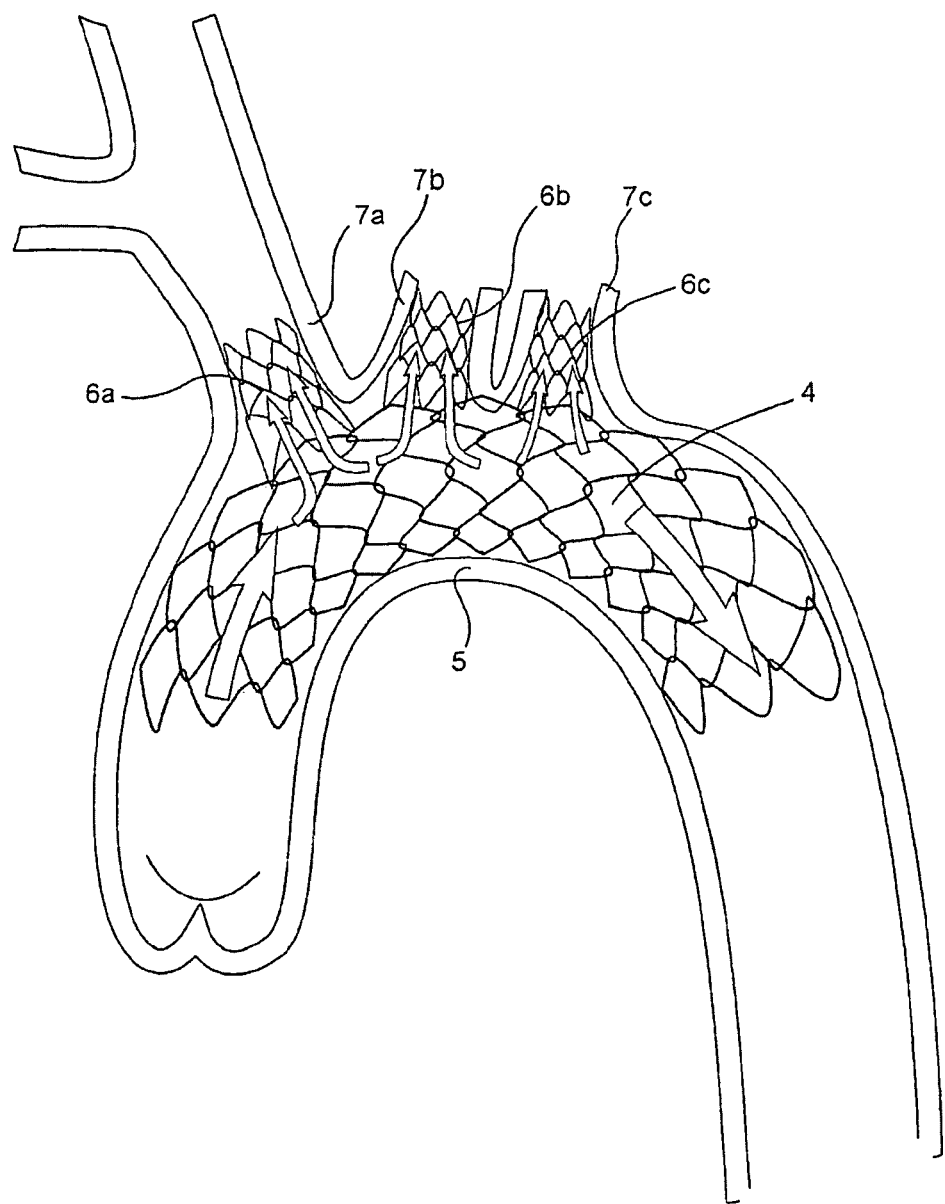

The implantation procedure for the subject devices will now be described with respect to FIGS. 8A-8H and in the context of an aortic arch application in which a stent-graft 2 of the present invention, such as that illustrated in FIG. 1A, having a main body lumen 4 and three side branch lumens 6*a*, 6*b* and 6*c*, is percutaneously implanted within the aortic arch 5, where, upon implantation, main body lumen 4 will reside within the aortic arch 5 and the three side branch lumens 6*a*, 6*b* and 6*c* will reside in the innominate artery 7*a*: the left common carotid artery 7*b* and the left subclavian artery 7*c*, respectively, as illustrated in FIG. 8H.

By means of a Seldinger technique via the left femoral artery 8, or abdominal aortotomy, a main or aortic guide wire 48 is advanced through the vasculature to the aortic arch 5 up to or until distal tip 48*a* is caused to cross the aortic valve 10, as illustrated in FIG. 8A. Catheter portion 32 of the implantation system 30 of the present invention, provided with stent-graft 2 operatively loaded therein, is then percutaneously introduced into the patient's body over guide wire 48.

It is noted that stent-grafts or stents otherwise covered with a material, e.g., an ECM, may require reconstitution or hydration of the graft or covering prior to commencing the implantation procedure. This may, be accomplished by flushing the guide wire lumen of delivery system catheter with saline prior to inserting the catheter into the body. Alternatively this could be done by rinsing in open air prior to sheathing.

While stent graft 2 is in a loaded, undeployed state within catheter portion 32, the delivery system's handle is in the retracted position, i.e., proximal handle portion 34*a* and distal handle portion 34*b* are engaged with each other. With the handle in the retracted position (shown in FIGS. 8B and 8D), inner member 42 is held in a distally advanced position and intermediate member 40 is held in a proximally retracted position. This relative axial relationship between the intermediate and inner members, maintains stent graft 2, or at least its main lumen 4, in a stretched or tensioned condition. This is so as the distal crowns of main lumen 4 are attached to the distal end of inner member 42, which in turn is fixed to proximal handle portion 34*a*, and the proximal crowns of main lumen 4 are attached to the distal end of 110 intermediate member 40, which in turn is fixed to the distal handle portion 36*b*.

Catheter portion 32 is then steered as necessary by means of manipulating lever 56, thereby deflecting the distal tip of catheter 32, as described above with respect to FIG. 4, and advanced into the descending aorta and then into aortic arch 5. It is important that catheter portion be properly rotationally positioned so that side branch lumens 6*a*, 6*b* and 6*c* of stent graft 2 are substantially aligned with arteries 7*a*, 7*b* and 7*c*, respectively, into which they are to be delivered. To this end catheter 32 is torquable and fluoroscopic guidance may be employed to further facilitate delivery of catheter portion 32. In particular, fluoroscopic markers (not shown) on the crowns of the stent graft lumens may be tracked and accurately positioned for optimal placement within the respective arteries. The stent itself may be radiopaque. The tip of the catheter will be radiopaque as well. A steerable guidewire may be used to direct the main catheter 32 and the side branch catheters as the stretched main stent body and side branch stent bodies are steered by deflectable tipped guidewires placed into the target implant site.

Throughout the delivery and deployment procedure, the various lumens of catheter portion 32 may be continuously flushed with a fluid, e.g., saline or contrast agent, in a retrograde direction (relative to the blood flow) at a pressure that is greater than or substantially equal to the pressure of the arterial blood. This prevents possible leakage of blood from the system as well as prevents any interference with the functioning of the delivery process, particularly keeping the stent strings lumens free and clear of blood, thereby eliminating clotting within the lumens. Additionally, because each lumenal end of the stent graft (i.e., the proximal and distal ends of main lumen 4 as well as the distal ends of the side branch lumens) is individually controlled (however, some or all may be collectively, controlled by the delivery and deployment system 30 of the present inventions the interconnected cells of the stent may be selectively elongated in an axially direction, permitting the continual flow of blood around the device during deployment within the anatomy. This axial elongation feature also permits the implantation of larger diameter side branch stents within a vessel having a smaller diameter.

Once the distal end of catheter portion 32 is operatively positioned (within the aortic arch 5, outer sheath 38 is retracted by manually pulling on fitting 50 (see FIG. 3A) to expose the proximal end of nose cone 46 of inner member 42 and to partially deploy the distal portion of the main or aortic lumen 4 of stent graft 2 within the ascending aorta, as shown in FIG. 8C. With partial deployment of stent graft 2, i.e. main aortic lumen 4 is maintained in a stretched or tensioned state, arterial blood flow exiting from aortic valve 10 flows through and around main lumen 4. It is important to note that with main lumen 4 in this partially deployed state, stent graft 2 can be easily repositioned within the vasculature as it is not yet engaged with the vessel walls and, thus, is not subject to the frictional resistance that contact with the walls would cause, not to mention the avoidance of the resulting endothelial damage and/or plaque embolization which is likely to occur.

While the various side branch lumens 6a, 6b and 6c of stent graft 4 may be deployed serially (one at a time) in any order or parallely (simultaneously) together, it may be easiest to deploy the side branch stent lumens one at a time in order from the most distally positioned stent lumen (6a) to the most proximally positioned stent lumen (6a). This deployment order eliminates unnecessary or repetitious translation of outer sheath 38 over the stent graft. i.e., only gradual, unidirectional (proximal) translation is necessary. This is advantageous in that abrasions to the graft material are minimized, which is particularly important when coated with a material, e.g., extra cellular matrix, or a drug. This deployment order further reduces the necessary deployment steps and, thus, the total time necessary for the implantation procedure.

To deploy a side branch stent lumen, such as stent lumen 6a, a side branch guide wire 154 is inserted into (or may be preloaded within) side branch port 110 of the respective control hub in its full distally advanced position and into a lumen 152 of side branch catheter 150 positioned within lumen 148 of intermediate member 40 (see FIG. 6A). At the same time, outer sheath 38 is incrementally and gradually retracted proximally to allow the distal end of guide wire 154 to be translated through side branch catheter 150, out its distal end and into innominate artery 7a, as shown in FIG. 8C. The respective control hub 74 is then distally translated along intermediate member 40 and may be fully engaged with the associated catheter hub 84, thereby exerting maximum tension being applied to the side branch stent cells by the attached attachment strings and partially deploying side branch stent 6a as shown in 8D. Note that the main body stent cells are being held stretched distal to proximal through the relative positions of the inner member and intermediate member as controlled by the handle in the close configuration while the side branch stent is likewise maintained in a stretched position by the distally advanced side branch catheter. This procedure is repeated as necessary for the remaining number of side branch stents, in this case, side branch stents 6b and 6c which are delivered into the left common carotid artery 7b and the left subclavian artery 7c, respectively, as illustrated in FIG. 8D. Note that at this partially deployed state the blood flow is around the device as well as through the implant depending on how tight and over what extension length the attachment strings are pulled to the inner member exit ports 184. It may be desirable to have just flow around the device and not through the lumen of the device and that can be accomplished by cinching down on the attachment strings on the distal end of main lumen to allow the most minimal length of attachment thereby bringing the main lumen of stentgraft to be held closed against distal tip 46 or inner member 42. It is important to note that the distance between the distal main stent end and its connection to the inner member is controllable by the length of distal attachment strings which are controlled by the string clamp 70b by adjusting and selecting the location of where the clamp locks onto the distal attachment strings. This adjustment can be made in situ while the stent is being delivered. Likewise the distance between the proximal main stent end and its connection to the intermediate member is controllable by the length of proximal attachment strings which are controlled by the string clamp 72b by adjusting and selecting the location of where the clamp locks onto the proximal attachment strings. This adjustment can be made in situ while the stent is being delivered.

After placement within the branch arteries of all of the side branch stents in their partially deployed states, the stent graft is ready for full deployment. This is accomplished by moving the system handle to the extended position, i.e., proximal handle portion 34a and distal handle portion 34b are axially separated from each other, as illustrated in FIG. 8E. This action causes inner member 42 to translate proximally relative to the fixed intermediate member 40 and in turn relaxes the tension applied to the cells of main lumen 4, thereby bringing the lumen ends closer together. As such, the stent foreshortens and there is a corresponding increase in the diameter of main lumen 4, thereby securing main lumen 4 against the walls of the aorta.

The side branch catheters are likewise translated proximally by moving the respective control hub 74, 76, 78 a distance further from its corresponding catheter hub 84, 86, 88 thereby relaxing the tension applied to the cells of the side branch stent. As such there is a corresponding increase in the diameter of side branch lumens 6a, 6b, 6c as the lumenal ends foreshorten. It is important to note that the distance between the stent ends and the catheter end is controllable by adjusting the length of the strings traversing between the fixed-end knob 70a, 72a, 74a, 76a, 78a and the releasable end clamp 70b, 72b, 74b, 76b, 78b.

Once the stent cells have been released of their tension by the translation of the catheter handle and side branch catheters, and as the stent opens to a diameter which is expanded against the surrounding artery wall, the entire blood flow enters through the distal end of the device and exits all of its other lumens. Preferably, blood flow is sealed from around the outside or the stentgraft once the stent has been fully deployed.

While the stent itself may be fully deployed as shown in FIG. 8E, it is still attached by attachment string sets to each of the distal ends of inner member 42, intermediate member 40 and each side branch catheter 150a, 150b, 150c. The lumenal ends of the stent graft can now be detached from their respective catheters. The stent graft's lumenal ends may be released serially (one at a time) in any order or parallely (simultaneously) together. As shown in FIG. 8F, the lumenal ends of the side branch lumens 6b and 6c have been released, with the respective attachment strings 190, side branch catheters 150a, 150b, 150c and side branch guide wires 154 having been retracted. For each side branch lumenal end, such as illustrated for side branch lumen 6a, catheter detachment is accomplished by actuating the designated control clamp 74b, 76b and 78b on its respective catheter hub 74, 76, 78 to release the free ends of strings 190 from the screw clamp of catheter hub and, at the same time, by remolding control knob 74a, 76a, 78a from the handle and pulling strings 190 to the extent that the free ends unloop or detach from the respective stent's crowns 128 of FIG. 8F. The strings 190 need only be pulled until their free ends release the crowns but may be withdrawn within the distal end of catheter portion 32.

As illustrated in FIG. 8G, a similar procedure is performed with respect to deployment of the distal and proximal ends of main lumen 4, where either end may be deployed first or both ends may be deployed simultaneously The designated control clamp 70b, 72b is actuated to release the free ends of strings 192 and, at the same time, control knobs 70a, 72a is removed from the handle thereby pulling strings 192 to the extent that the free ends unloop or detach from the respective stent's crowns 126. Strings 192 need only be pulled until their free ends release the crowns but may be withdrawn within the distal end of catheter portion 32. The entirety of catheter portion 32 may then be removed from the vasculature with stent graft 2 in a fully deployed state within the aortic arch 5, as shown in FIG. 8H.

Figure 11:
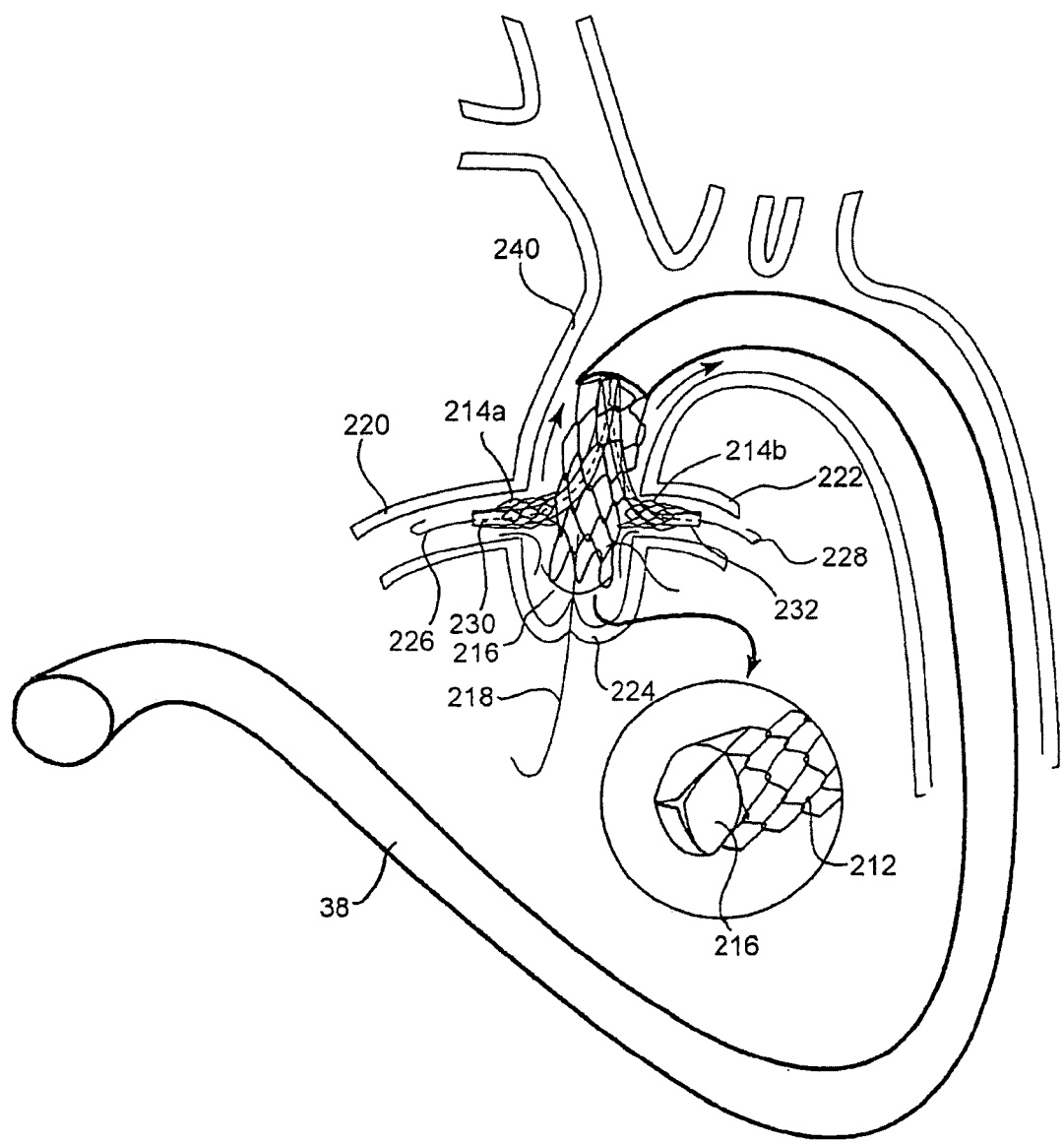
FIG. 11 illustrates the partial deployment of the implant of FIG. 1E within the aortic root.

Referring now to FIG. 11, the partial deployment step of the above described procedure is illustrated with respect to the delivery and deployment of the implant 210 of FIG. 1E. Specifically, catheter portion 38 of the delivery system is positioned within the aorta with the distal portion of main stent lumen 122 partially deployed within the aortic root and ascending aorta 240, and side branch lumens 214a and 214b partially deployed within the right and left coronary ostia 220 and 222, respectively. A main guidewire 218 extends from catheter 38 and crosses the former location of the natural aortic valve 224, while side branch guidewires 226 and 228 extend within the coronary ostia 220, 222 from side branch catheters 230 and 232, respectively. Upon release of the attachment strings for the main lumen of the implant, prosthetic aortic valve 216 will reside within the natural annulus 224. The side branch lumens 214a, 214b may be deployed simultaneously with each other and with main lumen 212, or serially in any order.

In any surgical or endovascular procedure, such as the one just described, the fewer incisions made within the patient, the better. Of course, this often requires highly specialized instrumentation and tools used by a highly skilled surgeon or physician. In consideration of this, the above-described single-incision device implantation procedure may be modified to include the creation and use of one or more secondary incisions to facilitate the initial delivery of the catheter portion 38 of the delivery system 32 at the implantation site and to further ensure proper orientation of the stent graft upon its deployment at the site.

The two-incision (or multiple-incision) procedure of the present invention involves a primary, incision, e.g., a cutdown in the femoral artery as described above, through which the above-described deliver and deployment system is introduced into a first vessel within the body, e.g., into the aortic arch, and a second incision (or more) at a location(s) that provides access to at least one vessel which intersects the first vessel, e.g., one of the side branches of the aortic arch. This procedure is now described with reference to FIGS. 12A-12F and in the context of implanting the stent graft 2 of the present invention in the aortic arch by use of a primary incision made in the left femoral artery 8 to access the aortic arch 5 and a single secondary incision made in the brachialcephalic or radial artery 15 to access one or more arteries of the aortic tree.

First and second access incisions are made—in the left femoral artery 8 and the left brachycephalic artery 15, respectively. Bar means of a Seldinger technique, a secondary or "tether" guide wire 300 is advanced through the left brachycephalic artery 15 into the innominate artery 7. Guide wire 300 is then further advanced into the aortic arch 5, the descending aorta 11, the abdominal aorta 13 and the left femoral artery 8 where it exits the body through the femoral incision, as illustrated in FIG. 12A. A secondary or "tether" catheter 302 is then tracked over the femoral end 300a of guide wire 300 and along the length of the guide wire until catheter 302 is advanced out of the brachial incision, as illustrated in FIG. 12B. Any suitable off-the-shelf system for cardiovascular applications ma) be employed for use as the secondary or tether guide wire and catheter. A dual lumen rapid-exchange (RX) catheter, such as the one illustrated, having a second lumen positioned at the proximal end of catheter 302. An advantage of an RX catheter is that it only requires the string(s) (or a guidewire) to be pushed a relatively short distance (requiring little "pushability") before it exits the lumen rather than a greater distance in which the string would be difficult to push due to its limp nature. Alternatively, the very end of catheter 302 may be provided with a thru-hole or a cross-hole in the catheter wall, as illustrated in FIG. 12C'.

The above descried implantation system 30 is then provided with stent-graft 2 operatively loaded therein. For this procedure, as illustrated in FIG. 12C, side branch attachment strings 190, or at least one string thereof, for deploying the most distally located side branch stent lumen 6a (i.e., the one intended for implantation into the innominate artery 7a) and attached thereto (to one or more stent crowns) are extended from side branch catheter 150a of primary or stent delivery system catheter 38 and then threaded through a side branch tether tubing 35. The strings are then knotted 37a to prevent proximal withdrawal back into catheter 150a and tubing 35. The remaining distal length of strings 190 are then threaded through the exchange lumen 304 of tether catheter 302. The ends of the strings are then knotted a second time 37b to prevent proximal withdrawal of the strings from exchange lumen 304. With the secondary catheter embodiment of FIG. 12C', the strings are threaded into the main lumen 302 and out the side hole 305. The distal string ends are then knotted 37b.

Figure 12D:
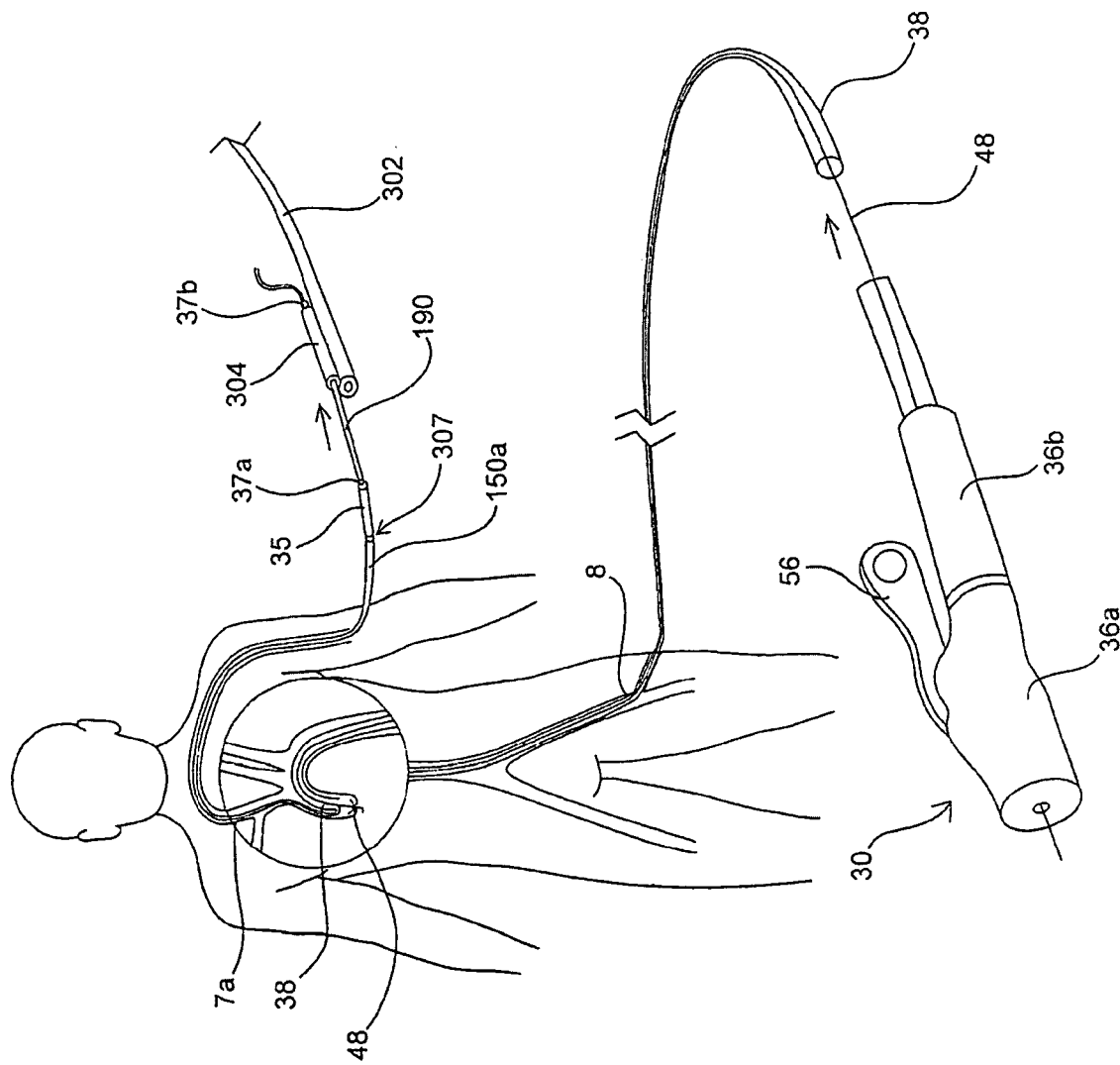

Secondary catheter 302, with side branch catheter 15a in tow as well as the entirety of stent catheter 38 including primary or main guide wire 48, is then advanced back through the femoral incision over secondary guide wire 300 until catheter 302 is fully withdrawn from the brachial incision, as illustrated in FIG. 12D, and until the distal end of side branch catheter 150a is also extended from the brachial incision. Tether guide wire 300 can now be removed from the body. At this point, strings 190 are cut at a location 307 between the distal end of side branch catheter 150a and the opposing end of secondary catheter 302 to release the tether catheter 302 from the stent deployment system.

Figure 12E:
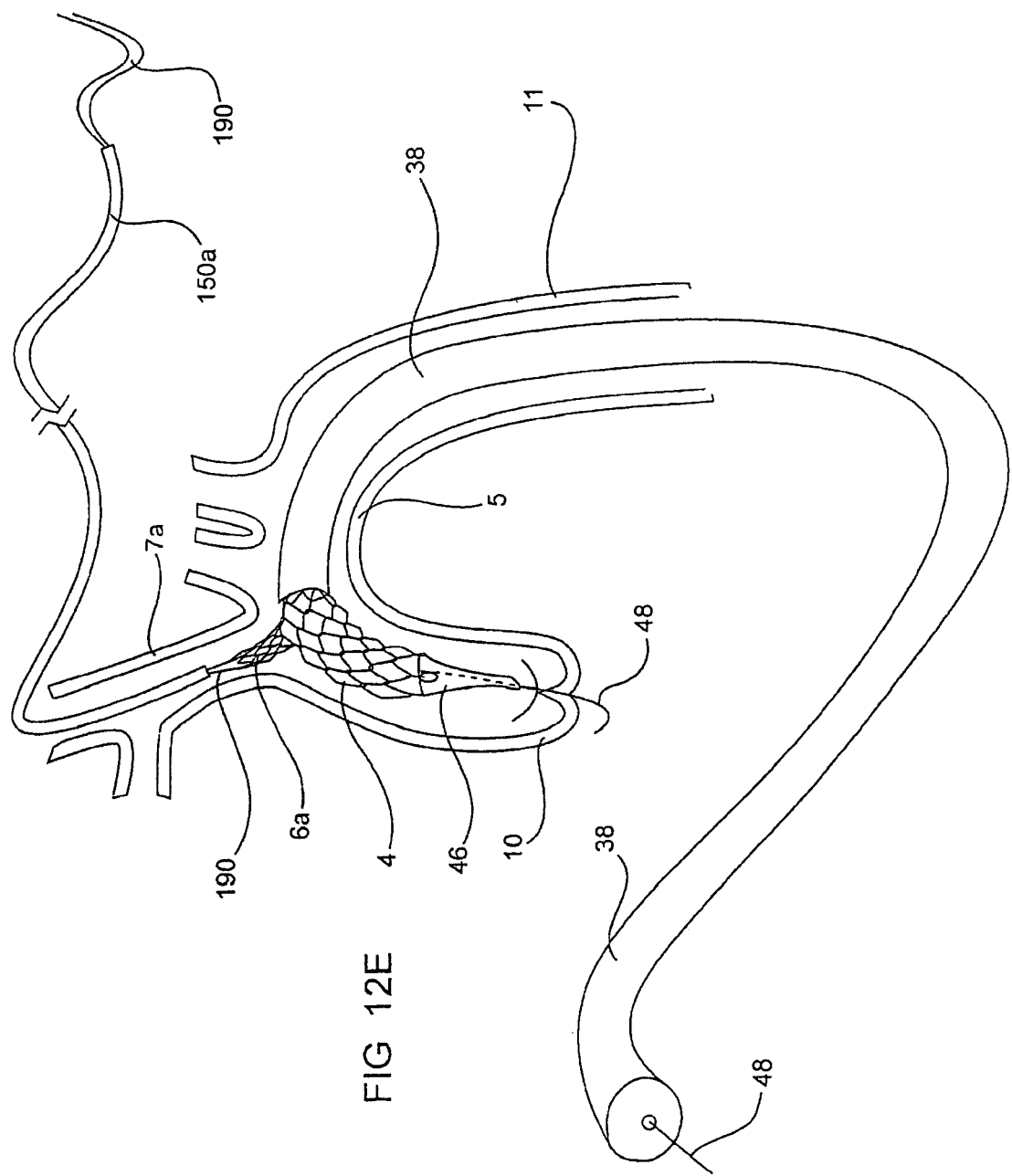

By the tension applied to strings 190 and the translation thereof, side branch 6a of stent graft 4 has been dragon into the innominate artery 7a, as illustrated in FIG. 12E, in a partially deployed state (i.e., exposed but stretched). Concurrently, stent guide wire 48 is advanced over the aortic arch 5 and across the aortic valve 10, thereby advancing nose cone 46 and thus the distal end of the partially deployed (i.e., exposed but stretched or tensioned) main stent lumen 4 into the ascending aorta. Meanwhile, stent catheter 38 has been tracked over stent guide wire 48 into the aortic arch 5. Continued forward advancement of stent catheter 38 is blocked by the partially deployed side branch lumen 6a. As discussed above, with main lumen 4 maintained in a stretched or tensioned state (as well as side branch lumen 6a), various advantages are provided: arterial blood flow exiting from aortic valve 10 is allowed to flow to the brain and body: repositioning of the stent graft 2 is possible, and the likelihood of endothelial damage and/or plaque embolization from the aortic wall is greatly minimized.

Figure 12F:
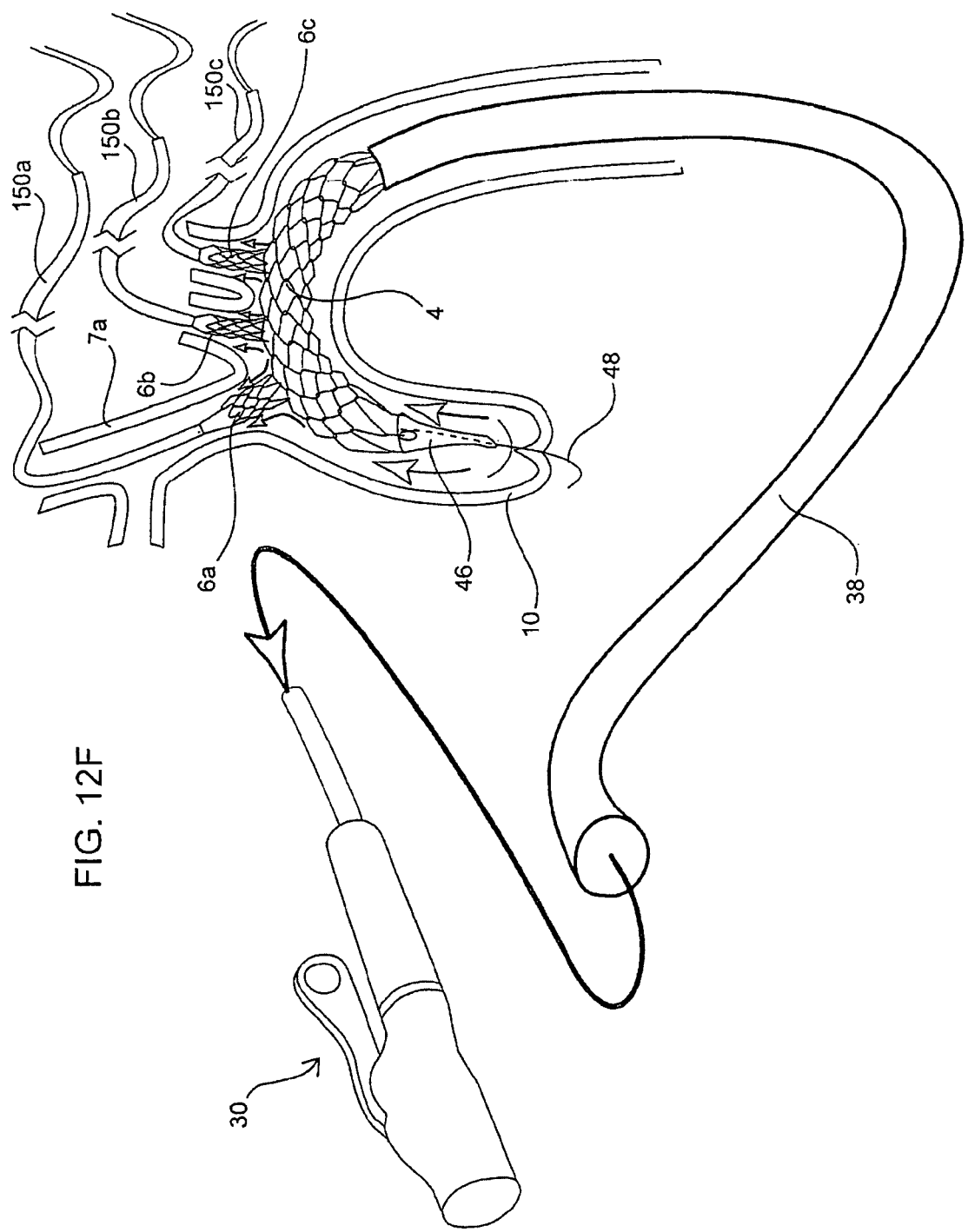

For stents and stent grafts having two or more side branch lumens 6a, 6b, 6c, as in FIG. 12F, the procedure described above and illustrated in FIGS. 12A-12E with respect to the implantation of a stent having a single side branch lumen is simultaneously performed, with separate designated tether guide wires and catheters 150a, 150b, 150c. As illustrated in FIG. 12F, with at least the distal end of the main stent lumen 4 accurately positioned and partially deployed within the ascending aorta, the respective side branch lumens 6a, 6b, 6c are deployed within the innominate artery 7a, left common carotid artery 7b and the left subclavian artery 7c, respectively. Alternatively, one or more of the side branch lumens may be partially deployed as described with respect to FIGS. 12A-12F, and the remaining side branch lumens, if any, may be deployed in the manner described above with respect to FIGS. 8C and 8D. Finally, with all side branch lumens 6a, 6b, 6c partially deployed within their respective arteries, the procedural steps described with respect to FIGS. 8E-8H may be performed to fully deploy the all lumens of the stent graft and remove the deliver, system from the body.

While the implants of the present invention have been described as being deployable by elongated members, i.e. strings, it is understood that the subject implants may be configured such that their lumenal ends are configured for deployment by an expandable member or members. For example, each of the ends of the implant (i.e., of the main lumen and of the side branch lumen(s)), in a loaded, undeployed state, may be coupled to one or more of the nested catheters by placement about an expandable balloon affixed to the catheter(s). The balloons, in either a partially or fully expanded state, provide a sufficiently snug fit with the implant ends such that the lumens of the implant may be selectively stretched or tensioned along their lengths when manipulating the catheter components.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplar embodiments shown and described herein. Rather, the scope and spirit of present invention is embodied by the appended claims.

That which is claimed is:

1. An implant delivery system for use within a vessel or tubular structure within the body, the system comprising:
   an implant having a distal end and a proximal end defining a length there between and having a diameter;
   a first catheter configured for slidable retention of the implant therein where the proximal end of the implant is releasably connected to the first catheter through an intermediate member located within the first catheter;
   at least one string releasably coupled to a first free end of the implant;
   a second catheter configured for removable attachment to the at least one string, where the string allows for controlling and releasably attaching the first free end of the implant to the second catheter;
   wherein the first and second catheters are in substantial co-axial alignment with each other upon attachment of the at least one string to the second catheter, such that the first and second catheters stretch the implant in a reduced diameter, and relative axial movement between the first and second catheter in a first direction unstretches and expands the implant to cause partial deployment of the implant within the vessel or tubular structure and relative axial movement between the first or second catheter in a second direction restretches the implant for repositioning;
   where when the implant is partially sheathed in the first catheter, an unsheathed portion of the implant is selectively expandable and contractible;
   where detachment of the at least one string from the implant causes full expansion and deployment of the free end of the implant from the second catheter; and
   where the intermediate member is in substantial co-axial alignment with the first and second catheters.

2. The system of claim 1 further comprising a guide wire over which both of the catheters are trackable, where when the implant is partially sheathed in the first catheter, a diameter of the unsheathed portion of the implant is selectively expandable and contractible.

3. The system of claim 2 further comprising at least a second guide wire to which an end of the implant is releasably attached, wherein the implant further comprises a main lumen along the length and at least one side branch lumen extending from the main lumen and having a distal end, wherein the at least one string is adapted for releasable attachment to the distal end of the at least one side branch lumen, and where the second catheter has multiple lumens, the system further comprising a mechanism for selectively tensioning the string to selectively increase and selectively reduce a profile of the side branch lumen.

4. The system of claim 1, further comprising a second string releasably coupled to a first free end of the implant.

5. The system of claim 1, where the implant further comprises a branching lumen branching from the implant, and where the system further comprises a third catheter and a third string, the third catheter being coaxial with at least the first catheter and where the third string is releasably coupled to a free end of the branching lumen.

6. The system of claim 1, wherein the at least one string has a first and second ends and a central portion therebetween, where the first and second ends of the at least one string each extend through a separate lumen within the second catheter and the central portion of the at least one string is weaved through apices of a distal end of implant.

7. The system of claim 1, where the relative axial movement between the first and second catheter in the first direction causes the diameter of the implant to increase and where the relative axial movement between the first or second catheter in the second direction causes the diameter of the implant to decrease.

8. The system of claim 1, where the relative axial movement between the first and second catheter in the first direction causes the implant to change from an implant first configuration to an implant second configuration, where the diameter of the implant is larger in the implant second configuration than in the implant first configuration, and where the length of the implant is less in the implant second configuration than in the implant first configuration.

9. The system of claim 1, where the relative axial movement between the first and second catheter in the first direction causes the implant to change from an implant first configuration to an implant second configuration, where a distal portion of the implant is in the first catheter in the implant first configuration and out of the first catheter in the implant second configuration, where when the implant is in the implant second configuration, the distal portion of the implant is positioned distal to the first catheter, where the relative axial movement between the first or second catheter in the second direction causes the implant to change from the implant second configuration to the implant first configuration such that the distal portion of the implant moves back into the catheter and where the implant second configuration is a partially deployed configuration.

10. An implant delivery system for use within a vessel or tubular structure within the body, the system comprising:
an implant having a distal end and a proximal end defining a length there between and having a diameter, where the implant comprises a main lumen and a side branch lumen;
a first catheter configured for slidable retention of the implant therein where the proximal end of the implant is releasably connected to the first catheter through an intermediate member located within the first catheter;
at least one string releasably coupled to a first free end of the implant;
a second catheter configured for removable attachment to the at least one string, where the string allows for controlling and releasably attaching the first free end of the implant to the second catheter;
wherein the first and second catheters are in substantial co-axial alignment with each other upon attachment of the at least one string to the second catheter, such that the first and second catheters stretch the implant in a reduced diameter, and relative axial movement between the first and second catheter in a first direction unstretches and expands the implant to cause partial deployment of the implant within the vessel or tubular structure and relative axial movement between the first or second catheter in a second direction restretches the implant for repositioning;
where the relative axial movement between the first and second catheter in the first direction causes the diameter of the implant to increase;
where the relative axial movement between the first or second catheter in the second direction causes the diameter of the implant to decrease;
where when the main lumen is partially sheathed in the first catheter, the side branch lumen is positionable in a side branch vessel; and
where detachment of the at least one string from the implant causes full expansion and deployment of the free end of the implant from the second catheter.

11. The system of claim 10, where the relative axial movement between the first and second catheter in the first direction causes the implant to change from an implant first configuration to an implant second configuration, where when the implant is in the implant first configuration, a distal portion of the implant is in the first catheter, where when the implant is in the implant second configuration, the distal portion of the implant is out of the first catheter and distal to the first catheter, where the relative axial movement between the first or second catheter in the second direction causes the implant to change from the implant second configuration to the implant first configuration such that the distal portion of the implant moves back into the catheter, where the implant second configuration is a partially deployed configuration, where the intermediate member is in substantial co-axial alignment with the first and second catheters, and where the intermediate member has multiple lumens.

12. The system of claim 10, where when the main lumen is partially sheathed in the first catheter, an exposed portion of the main lumen is selectively expandable and contractible.

13. The system of claim 10, where when the main lumen is partially sheathed in the first catheter and the side branch lumen is partially sheathed in the first catheter, an exposed portion of the main lumen is expandable and contractible.

14. The system of claim 10, where when the side branch lumen is partially sheathed in the first catheter, an exposed portion of the main lumen is selectively expandable and contractible and an exposed portion of the side branch lumen is selectively expandable and contractible.

15. The system of claim 14, where the exposed portion of the main lumen and the exposed portion of the side branch lumen are each independently selectively expandable and contractible.

16. An implant delivery system for use within a vessel or tubular structure within the body, the system comprising:
an implant having a distal end and a proximal end defining a length there between and having a diameter, where the implant comprises a main lumen and a side branch lumen;
a first catheter configured for slidable retention of the implant therein where the proximal end of the implant is releasably connected to the first catheter through an intermediate member located within the first catheter;
at least one string releasably coupled to a first free end of the implant;
a second catheter configured for removable attachment to the at least one string, where the string allows for controlling and releasably attaching the first free end of the implant to the second catheter;
wherein the first and second catheters are in substantial co-axial alignment with each other upon attachment of the at least one string to the second catheter, such that the first and second catheters stretch the implant in a reduced diameter, and relative axial movement between the first and second catheter in a first direction unstretches and expands the implant to cause partial deployment of the implant within the vessel or tubular structure and relative axial movement between the first or second catheter in a second direction restretches the implant for repositioning;
where the relative axial movement between the first and second catheter in the first direction causes the implant to change from an implant first configuration to an implant second configuration;
where when the implant is in the implant first configuration, a distal portion of the implant is in the first catheter;
where when the implant is in the implant second configuration, the distal portion of the implant is out of the first catheter and positioned distal to the first catheter;
where the relative axial movement between the first or second catheter in the second direction causes the implant to change from the implant second configuration to the implant first configuration such that the distal portion of the implant moves back into the catheter;

where when the side branch lumen is partially sheathed in the first catheter, the main lumen is selectively expandable and contractible and the side branch lumen is selectively expandable and contractible; and where detachment of the at least one string from the implant causes full expansion and deployment of the free end of the implant from the second catheter.

17. The system of claim 16, where the implant second configuration is a partially deployed configuration, where the intermediate member is in substantial co-axial alignment with the first and second catheters, and where the intermediate member has multiple lumens around the second catheter or where the second catheter has multiple lumens that extend through the intermediate member.

18. The system of claim 16, where the implant second configuration is a fully deployed configuration.

19. The system of claim 16, where when the side branch lumen is partially sheathed the first catheter, the main lumen is selectively expandable and contractible independently of the side branch lumen.

20. The system of claim 16, where when the main lumen is partially sheathed in the first catheter and the side branch lumen is partially sheathed in the first catheter, an exposed portion of the main lumen is selectively expandable and contractible.

* * * * *